US007365090B2

(12) United States Patent
Artico et al.

(10) Patent No.: US 7,365,090 B2
(45) Date of Patent: Apr. 29, 2008

(54) SUBSTITUTED PHENYLINDOLES FOR THE TREATMENT OF HIV

(75) Inventors: Marino Artico, Rome (IT); Paolo LaColla, Cagliari (IT); Romano Silvestri, Rome (IT); Adel Moussa, Burlington, MA (US); Jean-Pierre Sommadossi, Cambridge, MA (US); Richard Storer, Folkestone (GB)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 263 days.

(21) Appl. No.: 10/637,949

(22) Filed: Aug. 7, 2003

(65) Prior Publication Data

US 2004/0180945 A1 Sep. 16, 2004

Related U.S. Application Data

(60) Provisional application No. 60/401,915, filed on Aug. 7, 2002.

(51) Int. Cl.
*A61K 31/405* (2006.01)
*C07D 209/14* (2006.01)

(52) U.S. Cl. ...................................... 514/415; 548/503
(58) Field of Classification Search ................ 514/415; 548/503
See application file for complete search history.

(56) References Cited

U.S. PATENT DOCUMENTS

| | | | |
|---|---|---|---|
| 4,866,084 A | 9/1989 | Gunasekera et al. | |
| 5,124,327 A | 6/1992 | Greenlee et al. | |
| 5,489,685 A | 2/1996 | Houpis et al. | |
| 5,527,819 A | 6/1996 | Williams et al. | |
| 5,830,894 A | 11/1998 | Pevear et al. | |
| 5,852,011 A | 12/1998 | Matsunaga et al. | |
| 5,929,114 A | 7/1999 | Domagala et al. | |
| 5,935,982 A | 8/1999 | Dykstra et al. | |
| 5,945,440 A | 8/1999 | Kleinschroth et al. | |
| 5,981,525 A | 11/1999 | Farina et al. | |
| 6,025,390 A | 2/2000 | Farina et al. | |
| 6,710,068 B2* | 3/2004 | LaColla et al. | 514/414 |
| 2002/0193415 A1 | 12/2002 | LaColla et al. | |

FOREIGN PATENT DOCUMENTS

| | | |
|---|---|---|
| EP | 0 530 907 A1 | 3/1993 |
| WO | WO 94/19321 | 9/1994 |
| WO | WO 02/083126 | 10/2002 |

OTHER PUBLICATIONS

Balani, S.K., et al., "Biotransformation of 5-chloro-3-phenylthioindole-2-carboxamide (L-734,005) in rhesus monkeys and rat liver microsomes to a potent HIV-1 reverse transcriptase inhibitor," *Drug Metabolism and Disposition*, 21(4):598-604 (1993), in Chemical Abstract No. 119:216694 (1993).

Chen, C.-y., et al., Syntheses of indoles via a palladium-catalyzed annulation between iodoanilines and ketones, *J. Org. Chem.*, 62(9):2676-2677 (1997).

Clauson-Kaas, N. et al., "Preparation of *cis* and *trans* 2,5-dimethoxy-2-(acetamido-methyl)-2,5-dihydrofuran, of *cis* and *trans* 2,5-dimethoxy-2-(acetamido-methyl)-tetrahydrofuran and of 1-phenyl-2-(acetamidomethyl)-pyrrole,"*Acta Chem. Scand.*, 6:667-670 (1952).

Elming, N., "The preparation of pyrroles from furans," *Acta Chem. Scand.*, 6:867-874 (1952).

Gagliardi, S. et al., "5-(5,6-dichloro-2-indolyl)-2-methoxy-2,4-pentadienamides: novel and selective inhibitors of the vacuolar $H^+$-ATPas of osteoclasts with bone antiresorptive activity," *J. Med. Chem.*, 41:1568-1573 (1998).

Pauwels, R. et al. "Potent and highly selective human immunodeficiency virus type 1 (HIV-1) inhibition by a series of α-anilinophenylacetamid derivatives targeted at HIV-1 reverse transcriptase," *Proceedings of the National Academy of Sciences USA*, 90:1711-1715 (1993).

Pauwels, R. et al., "Potent and selective inhibition of HIV-1 replication in vitro by a novel series of TIBO derivatives," *Nature*, 343:470-474 (1990).

Phillips, R.B., "The Japp-Klingemann reaction," *Org. Reactions*, 10:143-178 (1959).

Romero, D. L. et al., "Bis(heteroaryl)piperazine (BHAP) reverse transcriptase inhibitors: Structure-activity relationships of novel substituted indole analogues and the identification of 1-[(5-methane-sulfonamido-1-*H*-indol-2-yl)-carbonyl]-4-[3-[(1-methyl)amino]-pyridinyl]piperazine monomethane-sulfonate (U-90125S), a second-generation clinical candidate," *J. Med. Chem.*, 36:1505-1508 (1993).

Williams, T.M, et al., "5-Chloro-3-(phenylsulfonyl)indole-2-carboxamide: A novel, non-nucleoside inhibitor of HIV-1 reverse transcriptase," *Journal of Medicinal Chemistry*, 36(9):1291-94 (1993). Chemical Abstract No. 119:49174 1993.

Bolani, et al., Biotranformation of 5-chloro-3-phenylthioindole-2-carbooximide in rhesus monkeys and rat liver microsomes to a potent HIV-1 reverse transcripase inhibitor, abstract, 1993; No. 119:216694.

* cited by examiner

Primary Examiner—Kamal A. Saeed
(74) Attorney, Agent, or Firm—Jones Day

(57) ABSTRACT

This invention is in the area of phenylindoles that are useful for the treatment of HIV infection, and, in particular, phenylindoles that exhibit significant activity against resistant strains of HIV. The phenylindoles have at least two substituents other than hydrogen on the benzo ring of the indole function, preferably at the 4' and 5', 5' and 6' or the 5' and 7' positions, optionally in combination with disubstitution at positions 3" and 5" on the phenyl ring of the compound, and carboxamide containing moieties at position-2 on the indole group of the compound. Methyl is a preferred group for substitution on the phenyl ring. Preferred substituents for the benzo ring of the indole function include but are not limited to chlorine, fluorine, bromine, iodine, $CF_3$, methoxy, CN, and $NO_2$.

26 Claims, No Drawings

SUBSTITUTED PHENYLINDOLES FOR THE TREATMENT OF HIV

CROSS-REFERENCE OF THE INVENTION

This application claims priority to U.S. Provisional Application No. 60/401,915, filed on Aug. 7, 2002, the disclosure of which is herein incorporated by reference.

FIELD OF THE INVENTION

This invention is in the area of phenylindoles that are useful for the treatment of HIV infection, and, in particular, phenylindoles that exhibit significant activity against resistant strains of HIV.

BACKGROUND OF THE INVENTION

In 1983, the etiological cause of AIDS was determined to be the human immunodeficiency virus (HIV). Numerous compounds have since been synthesized to combat the virus, designed to inhibit progression beyond various stages of the virus's lifecycle. A focal point in AIDS research efforts has been the development of inhibitors of human immunodeficiency virus (HIV-1) reverse transcriptase (RT), an enzyme responsible for the reverse transcription of the retroviral RNA to proviral DNA (Greene, W. C., New England Journal of Medicine, 1991, 324, 308-317; Mitsuya, H. et al., Science, 1990, 249, 1533-1544; De Clercq, E., J. Acquired Immune Defic. Syndr. Res. Human. Retrovirus, 1992, 8, 119-134). Promising inhibitors include nonnucleoside reverse transcriptase inhibitors (NNRTIs), which bind to a specific allosteric site of HIV-1 RT near the polymerase site and interfere with reverse transcription by altering either the conformation or mobility of RT, thereby leading to noncompetitive inhibition of the enzyme (Kohlstaedt, L. A. et al., Science, 1992, 256, 1783-1790).

Several classes of compounds have been identified as NNRTIs of HIV-1. Examples include the following:
(a) 1-[(2-hydroxyethoxy)methyl]-6-(phenylthio)thymines (HEPT; Tanaka, H. et al., J. Med. Chem., 1991, 34, 349-357; Pontikis, R. et al., J. Med. Chem., 1997, 40, 1845-1854; Danel, K., et al., J. Med. Chem., 1996, 39, 2427-2431; Baba, M., et al., Antiviral Res, 1992, 17, 245-264);
(b) bis(heteroaryl)piperazines (BHAP; Romero, D. L. et al., J. Med. Chem., 1993, 36, 1505-1508);
(c) dihydroalkoxybenzyloxopyrimidine (DABO; Danel, K. et al., Acta Chemica Scandinavica, 1997, 51, 426-430; Mai, A. et al., J. Med. Chem., 1997, 40, 1447-1454);
(d) 2'-5'-bis-O-(tertbutyldimethylsilyl)-3'-spiro-5"-(4"-amino-1",2"-oxathiole-2",2"-dioxide) pyrimidines (TSAO; Balzarini, J. et al., Proc. Natl. Acad. Sci. USA, 1992, 89, 4392-4396);
(e) phenethylthiazolylthiourea (PETT) derivatives (Bell, F. W. et al., J. Med. Chem., 1995, 38, 4929-4936; Cantrell, A. S. et al., J. Med. Chem., 1996, 39, 4261-4274);
(f) tetrahydro-imidazo[4,5,1-jk][1,4]-benzodiazepine-2 (1H)-one and -thione (TIBO) derivatives (Pauwels, R. et al. Nature, 1990, 343, 470-474);
(g) alpha-anilinophenylacetamide (alpha-APA) derivatives (Pauwels, R. et al. Proceedings of the National Academy of Sciences USA, 1993, 90, 1711-1715); and
(h) indole derivatives (Williams et al., U.S. Pat. No. 5,527,819 (Jun. 18, 1996); and its counterpart PCT application PCT/US94/01694, published as WO 94/19321 on Sep. 1, 1994).

The indole derivatives identified by Williams et al., assigned to Merck & Co., in U.S. Pat. No. 5,527,819 received particular interest because of their ability to inhibit potently HIV reverse transcriptase. A number of these compounds displayed $EC_{90}$'s against HIV reverse transcriptase at concentrations as low as 2 micromolar. However, while this work was not pursued, it resulted in a novel process for synthesizing optionally substituted indoles by a palladium-catalyzed annulation between a ketone and an iodoaniline (Chen et al., J. Org. Chem., 1997, 62(9): 2676-77).

The compounds disclosed in the '819 patent comprise a large class represented generally by the following broad structural formula:

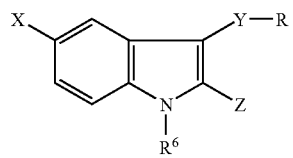

in which the variables X, Y, Z, R and $R^6$ were broadly defined to encompass a plethora of compounds. The patent presented examples for nearly one hundred of the compounds encompassed by the structure, and included several examples in which Z was —C(O)$NH_2$, Y was $SO_2$ and R was phenyl or substituted phenyl.

U.S. Pat. No. 5,124,327, issued Jun. 23, 1992 to Greenlee et al. and assigned to Merck disclosed a class of compounds of the general formula above, in which X is H, $R^6$ is H, Y is S, and R is phenyl. The patent disclosed that the compounds act as reverse transcriptase inhibitors.

WO 02/083126 to Idenix Pharmaceuticals, Ltd., disclosed a class of phenylindoles substituted with at least two moieties other than hydrogen on either the phenyl ring or the benzyl ring of the indole function, or on both rings. The substituents are preferably contained at the 3" and 5" positions if located on phenyl ring, and at the 4' and 5'; 5' and 6' or the 5' and 7' positions if located on the benzyl ring of the indole function.

Indoles have been used for the treatment of a variety of diseases other than HIV. For example, Farina et al., in U.S. Pat. No. 5,981,525 (Nov. 9, 1999), disclose a complex array of indoles that are useful for the treatment of osteoporosis, because they reduce bone resorption by inhibiting osteoclast $H^+$-ATPase.

U.S. Pat. No. 6,025,390, granted Feb. 15, 2000 to Farina et al., discloses another complex array of indole derivatives, referred to as heteroaromatic pentadienoic acid derivatives, and again suggest their use for the treatment of osteoporosis.

U.S. Pat. No. 5,489,685, granted Feb. 6, 1996, Houpis et al. discloses a similar set of compounds in the furo(2,3-b) pyridine carboxylic acid ester class, and specifically suggest their use for the treatment of HIV.

U.S. Pat. No. 5,945,440 to Kleinschroth et al. discloses a class of indolocarbazole amides, and proposes their use for a variety of diseases including cancer, viral diseases (including HIV), heart and blood vessel diseases, bronchopulmonary diseases, degenerative diseases of the central nervous system, inflammatory disorders, and other diseases.

Gunasekera et al., in U.S. Pat. No. 4,866,084 (Sep. 12, 1989), disclose a class of bisindole alkaloid compounds, and state that the compounds are useful as antiviral and antitumor agents. The patent also describes the compounds' activity against HSV (herpes simplex virus).

Matsunaga et al., in U.S. Pat. No. 5,852,011 (Dec. 22, 1998), disclose a class of indole derivatives substituted by a heteroaryl function and an amide function.

The compounds are said to possess antitumor, antiviral, and antimicrobial properties.

Dykstra et al., in U.S. Pat. No. 5,935,982 disclose a class of bis-indoles and specifically propose their use for treating retroviral infections, and especially infection by HIV.

Domagala et al., in U.S. Pat. No. 5,929,114 (Jul. 27, 1999) disclose a class of arylthio and bithiobisarylamide compounds that reportedly have antibacterial and antiviral activity. The invention is said to encompass indole derivatives as well.

Pevear et al., in U.S. Pat. No. 5,830,894 (Nov. 3, 1998) disclose a class of triazinoindole derivatives that reportedly have anti-pestivirus activity, most notably BVDV activity.

It is known that over a period of time, antiviral agents that are active against HIV induce mutations in the virus that reduce the efficacy of the drug. This was apparently the problem exhibited by the Merck indoles in U.S. Pat. No. 5,527,819 (Williams et al., *Journal of Medicinal Chemistry*, 1993, 36(9), 1291-94). Drug resistance most typically occurs by mutation of a gene that encodes an enzyme used in viral replication, and most typically in the case of HIV, reverse transcriptase, protease, or DNA integrase. It has been demonstrated that the efficacy of a drug against HIV infection can be prolonged, augmented, or restored by administering the compound in combination or alternation with a second, and perhaps third, antiviral compound that induces a different mutation from that caused by the principal drug. Alternatively, the pharmacokinetics, biodistribution, or other parameters of a drug can be altered by such combination or alternation therapy. In general, combination therapy is typically preferred over alternation therapy since combination therapy induces multiple simultaneous pressures on the virus. However, one cannot predict which mutations will be induced in the HIV-1 genome by a given drug, whether the mutations are permanent or transient, or how an infected cell with a mutated HIV-1 sequence will respond to therapy with other agents in combination or alternation. These factors are exacerbated by the fact that there is a paucity of data on the kinetics of drug resistance in long-term cell cultures treated with modern antiretroviral agents.

Therefore, there is a need to improve the duration of antiviral efficacy produced by antiretroviral drugs, and to provide antiviral drugs that are effective against strains of the virus that have developed cross resistance through mutational adaptation. Further, although many of the non-nucleotide reverse transcriptase inhibitors (NNRTI) in the prior art exhibit favorable pharmacokinetic and biodistribution profiles, there remains a need to improve upon these parameters.

It is an object of the present invention to provide new compounds for the treatment of patients infected with HIV. There is a special need to provide new compositions and methods for the treatment of patients infected with HIV that exhibit significant activity against drug-resistant forms of the virus.

SUMMARY OF THE INVENTION

A novel class of phenylindoles has been discovered that display significant antiviral activity against HIV, and in particular, strains of the HIV that have developed cross resistance to other anti-HIV drugs. Surprisingly, it has been discovered that HIV activity can be enhanced, and in certain cases cross resistance can be substantially overcome, by incorporating into the molecule at least two substituents other than hydrogen on the benzo ring of the indole function, optionally in combination with disubstitution at positions 3" and 5" on the phenyl ring of the compound, and by incorporating particular substituents having a carboxamide function at position-2 on the indole group of the compound, given as "Z" in Figure (I) below. In certain instances, monosubstitution on the benzo ring of the indole function in combination with defined "Z" carboxamide-containing substituents and optional disubstitution on the phenyl ring also provides unexpected, enhanced activity against HIV strains.

The substituents are preferably contained at the 3" and 5" positions if located on phenyl ring, and at the 4' and 5', 5' and 6' or the 5' and 7' positions if located on the benzo ring of the indole function. Methyl is a preferred group for substitution on the phenyl ring. Preferred substituents for the benzo ring of the indole function include but are not limited to chlorine, fluorine, bromine, iodine, $CF_3$, methoxy, CN, and $NO_2$.

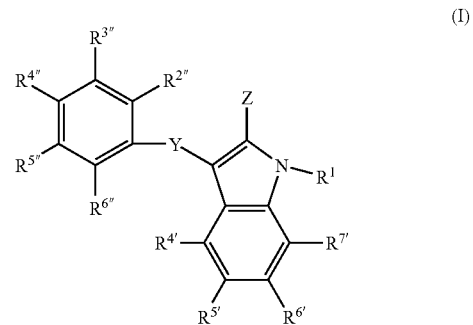

(I)

The active compound may be given as a salt or prodrug that upon administration to the recipient is capable of providing directly or indirectly the parent compound or that exhibits the desired activity itself. Modifications affecting the biological activity of the compounds are also included here, and embrace changes that produce increased activity over that of the parent compounds.

DETAILED DESCRIPTION OF THE INVENTION

The invention as disclosed herein is a method and composition for the treatment of retroviral infections in mammals and, in particular, HIV in humans. This method and composition includes the administration of an effective HIV treatment amount of a phenylindole as described herein, an enantiomer, diastereomer, tautomer, pharmaceutically acceptable salt or prodrug thereof, optionally in a pharmaceutically acceptable carrier.

The compounds of this invention either possess antiviral (i.e., anti-HIV) activity, or are metabolized to a compound that exhibits such activity.

In summary, the present invention includes the following features:
phenylindoles and their pharmaceutically acceptable salts and prodrugs thereof as described herein;
phenylindoles and their pharmaceutically acceptable salts and prodrugs thereof as described herein substantially free of other chemical entities;
phenylindoles and their pharmaceutically acceptable salts and prodrugs thereof as described herein that are effective against HIV in a host;

phenylindoles and their pharmaceutically acceptable salts and prodrugs thereof as described herein that are effective against drug-resistant strains of HIV in a host;

phenylindoles and their pharmaceutically acceptable salts and prodrugs thereof as described herein that are effective against drug-resistant strains of HIV due to a reverse transcriptase mutation, such as lysine 103→asparagine and/or tyrosine 181→cysteine;

phenylindoles and their pharmaceutically acceptable salts and prodrugs thereof as described herein for use in the treatment or prophylaxis of an HIV infection in a host, especially in individuals diagnosed as having an HIV infection or being at risk for becoming infected by HIV;

phenylindoles and their pharmaceutically acceptable salts and prodrugs thereof as described herein for use in the manufacture of a medicament for the treatment or prophylaxis of an HIV infection in a host, especially in individuals diagnosed as having an HIV infection or being at risk for becoming infected by HIV;

phenylindoles and their pharmaceutically acceptable salts and prodrugs thereof as described herein for use in the treatment or prophylaxis of an HIV infection, which is resistant to one or more reverse transcriptase inhibitors, in a host;

phenylindoles and their pharmaceutically acceptable salts and prodrugs thereof as described herein for use in the manufacture of a medicament for the treatment or prophylaxis of an HIV infection, which is resistant to one or more reverse transcriptase inhibitors, in a host;

phenylindoles and their pharmaceutically acceptable salts and prodrugs thereof as described herein for use in the treatment or prophylaxis of an HIV infection as a form of salvage therapy in a host, especially in individuals diagnosed as having an HIV infection or being at risk for becoming infected by HIV;

phenylindoles and their pharmaceutically acceptable salts and prodrugs thereof as described herein for use in the manufacture of a medicament for the treatment or prophylaxis of an HIV infection as a form of salvage therapy in a host, especially in individuals diagnosed as having an HIV infection or being at risk for becoming infected by HIV;

phenylindoles and their pharmaceutically acceptable salts and prodrugs thereof as described herein for use in the treatment or prophylaxis of an HIV infection that is resistant to one or more reverse transcriptase inhibitors due to a reverse transcriptase mutation, such as lysine 103→asparagine and/or tyrosine 181→cysteine, in a host, especially in individuals diagnosed as having an HIV infection or being at risk for becoming infected by HIV;

phenylindoles and their pharmaceutically acceptable salts and prodrugs thereof as described herein for use in the manufacture of a medicament for the treatment or prophylaxis of an HIV infection that is resistant to one or more reverse transcriptase inhibitors due to a reverse transcriptase mutation, such as lysine 103→asparagine and/or tyrosine 181→cysteine, in a host, especially in individuals diagnosed as having an HIV infection or being at risk for becoming infected by HIV;

processes for the preparation of phenylindoles, as described in more detail below;

processes for the preparation of phenylindoles substantially isolated from other chemical entities;

pharmaceutical compositions comprising an effective anti-HIV treatment amount of a phenylindole or its pharmaceutically acceptable salt or prodrug thereof together with a pharmaceutically acceptable carrier or diluent;

pharmaceutical compositions comprising an effective anti-HIV treatment amount of a phenylindole or its pharmaceutically acceptable salt or prodrug thereof in combination with one or more other anti-HIV agent, optionally with a pharmaceutically acceptable carrier or diluent;

pharmaceutical compositions for the treatment or prophylaxis of an HIV infection in a host comprising an effective anti-HIV treatment amount of a phenylindole or its pharmaceutically acceptable salt or prodrug thereof, optionally in combination with one or more other anti-HIV agent, optionally with a pharmaceutically acceptable carrier or diluent;

pharmaceutical compositions for the treatment or prophylaxis of an HIV infection, which is resistant to one or more reverse transcriptase inhibitors, in a host comprising an effective anti-HIV treatment amount of a phenylindole or its pharmaceutically acceptable salt or prodrug thereof, optionally in combination with one or more other anti-HIV agent, optionally with a pharmaceutically acceptable carrier or diluent;

pharmaceutical compositions for the treatment or prophylaxis of an HIV infection in a host as a form of salvage therapy comprising an effective anti-HIV treatment amount of a phenylindole or its pharmaceutically acceptable salt or prodrug thereof, optionally in combination with one or more other anti-HIV agent, optionally with a pharmaceutically acceptable carrier or diluent;

pharmaceutical compositions for the treatment or prophylaxis of an HIV infection, which is resistant to one or more reverse transcriptase inhibitors due to a reverse transcriptase mutation, such as lysine 103→asparagine and/or tyrosine 181→cysteine, in a host comprising an effective anti-HIV treatment amount of a phenylindole or its pharmaceutically acceptable salt or prodrug thereof, optionally in combination with one or more other anti-HIV agent, optionally with a pharmaceutically acceptable carrier or diluent;

methods for the treatment or prophylaxis of an HIV infection in a host comprising administering to said host an effective anti-HIV treatment amount of a phenylindole or its pharmaceutically acceptable salt or prodrug thereof, optionally in combination and/or alternation with one or more other anti-HIV agent, optionally with a pharmaceutically acceptable carrier or diluent;

methods for the treatment or prophylaxis of an HIV infection, which is resistant to one or more reverse transcriptase inhibitors, in a host comprising administering to said host an effective anti-HIV treatment amount of a phenylindole or its pharmaceutically acceptable salt or prodrug thereof, optionally in combination and/or alternation with one or more other anti-HIV agent, optionally with a pharmaceutically acceptable carrier or diluent;

methods for the treatment or prophylaxis of an HIV infection in a host as a form of salvage therapy comprising administering to said host an effective anti-HIV treatment amount of a phenylindole or its pharmaceutically acceptable salt or prodrug thereof, optionally in combination and/or alternation with one or more other anti-HIV agent, optionally with a pharmaceutically acceptable carrier or diluent;

methods for the treatment or prophylaxis of an HIV infection, which is resistant to one or more reverse transcriptase inhibitors due to a reverse transcriptase mutation, such as lysine 103→asparagine and/or tyrosine 181→cysteine, in a host comprising administering to said host an effective anti-HIV treatment amount of a phenylindole or its pharmaceutically acceptable salt or prodrug thereof, optionally in combination and/or alternation with one or more other anti-HIV agent, optionally with a pharmaceutically acceptable carrier or diluent;

use of a phenylindole or its pharmaceutically acceptable salt or prodrug thereof, optionally in combination and/or alternation with one or more other anti-HIV agent, optionally with a pharmaceutically acceptable carrier or diluent for the treatment or prophylaxis of an HIV infection in a host;

use of a phenylindole or its pharmaceutically acceptable salt or prodrug thereof, optionally in combination and/or alternation with one or more other anti-HIV agent, optionally with a pharmaceutically acceptable carrier or diluent for the treatment or prophylaxis of an HIV infection, which is resistant to one or more reverse transcriptase inhibitors, in a host;

use of a phenylindole or its pharmaceutically acceptable salt or prodrug thereof, optionally in combination and/or alternation with one or more other anti-HIV agent, optionally with a pharmaceutically acceptable carrier or diluent for the treatment or prophylaxis of an HIV infection in a host as a form of salvage therapy;

use of a phenylindole or its pharmaceutically acceptable salt or prodrug thereof, optionally in combination and/or alternation with one or more other anti-HIV agent, optionally with a pharmaceutically acceptable carrier or diluent for the treatment or prophylaxis of an HIV infection, which is resistant to one or more reverse transcriptase inhibitors due to a reverse transcriptase mutation, such as lysine 103→asparagine and/or tyrosine 181→cysteine, in a host;

use of a phenylindole or its pharmaceutically acceptable salt or prodrug thereof, optionally in combination and/or alternation with one or more other anti-HIV agent, optionally with a pharmaceutically acceptable carrier or diluent in the manufacture of a medicament for the treatment or prophylaxis of an HIV infection in a host;

use of a phenylindole or its pharmaceutically acceptable salt or prodrug thereof, optionally in combination and/or alternation with one or more other anti-HIV agent, optionally with a pharmaceutically acceptable carrier or diluent in the manufacture of a medicament for the treatment or prophylaxis of an HIV infection, which is resistant to one or more reverse transcriptase inhibitors, in a host;

use of a phenylindole or its pharmaceutically acceptable salt or prodrug thereof, optionally in combination and/or alternation with one or more other anti-HIV agent, optionally with a pharmaceutically acceptable carrier or diluent in the manufacture of a medicament for the treatment or prophylaxis of an HIV infection in a host as a form of salvage therapy;

use of a phenylindole or its pharmaceutically acceptable salt or prodrug thereof, optionally in combination and/or alternation with one or more other anti-HIV agent, optionally with a pharmaceutically acceptable carrier or diluent in the manufacture of a medicament for the treatment or prophylaxis of an HIV infection, which is resistant to one or more reverse transcriptase inhibitors due to a reverse transcriptase mutation, such as lysine 103→asparagine and/or tyrosine 181→cysteine, in a host; and any or all of the foregoing in which the host is a human.

I. Active Compounds of the Present Invention

In a first embodiment of the present invention, the compound can be represented generally by the following chemical Formula I:

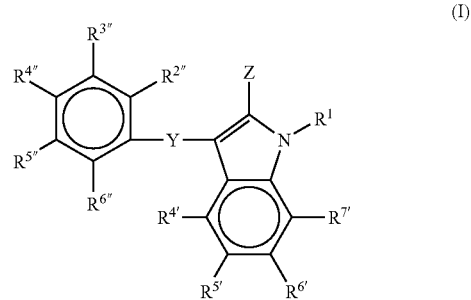

or a pharmaceutically acceptable salt or prodrug thereof, wherein (a) $R^1$ is hydrogen; acyl; —$C_{1-3}$ alkyl; —C(=W)H; —C(=W)$R^2$; —C(=W)OH; —C(=W)O$R^2$; —C(=W)S$R^2$; —C(=W)NH$_2$; —C(=W)NH$R^2$; —C(=W)N$R^2R^3$; —C(=W)NHN($R^2$)($R^3$); —C(=W)N($R^2$)NH($R^3$); —C(=W)NH—(CH$_2$)$_p$-(amino acid residue) or —(CH$_2$)$_p$-(amino acid residue);

(b) $R^{4'}$, $R^{5'}$, $R^{6'}$, $R^{7'}$, $R^{2''}$, $R^{3''}$, $R^{4''}$, $R^{5''}$ and $R^{6''}$ are each independently H, F, Cl, Br or I; —NO$_2$; —CN; —OH; —O$R^2$; —S$R^2$; —NH$_2$; —NH$R^2$; —N$R^2R^3$; —NH—SO$_2$—$C_{1-3}$alkyl; —N($R^2$)—SO$_2$—$C_{1-3}$alkyl; —NH—CO—$C_{1-3}$alkyl; —N($R^2$)—CO—$C_{1-3}$alkyl; optionally substituted or unsubstituted, branched or unbranched alkyl, alkenyl or alkynyl, CF$_3$, —C$R^2R^2$—S(O)$_n$—$R^3$, —C$R^2R^2$NH$_2$, —C$R^2R^2$NH$R^2$, —C$R^2R^2$N$R^2R^3$ and —C$R^2R^2$—C(=W)$R^2$; optionally substituted or unsubstituted acyl; —C(=W)H; —C(=W)$R^2$; —C(=W)O$R^2$; —C(=W)S$R^2$; —C(=W)NH$_2$; —C(=W)NH$R^2$; —C(=W)—N$R^2R^3$; —C(=W)NH (CH$_2$)$_p$-(amino acid residue), an amino acid residue or —(CH$_2$)$_p$(amino acid residue); wherein if $R^{5'}$ is hydrogen, F, Cl, I, Br, —NO$_2$, —CN, —O$R^2$, —N$R^2R^2$, —NHSO$_2$—$C_{1-3}$alkyl or —NHCO—$C_{1-3}$alkyl, then at least one of $R^{4'}$, $R^{6'}$ and $R^{7'}$ is not hydrogen or alternatively, wherein at least two of $R^{4'}$, $R^{5'}$, $R^{6'}$, $R^{7'}$ are not hydrogen;

(c) Z is optionally substituted or unsubstituted acyl; amide; hydrazine; —C(=W)NH$R^2$; —C(=W)N($R^2$)($R^3$); —C(=W)N($R^2$)—C(=W)NH$_2$; —C(=W)—N($R^3$)—C(=W)NH$_2$; —C(=W)NH$R^2$(—$R^3$)—C(=W)NH$_2$; —C(=W)NH$R^2$(—$R^3$)—C(=W)NH—$R^2$—C(=W)OH; —C(=W)NH$R^2$(—$R^3$)—C(=W)NH—$R^2$—C(=W)NH$_2$; —C(=W)NH$R^2$—C(=W)NH—$R^2$—C(=W)OH; —C(=W)NH$R^2$—C(=W)NH—$R^2$—C(=W)NH$_2$; —C(=W)NH$R^2$(—$R^3$)—C(=W)NH—$R^3$; —C(=W)NH—$R^3$; —C(=W)—$R^2$—(CH$_2$)$_p$-A-C(=W)—NH$_2$; an amino acid residue; —C(=W)N$R^2$(CH$_2$)$_p$-(amino acid residue), —C(=W)N$R^2$(CH$_2$)$_p$-(amino acid residue)-(C[=W]—NH$_2$); —C(=W)N$R^2$(CH$_2$)$_p$-(amino acid residue)-A-(C[=W]—NH$_2$); —C(=W)—NH—NH($R^2$); —C(=W)—N$R^2$—CH—(C[=W]NH$_2$)(CH$_2$—C[=W]—O—CH$_2$-aryl); —C(=W)—NH—CH(C[=W]NH$_2$)—(CH$_2$—C[=W]—O—CH$_2$-aralkyl); —C(=W)N$R^2$—C(=W)$R^3$; —C(=W)$R^3$; —C(=W)O$R^3$; —C(=W)—O$R^2$; —C(=W)SR; —C(=W)S$R^2$; —C(=W)—NH—NH—$R^2$OH; —C(=W)—NH—N($R^2$)($R^3$); —C(=W)—NH—N($R^2$)—CH($R^2$)—C(=W)$R^2$; —C(=W)—N($R^2$)—C(=W)$R^3$; —C(=W)—N($R^2$)—N($R^2$)—C(=W)$R^3$;

—C(=W)—R²—NH—C(=W)R²; —C(=W)—R²—C(=W)R³; —C(=W)—R³; —C(=W)—R²—NH—C(=W)OR; —C(=W)—R²—C(=W)R²; —C(=W)R³R²; —C(=W)—R²—W—R³; —C(=W)—NH—R²—R⁸—R³; —C(=W)—NH—NH—R²(R³)—R⁸—NH₂; —C(=W)—NH—R³(R⁸—NH₂); —C(=W)—NH—R²R³(R⁸—NH₂); —C(=W)—NH—R³(R²R⁸—NH₂); —C(=W)—NH—NH—CH₂—C(=W)R²; —C(=W)—NH—(CH₂)ₚ—NH—C(=W)-A-C(=W)—R²; —C(=W)—R²—(CH₂)ₚ—C(=W)-A-R³—C(=W)—NH₂; or —C(=W)—R²—CH₂-A-R³;

(d) Y is O, S or S(O)ₙ;
(e) each W is independently O, S, NH, or NR²;
(f) each R² is independently hydrogen or an optionally substituted or unsubstituted, branched or unbranched lower alkyl, alkenyl, alkynyl, alkylene, alkenylene or alkynylene; acyl; hydroxy; alkoxy; substituted or unsubstituted aryl; substituted or unsubstituted arylene; substituted or unsubstituted aralkyl; —CF₃; —NH₂; —NH—; —CH₂—S(O)ₙR³; —C(alkyl)₂-S(O)ₙR³; —CH(alkyl)-S(O)ₙR³; —CH(alkyl)NH₂; —C(alkyl)₂-NH₂; —CH₂—NH(alkyl); —C(alkyl)₂-NH(alkyl); —CH(alkyl)-NH(alkyl); —CH₂—NHR³; —CH₂N(alkyl)R³; —CH₂N(alkyl)₂R³; —CH(alkyl)-NHR³; —CH(alkyl)-N(alkyl)R³; —C(alkyl)₂-NHR³; —C(alkyl)₂-N(alkyl)R³; —CH₂—C(=W)H; —CH₂—C(=W)alkyl; —CH(alkyl)-C(=W)H; —CH(alkyl)-C(=W)alkyl; —(CH₂)ₚOH; —C(alkyl)₂-C(=W)H; —C(alkyl)₂-C(=W)alkyl; —CH(alkenyl)-S(O)ₙR³; —CH₂NH₂; —CH(alkenyl)NH₂; —C(alkenyl)₂-NH₂; —CH₂—NH(alkenyl); —C(alkenyl)₂-NH(alkenyl); —CH(alkenyl)-NH(alkenyl); —CH₂—NHR³; —CH₂—N(alkenyl)R³; —CH(alkenyl)-NHR³; —CH(alkenyl)-N(alkenyl)R³; —C(alkenyl)₂-NHR³; —C(alkenyl)₂-N(alkenyl)R³; —CH₂—C(=W)H; —CH₂—C(=W)alkenyl; —CH(alkenyl)-C(=W)H; —CH(alkenyl)-C(=W)alkenyl; —C(alkenyl)₂-C(=W)H; —C(alkenyl)₂-C(=W)alkenyl; —CH(alkynyl)-S(O)ₙR³; —CH(alkynyl)-NH₂; —C(alkynyl)₂-NH₂; —CH₂—NH(alkynyl); —C(alkynyl)₂-NH(alkynyl); —CH(alkynyl)-NH(alkynyl); —CH₂—NHR³; —CH₂—N(alkynyl)R³; —CH(alkynyl)-NHR³; —CH(alkynyl)-N(alkynyl)R³; —C(alkynyl)₂-NHR³; —C(alkynyl)₂-N(alkynyl)R³; —CH₂—C(=W)alkynyl; —CH(alkynyl)-C(=W)H; —CH₂—C(=W)H; —CH(alkynyl)-C(=W)alkynyl; —C(alkynyl)₂-C(=W)H; —C(alkynyl)₂-C(=W)alkynyl; —CH(alkoxy)-S(O)ₙR³; —CH(alkoxy)-NH₂; —C(alkoxy)₂-NH₂; —CH₂—NH(alkoxy); —C(alkoxy)₂-NH(alkoxy); —CH(alkoxy)-NH(alkoxy); —CH₂—NHR³; —CH₂—N(alkoxy)R³; —CH(alkoxy)-NHR³; —CH(alkoxy)-N(alkoxy)R³; —C(alkoxy)₂-NHR³; —C(alkoxy)₂-N(alkoxy)R³; —CH₂—C(=W)H; —CH₂C(=W)alkoxy; —CH(alkoxy)-C(=W)H; —CH(alkoxy)-C(=W)alkoxy; —C(alkoxy)₂-C(=W)H; —C(alkoxy)₂-C(=W)alkoxy; —CH(CF₃)—S(O)ₙR³; —CH(CF₃)—NH₂; —C(CF₃)₂—NH₂; —CH₂—NH(CF₃); —C(CF₃)₂—NH(CF₃); —CH(CF₃)—NH(CF₃); —CH₂—NHR³; —CH₂—N(CF₃)R³; —CH(CF₃)—NHR³; —CH(CF₃)—N(CF₃)R³; —C(CF₃)₂—NHR³; —C(CF₃)₂—N(CF₃)R³; —CH₂C(=W)H; —CH₂—C(=W)CF₃; —CH(CF₃)—C(=W)H; —CH(CF₃)—C(=W)CF₃; —C(CF₃)₂—C(=W)H; —C(CF₃)₂—C(=W)CF₃; —CH(NH)—S(O)ₙR³; —CH₂—NH—NH₂; —CH(NH)—NH(NH₂); —CH₂—NHR³; —CH₂—N(NH)R³; —CH(NH₂)—NHR³; —CH(NH₂)—N(NH₂)R³; —CH₂—C(=W)NH₂; —CHR²—C(=W)H; —CH₂—C(=W)H; —CH(NH₂)—C(=W)NH₂; —CH(NH₂)—NH₂; —CH₂—NH(NH₂); —CH₂—NHR³; —CH₂—N(NH₂)R³; —CH(NH₂)—NHR³; —CH(NH₂)—N(NH₂)R³; —CH₂—C(=W)H; —CH₂—C(=W)NH₂; —CH(NH₂)—C(=W)H; or —CH(NH₂)—C(=W)NH₂;

(g) each R³ is independently hydrogen; optionally substituted or unsubstituted, branched or unbranched alkyl, alkenyl, alkynyl, alkylene, alkenylene or alkynylene; CF₃; CN; amino; —C(R²²)(R²²)—S(O)ₙ—NH₂; —C(R²²)(R²²)—S(O)ₙ—CF₃; —C(R²²)(R²²)—NH₂, —C(R²²)(R²²)—NHR²², C(R²²)(R²²)—NR²²(alkyl); —C(R²²)(R²²)—NR²²(alkenyl); —C(R²²)(R²²)—NR²²(alkynyl); —C(R²²)(R²²)—NR²²(CF₃); and —C(R²²)(R²²)—C(=W)R²²; optionally substituted or unsubstituted aryl and arylene; optionally substituted or unsubstituted heterocycle; optionally substituted or unsubstituted cycloalkyl; optionally substituted or unsubstituted alkylaryl, optionally substituted or unsubstituted alkylheterocycle, optionally substituted or unsubstituted aralkyl and aralkylene, optionally substituted or unsubstituted heterocycle-alkyl;
(h) each R²² is independently hydrogen or an optionally substituted or unsubstituted, branched or unbranched lower alkyl, alkenyl, alkynyl; acyl; hydroxy; alkoxy; substituted or unsubstituted aryl; substituted or unsubstituted arylene; substituted or unsubstituted aralkyl; amine, alkylamine, alkylsulfonyl, —CF₃; —NH₂; alkylacyl; amide; alkylamide;
(i) each R⁸ is independently —C(=O) or —S(O)ₙ;
(j) each n is independently 0, 1 or 2;
(k) each p is independently 0, 1, 2, 3, 4, or 5;
(l) A is a disubstituted spacer selected from the group consisting of alkylene which optionally may have one or more heteroatoms, aryl, cycloalkyl or heterocyclyl functions in the chain; alkenylene which optionally may have one or more heteroatoms, aryl, cycloalkyl or heterocyclyl functions in the chain; and optionally substituted aryl, cycloalkyl, and heterocyclyl;
(m) R is selected from the group consisting of H, aryl, alkoxy, substituted or unsubstituted, branched or unbranched alkyl, alkenyl, alkynyl, cycloalkyl, heterocyclyl, and aralkyl;
wherein if one or more of the optionally substituted, branched or unbranched alkyl, alkenyl, alkynyl, lower alkyl, lower alkenyl or lower alkynyl, acyl, aryl, heterocycle, alkaryl, alkheterocycle, arylalkyl or alkylheterocycle substituents is substituted, then preferably it is substituted with one or more halogen, —OH, —OR², —SR², carboxylic acid, carboxylic acid ester, oxime defined herein as —CH=N—OH, hydrazine defined herein as —NH—NH₂, —C(=W)H, —C(=W)R², —C(=W)OH, —C(=W)OR², —C(=W)OR³; —C(=W)SR¹, —C(=W)NH₂, -alkylene-C(=W)NH₂, —C(=W)NHR², —C(=W)—NR²R³, —NR²R², —NR²R³; —NH—S(O)ₙR³; —NR²—S(O)ₙR³; —NH—CO—C₁₋₃alkyl; —NR²—CO—C₁₋₃alkyl; —S(O)ₙR³; —C₁₋₄ alkoxy; —C₁₋₃-thioether; or an amino acid residue such as —NH(CH₂)ₚ-(amino acid residue) or —C(=W)NH(CH₂)ₚ-(amino acid residue).

In a preferred embodiment, Y is SO₂. In another preferred embodiment, Z is an amide or acyl-hydrazine function.

In an alternative embodiment, the hydrogen attached to the indole nitrogen can be replaced with acyl, lower alkyl, aryl, alkaryl or aralkyl.

In a second embodiment the invention provides a phenylindole represented generally by formula (I) above, and methods of using such phenylindoles in the treatment of HIV, wherein:
(a) $R^1$ is hydrogen;
(b) $R^{4'}$, $R^{5'}$, $R^{6'}$, $R^{7'}$, are independently selected from the group consisting of hydrogen, halogen, —$NO_2$, —CN, —$OR^2$, —$NR^2R^2$, —$NHSO_2$—$C_{1-3}$alkyl, —NHCO—$C_{1-3}$alkyl, oxime (—CH=N—OH), hydrazine (—NH—$NH_2$), $C_{1-3}$ alkyl and alkenyl optionally substituted with one or more of —OH, —SR, C(=W)H, C(=W)OH, halogen, $NR^2R^2$, $C_{1-3}$ alkoxy, and $C_{1-3}$ thioether; wherein any three of $R^{4'}$, $R^{5'}$, $R^{6'}$, or $R^{7'}$ simultaneously must be hydrogen;
(c) $R^{2''}$, $R^{3''}$, $R^{4''}$, $R^{5''}$, and $R^{6''}$, are independently selected from the group consisting of hydrogen, halogen, —$NO_2$, —CN, —$OR^2$, —$NHSO_2$—$C_{1-3}$alkyl, —NHCO—$C_{1-3}$alkyl, oxime, hydrazine, —$C_{1-5}$ alkyl and alkenyl optionally substituted with one or more of —OH, C(=W)H, C(=W)OH, halogen, $NR^2R^2$, $C_{1-5}$ thioether, or $C_{1-5}$ alkoxy, —$C_{1-5}$ alkoxy, —OH, and —$NR^2R^2$;
(d) Z is selected from the group consisting of —C(=W)N($R^3$)C(=W)$NH_2$; —C(=W)—NH—CH(—C[=W]$NH_2$)(—$CH_2$—C[=W]—O—$CH_2$-aryl); —C(=W)—NH—CH(—C[=W]$NH_2$)(—$CH_2$—C[=W]—O—$CH_2$-aralkyl); —C(=W)$NHR^2$(—$R^3$)—C(=W)NH—$R^2$—C(=W)OH; —C(=W)$NHR^2$(—$R^3$)—C(=W)NH—$R^2$—C(=W)$NH_2$; —C(=W)$NHR^2$—C(=W)NH—$R^2$—C(=W)OH; —C(=W)$NHR^2$—C(=W)NH—$R^2$—C(=W)$NH_2$; —C(=W)$NHNH_2$; —C(=W)NH—$CH_2$—C(=W)$NHNH_2$; —C(=W)NH—CH($R^2$)—C(=W)$NH_2$; —C(=W)$NR^2$—C(=W)$R^3$; —C(=W)SR; —C(=W)$SR^2$; optionally substituted or unsubstituted, branched or unbranched $C_{4-12}$ alkylene, alkenylene or alkynylene; —C(=W)—NH—N($R^2$)($R^3$); —C(=W)$R^2$—$CH_2$—$R^2$—CH($CH_3$)—C(=W)—OH; CH($CH_3$)C(=W)—OH; —C(=W)—NH—N($R^2$)—CH($R^2$)—C(=W)$R^2$; —C(=W)—N($R^2$)—C(=W)$R^3$; —C(=W)CH=CH—C(=W)$R^2$; —C(=W)$R^2$($CH_2$)_2—C(=W)$R^2$; —C(=W)—$R^2$—$CH_2$-A-C(=W)$R^2$; —C(=W)$R^2$—C(=W)—$OR^3$; —C(=W)—$R^2$—NH—C(=W)$OR^3$; —C(=W)$OR^3$—NH—C(=W)—$R^2$; —C(=W)—N($R^8$)—N($R^2$)—N($R^2$)($R^3$); —C(=W)—N($R^2$)—N($R^2$)—C(=W)$R^3$; —C(=W)—N(N[$R^2$][$R^3$])—N[$R^2$][$R^3$])$R^3$; —C(=W)$R^2$—C(=W)NH; —C(=W)$R^2$—$SR^3$; —C(=W)—CH($R^2$)—C(=NH)$R^2$; —C(=W)—NH—($CH_2$)_p—NH—C(=W)-A-C(=W)—$R^2$; —C(=W)—$R^2$—($CH_2$)_p—C(=W)-A-$R^3$—C(=W)—$NH_2$; —C(=W)—NH—CH(—[$CH_2$]_p—NH—C[=W]$R^2$)—(—C[=W]—$NH_2$); —C(=W)—NH—CH(—[$CH_2$]_p—C[=W]—$R^2$)(—C[=W]—$NH_2$); —C(=W)—NH—CH(—[$CH_2$]_p—$R^3$)(—C[=W]—$NH_2$); —C(=W)—NH—CH(—[$CH_2$]_p—OH)(—C[=W]—$NH_2$); —C(=W)—NH—CH(—C[=W]—$NH_2$)(—C[=W]—$NH_2$); —C(=W)—NH—CH(—[$CH_2$]_p—NH—C[=W]O—$CH_2$—$R^3$)(—C[=W]—$NH_2$); —C(=W)—$R^2$—CH(—$R^2$—C[=W]—$NH_2$)(—C[=W]—$NH_2$); —C(=W)—NH—CH(—CH—$R^2$—OH)—(—C[=W]—$NH_2$); —C(=W)—NH—CH(—$R^2$)—C[=W]—$NH_2$); —C(=W)—NH—CH(—$R^2$—C[=W]—$NH_2$)(—C[=W]—$NH_2$); —C(=W)—NH—CH(—$R^2$—$SCH_3$)—(—C[=W]—$NH_2$); —C(=W)—NH—NH—CH($R^3$)—C(=W)$R^2$; —C(=W)$NHR^2$(—$R^3$)—C(=W)$NH_2$; —C(=W)$NHR^2$(—$R^3$)—C(=W)NH—$R^2$—C(=W)OH; —C(=W)—$NHR^2$(—$R^3$)—C(=W)NH—$R^2NH_2$; —C(=W)$NHR^2$(—$R^3$)—C(=W)NH—$R^3$; —C(=W)—$R^2$—($CH_2$)_p-A-C(=W)—$NH_2$; —C(=W)NH—$R^3$; —C(=W)—NH—$R^2$—$R^8$—$R^3$; —C(=W)—NH—NH—$R^2$($R^3$)—$R^8$—$NH_2$; —C(=W)—NH—$R^3$($R^8$—$NH_2$); —C(=W)—NH—$R^2R^3$($R^8$—$NH_2$); —C(=W)—NH—$R^3$($R^2R^8$—$NH_2$); and —C(=W)—NH—CH—(—C[=N]—$NH_2$)(—C[=W]—$NH_2$);
(e) Y is —S(O)_n— or —O—, in which n is 0, 1 or 2;
(f) W is O, S, —NH or —$NR^2$;
(g) each $R^2$ is independently hydrogen or an optionally substituted or unsubstituted, branched or unbranched lower alkyl, alkenyl, alkynyl, alkylene, alkenylene or alkynylene; acyl; hydroxy; alkoxy; substituted or unsubstituted aryl; substituted or unsubstituted aralkyl; —$CF_3$; —$NH_2$; —NH—; —$CH_2$—S(O)_n$R^3$; —C(alkyl)_2-S(O)_n$R^3$; —CH(alkyl)-S(O)_n$R^3$; —CH(alkyl)$NH_2$; —C(alkyl)_2-$NH_2$; —$CH_2$—NH(alkyl); —C(alkyl)_2-NH(alkyl); —CH(alkyl)-NH(alkyl); —$CH_2$—$NHR^3$; —$CH_2$N(alkyl)$R^3$; —$CH_2$N(alkyl)$R^3$; —CH(alkyl)-$NHR^3$; —CH(alkyl)-N(alkyl)$R^3$; —C(alkyl)_2-$NHR^3$; —C(alkyl)_2-N(alkyl)$R^3$; —$CH_2$—C(=W)H; —$CH_2$—C(=W)alkyl; —CH(alkyl)-C(=W)H; —CH(alkyl)-C(=W)alkyl; —($CH_2$)_pOH; —C(alkyl)_2-C(=W)H; —C(alkyl)_2-C(=W)alkyl; —CH(alkenyl)-S(O)_n$R^3$; —$CH_2NH_2$; —CH(alkenyl)$NH_2$; —C(alkenyl)_2-$NH_2$; —$CH_2$—NH(alkenyl); —C(alkenyl)_2-NH(alkenyl); —CH(alkenyl)-NH(alkenyl); —$CH_2$—$NHR^3$; —$CH_2$—N(alkenyl)$R^3$; —CH(alkenyl)-$NHR^3$; —CH(alkenyl)-N(alkenyl)$R^3$; —C(alkenyl)_2-$NHR^3$; —C(alkenyl)_2-N(alkenyl)$R^3$; —$CH_2$—C(=W)H; —$CH_2$—C(=W)alkenyl; —CH(alkenyl)-C(=W)H; —CH(alkenyl)-C(=W)alkenyl; —C(alkenyl)_2-C(=W)H; —C(alkenyl)_2-C(=W)alkenyl; —CH(alkynyl)-S(O)_n$R^3$; —CH(alkynyl)-$NH_2$; —C(alkynyl)_2-$NH_2$; —$CH_2$—NH(alkynyl); —C(alkynyl)_2-NH(alkynyl); —CH(alkynyl)-NH(alkynyl); —$CH_2$—$NHR^3$; —$CH_2$—N(alkynyl)$R^3$; —CH(alkynyl)-$NHR^3$; —CH(alkynyl)-N(alkynyl)$R^3$; —C(alkynyl)_2-$NHR^3$; —C(alkynyl)_2-N(alkynyl)$R^3$; —$CH_2$—C(=W)H; —$CH_2$—C(=W)alkynyl; —CH(alkynyl)-C(=W)H; —CH(alkynyl)-C(=W)alkynyl; —C(alkynyl)_2-C(=W)H; —C(alkynyl)_2-C(=W)alkynyl; —CH(alkoxy)-S(O)_n$R^3$; —CH(alkoxy)-$NH_2$; —C(alkoxy)_2-$NH_2$; —$CH_2$—NH(alkoxy); —C(alkoxy)_2-NH(alkoxy); —CH(alkoxy)-NH(alkoxy); —$CH_2$—$NHR^3$; —$CH_2$—N(alkoxy)$R^3$; —CH(alkoxy)-$NHR^3$; —CH(alkoxy)-N(alkoxy)$R^3$; —C(alkoxy)_2-$NHR^3$; —C(alkoxy)_2-N(alkoxy)$R^3$; —$CH_2$—C(=W)H; —$CH_2$C(=W)alkoxy; —CH(alkoxy)-C(=W)H; —CH(alkoxy)-C(=W)alkoxy; —C(alkoxy)_2-C(=W)H; —C(alkoxy)_2-C(=W)alkoxy; —CH($CF_3$)—S(O)_n$R^3$; —CH($CF_3$)—$NH_2$; —C($CF_3$)_2—$NH_2$; —$CH_2$—NH($CF_3$); —C($CF_3$)_2—NH($CF_3$); —CH($CF_3$)—NH($CF_3$); —$CH_2$—$NHR^3$; —$CH_2$—N($CF_3$)$R^3$; —CH($CF_3$)—$NHR^3$; —CH($CF_3$)—N($CF_3$)$R^3$; —C($CF_3$)_2—$NHR^3$; —C($CF_3$)_2—N($CF_3$)$R^3$; —$CH_2$C(=W)H; —$CH_2$—C(=W)$CF_3$; —CH($CF_3$)—C(=W)H; —CH($CF_3$)—C(=W)$CF_3$; —C($CF_3$)_2—C(=W)H; —C($CF_3$)_2—C(=W)$CF_3$; —CH(NH)—S(O)_n$R^3$; —$CH_2$—NH—$NH_2$; —CH($NH_2$)—NH($NH_2$); —$CH_2$—$NHR^3$; —$CH_2$—N(NH)$R^3$; —CH($NH_2$)—$NHR^3$; —CH($NH_2$)—N($NH_2$)$R^3$; —$CH_2$—C(=W)$NH_2$; —$CHR^2$—C(=W)H; —$CH_2$—C(=W)H; —CH($NH_2$)—C(=W)$NH_2$;

—CH(NH$_2$)—NH$_2$; —CH$_2$—NH(NH$_2$); —CH$_2$—NHR$^3$; —CH$_2$—N(NH$_2$)R$^3$; —CH(NH$_2$)—NHR$^3$; —CH(NH$_2$)—N(NH$_2$)R$^3$; —CH$_2$—C(=W)H; —CH$_2$—C(=W)NH$_2$; —CH(NH$_2$)—C(=W)H; or —CH(NH$_2$)—C(=W)NH$_2$;

(h) each R$^3$ is independently hydrogen; optionally substituted or unsubstituted, branched or unbranched alkyl, alkenyl, alkynyl, alkylene, alkenylene or alkynylene; CF$_3$; CN; amino; —C(R$^{22}$)(R$^{22}$)—S(O)$_n$—NH$_2$; —C(R$^{22}$)(R$^{22}$)S(O)$_n$—CF$_3$; —C(R$^{22}$)(R$^{22}$)—NH$_2$; —C(R$^{22}$)(R$^{22}$)—NHR$^{22}$, C(R$^{22}$)(R$^{22}$)—NR$^{22}$(alkyl); —C(R$^{22}$)(R$^{22}$)—NR$^{22}$(alkenyl); —C(R$^{22}$)(R$^{22}$)—NR$^{22}$(alkynyl); C(R$^{22}$)(R$^{22}$)—NR$^{22}$(CF$_3$); and —C(R$^{22}$)(R$^{22}$)—C(=W)R; optionally substituted or unsubstituted aryl and arylene; optionally substituted or unsubstituted heterocycle; optionally substituted or unsubstituted cycloalkyl; optionally substituted or unsubstituted alkylaryl, optionally substituted or unsubstituted alkylheterocycle, optionally substituted or unsubstituted aralkyl and aralkylene, optionally substituted or unsubstituted heterocycle-alkyl;

(i) each R$^{22}$ is independently hydrogen or an optionally substituted or unsubstituted, branched or unbranched lower alkyl, alkenyl, alkynyl; acyl; hydroxy; alkoxy; substituted or unsubstituted aryl; substituted or unsubstituted arylene; substituted or unsubstituted aralkyl; amine, alkylamine, alkylsulfonyl, —CF$_3$; —NH$_2$; alkylacyl; amide; alkylamide;

(j) A is a disubstituted spacer selected from the group consisting of alkylene which optionally may have one or more heteroatoms, aryl, cycloalkyl or heterocyclyl functions in the chain; alkenylene which optionally may have one or more heteroatoms, aryl, cycloalkyl or heterocyclyl functions in the chain; and optionally substituted aryl, cycloalkyl, and heterocyclyl;

(k) R is selected from the group consisting of H; aryl; alkoxy; optionally substituted, branched or unbranched alkyl, alkenyl, alkynyl, cycloalkyl, heterocyclyl, and aralkyl;

(l) each n is independently 0, 1 or 2;

(m) each p is independently 0, 1, 2, 3, 4 or 5, (n) wherein if one or more of the optionally substituted, branched or unbranched alkyl, alkenyl, alkynyl, lower alkyl, lower alkenyl or lower alkynyl, acyl, aryl, heterocycle, alkaryl, alkheterocycle, arylalkyl or alkylheterocycle substituents is substituted, then preferably it is substituted with one or more halogen, —OH, —OR$^2$, —SR$^2$, carboxylic acid, carboxylic acid ester, oxime defined herein as —CH=N—OH, hydrazine defined herein as —NH—NH$_2$, —C(=W)H, —C(=W)R$^2$, —C(=W)OH, —C(=W)OR$^2$, —C(=W)OR$^3$; —C(=W)SR$^2$, —C(=W)NH$_2$, —C(=W)NHR$^2$, —C(=W)—NR$^2$R$^3$, —NR$^2$R$^2$, —NR$^2$R$^3$; —NH—S(O)$_n$R$^3$; —NR$^2$—S(O)$_n$R$^3$; —NH—CO—C$_{1-3}$alkyl; —NR$^2$—CO—C$_{1-3}$alkyl; —S(O)$_n$R$^3$; —C$_{1-4}$ alkoxy; —C$_{1-3}$ thioether; or an amino acid residue such as —NH(CH$_2$)$_p$-(amino acid residue) or —C(=W)NH(CH$_2$)$_p$-(amino acid residue).

In a preferred embodiment, Y is SO$_2$. In another preferred embodiment, Z is an amide or acyl-hydrazine function.

In an alternative embodiment, the hydrogen attached to the indole nitrogen can be replaced with acyl, lower alkyl, aryl, alkaryl or aralkyl.

In a particular embodiment of the present invention, the phenylindole is a compound of the structure:

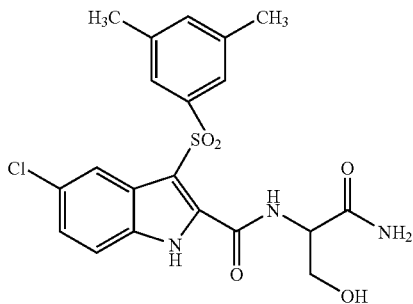

or a pharmaceutically acceptable salt or prodrug thereof.

In yet another particular embodiment of the present invention, the phenylindole is a compound of the structure:

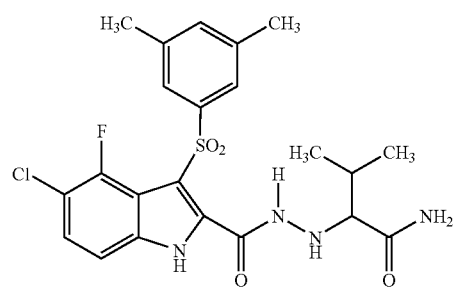

or a pharmaceutically acceptable salt or prodrug thereof.

In still another particular embodiment of the present invention, the phenylindole is a compound of the structure:

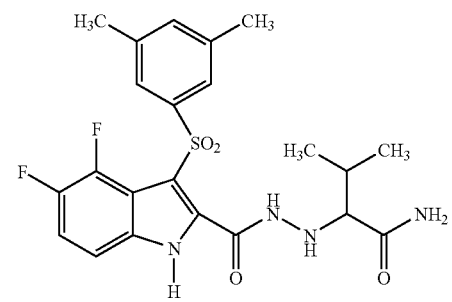

or a pharmaceutically acceptable salt or prodrug thereof.

In yet another particular embodiment of the present invention, the phenylindole is a compound of the structure:

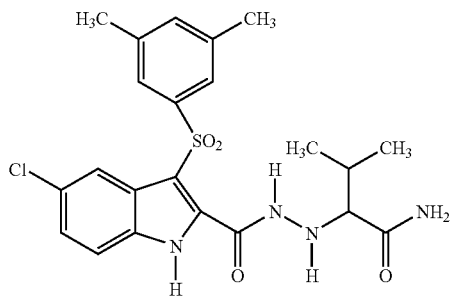

or a pharmaceutically acceptable salt or prodrug thereof.

In yet another particular embodiment of the present invention, the phenylindole is a compound of the structure:

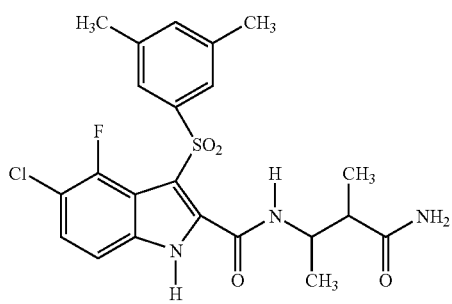

or a pharmaceutically acceptable salt or prodrug thereof.

In yet another particular embodiment of the present invention, the phenylindole is a compound of the structure:

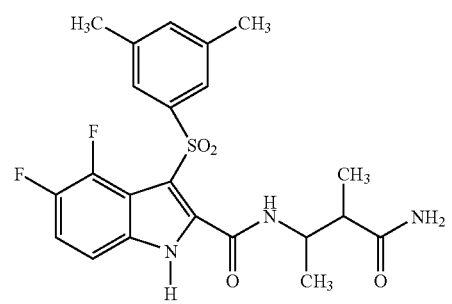

or a pharmaceutically acceptable salt or prodrug thereof.

In yet still another particular embodiment of the present invention, the phenylindole is a compound of the structure:

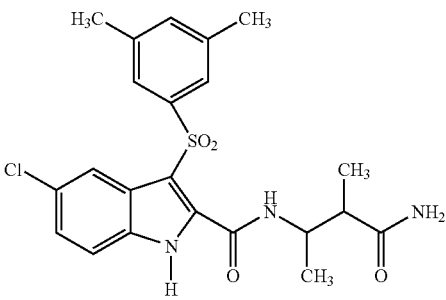

or a pharmaceutically acceptable salt or prodrug thereof.

The phenylindoles of this invention belong to a class of anti-HIV agents that may inhibit reverse transcriptase activity. These compounds can be assessed for their ability to inhibit reverse transcriptase activity in vitro according to standard screening methods.

In one embodiment the efficacy of the anti-HIV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or preferably, less than 10 micromolar in vitro.

In another embodiment, the active compound exhibits significant activity against drug-resistant forms of HIV, and thus exhibits decreased cross-resistance against currently approved antiviral therapies. The term significant activity against a drug resistant form of HIV means that a compound (or its prodrug or pharmaceutically acceptable salt) is active against the mutant strain with an $EC_{50}$ against the mutant strain of less than approximately 50, 25, 10 or 1 micromolar concentration. In a preferred embodiment, the non-nucleosides reverse transcriptase inhibitors (NNRTI) displays an $EC_{50}$ (in molar concentrations) in a mutant HIV strain of less than approximately 5, 2.5, 1 or 0.1 micromolar concentration. In one non limiting embodiment, the HIV mutant strain is a strain with a reverse transcriptase mutation at lysine 103→asparagine and/or tyrosine 181→cysteine.

In still another embodiment, the active compound can be administered in combination or alternation with another anti-HIV agent. In combination therapy, effective dosages of two or more agents are administered together, whereas during alternation therapy an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

II. Particular Sub-Embodiments of the Present Invention

In the first embodiment of the invention, the compounds are represented generally by the Formula I defined above wherein the variables are defined as follows:

(a) Z is optionally substituted or unsubstituted acyl; —C(=W)NHR$^2$; —C(=W)N(R$^2$)(R$^3$); —C(=W)N(R$^2$)—C(=W)NH$_2$; —C(=W)N(R$^3$)—C(=W)NH$_2$; an amino acid residue; —C(=W)NR$^2$(CH$_2$)$_p$-(amino acid residue); —C(=W)NR$^2$(CH$_2$)$_p$-(amino acid residue)-(C[=W]—NH$_2$); —C(=W)—NR$^2$(CH$_2$)$_p$-(amino acid residue)-A-(C[=W]—NH$_2$); —C(=W)—NH—NH(R$^2$); —C(=W)—NR$^2$—CH—(C[=W]NH$_2$)(CH$_2$—C[=W]—O—CH$_2$-aryl); —C(=W)—NH—CH(C[=W]R$^2$)(CH$_2$—C[=W]—O—CH$_2$-aralkyl); —C(=W)NR$^2$—C(=W)R$^3$; —C(=W)R$^3$; —C(=W)OR$^3$; —C(=W)—OR$^2$; —C(=W)SR; —C(=W)SR$^2$; —C(=W)—NH—NH—R$^2$OH; —C(=W)—NH—N(R$^2$)(R$^3$); —C(=W)—NH—N(R$^2$)—CH(R$^2$)—C(=W)R$^2$; —C(=W)—N(R$^2$)—C(=W)R$^3$; —C(=W)—N(R$^2$)—N(R$^2$)—C(=W)R$^3$; —C(=W)—R$^2$—NH—C(=W)R$^2$; —C(=W)—R$^2$—C(=W)R$^3$; —C(=W)—R$^2$—NH—C(=W)OR$^3$; —C(=W)—R$^2$—C(=W)R$^2$; —C(=W)R$^3$R$^2$; —C(=W)—R$^2$—W—R$^3$; —C(=W)—NH—NH—CH$_2$—C(=W)R$^2$; —C(=W)—NH—(CH$_2$)$_p$—NH—C(=W)-A-C(=W)—R$^2$; —C(=W)—R$^2$—(CH$_2$)$_p$—C(=W)-A-R$^3$—C(=W)—NH$_2$; —C(=W)—NH—NH—CH(R$^3$)—C(=W)R$^2$; —C(=W)NHR$^2$(—R$^3$)—C(=W)NH$_2$; —C(=W)—NHR$^2$(—R$^3$)—C(=W)NH—R$^2$—C(=W)OH; —C(=W)NHR$^2$(—R$^3$)—C(=W)NH—R$^2$NH$_2$; —C(=W)NHR$^2$(—R$^3$)—C(=W)NH—R$^3$; —C(=W)—R$^2$—(CH$_2$)$_p$-A-C(=W)—NH$_2$; —C(=W)NH—R$^3$; —C(=W)—NH—R$^2$—R$^8$—R$^3$; —C(=W)—NH—NH—R$^2$(R$^3$)—R$^8$—NH$_2$; —C(=W)—NH—R$^3$(R$^8$—NH$_2$); —C(=W)—NH—R$^2$R$^3$(R$^8$—NH$_2$); —C(=W)—NH—R$^3$(R$^2$R$^8$—NH$_2$); —C(=W)NHR$^2$(—R$^3$)—C(=W)NH—R$^2$—C(=W)OH; —C(=W)—NHR$^2$(—R$^3$)—C(=W)NH—R$^2$—C(=W)NH$_2$; —C(=W)NHR$^2$—C(=W)NH—R$^2$—C(=W)OH; —C(=W)NHR$^2$—C(=W)NH—R$^2$—C(=W)NH$_2$; or —C(=W)—R$^2$—CH$_2$-A-R$^3$;

(b) R$^2$ is hydrogen, or C$_{1-5}$ alkyl or alkylene, optionally substituted with —OH, NH$_2$, alkylamine, or dialkylamine;

(c) R$^3$ is (i) —NR$^2$R$^2$, or (ii) —(CH$_2$)$_m$C(=W)NR$^2$R$^2$, (iii) C$_{1-5}$ alkyl, C$_{1-5}$ alkylene, C$_{1-5}$ alkenyl, C$_{1-5}$ alkenylene, aryl, arylene, or heterocycle, substituted with one or more of C(=W)NR$^2$R$^2$, or (iv) a residue of an amino acid residue or (v) —NH(CH$_2$)$_p$-(amino acid residue);

(d) W is O, S, NH, or NR$^2$;

(e) p is 1, 2, 3, 4, or 5;

(f) R$^{4'}$, R$^{5'}$, R$^{6'}$, R$^{7'}$, are independently H, halo, —NO$_2$, —CN, —OR$^2$, —NR$^2$R$^2$, —NHSO$_2$—C$_{1-3}$alkyl, —NH-Q, —NHCO—C$_{1-3}$alkyl, —NH—O—C$_{1-3}$ alkyl, —NHOH, oxime, hydrazine, or C$_{1-3}$ alkyl or alkenyl optionally substituted with one or more of —OH, —SR, C(=W)H, C(=W)OH, halogen, NR$^2$R$^2$, C$_{1-3}$ alkoxy, or C$_{1-3}$ thioether, with the caveat that at least two of R$^{4'}$, R$^{5'}$, R$^{6'}$, R$^{7'}$ must not be H simultaneously;

(g) R$^{2''}$, R$^{3''}$, R$^{4''}$, R$^{5''}$, and R$^{6''}$, are independently (i) hydrogen, (ii) halogen, (iii) NO$_2$, (iv) —CN, (v) —OR$^2$, (vi) —NH—R$^8$—C$_{1-3}$alkyl, (vii) —NHCO—C$_{1-3}$alkyl, (viii) oxime, (ix) hydrazine, (x) —C$_{1-5}$ alkyl or alkenyl optionally substituted with one or more of —OH, —C(O)H, C(=W)OH, halogen, NR$^2$R$^2$, C$_{1-5}$ thioether, or C$_{1-5}$ alkoxy, (xi) —C$_{1-5}$ alkoxy, (xii) —OH, or (ix) —NR$^2$R$^2$;

(h) A is a disubstituted spacer selected from the group consisting of alkylene which optionally may have one or more heteroatoms, arylene, cycloalkyl or heterocyclyl in the chain; alkenylene which optionally may have one or more heteroatoms, arylene, cycloalkyl or heterocyclyl in the chain; and optionally substituted arylene, cycloalkyl, and heterocyclyl;

(i) R is H; aryl; alkoxy; optionally substituted, branched or unbranched alkyl, alkenyl, alkynyl; optionally substituted heterocyclyl, cycloalkyl or aralkyl; and (j) Y is —S(O)$_n$— or —O—, in which n is 0, 1, or 2.

A first series of preferred subembodiments of the first embodiment is defined when Z is defined as follows:

1) Z is C(=W)NR$^2$R$^3$, R$^2$ is hydrogen, and R$^3$ is NR$^2$R$^2$;
2) Z is C(=W)NR$^2$R$^3$, R$^2$ is hydrogen, and R$^3$ is NR$^2$R$^2$, or R$^2$ is C$_{1-5}$ alkyl optionally substituted with OH and R$^3$ is —NH$_2$;
3) Z is C(=W)NR$^2$R$^3$, R$^2$ is hydrogen, and R$^3$ is (CH$_2$)$_m$C(=W)NR$^2$R$^2$;
4) Z is C(=W)NR$^2$R$^3$, R$^2$ is hydrogen, and R$^3$ is alkyl substituted by substituted or unsubstituted aryl or heterocycle;
5) Z is C(=W)R$^3$, R$^3$ is a residue of an amino acid residue or —NH(CH$_2$)$_p$-(amino acid residue);
6) Z is —C(=W)NHNHC$_2$HSOH;
7) Z is —C(=W)NHCH$_2$C(=W)NH$_2$;
8) Z is —C(=W)NHCH$_2$CONHNH$_2$;
9) Z is —C(=W)NHCH$_2$CH$_2$-(2-NO$_2$-5-Me-imidazole);
10) Z is —C(=W)NHCH$_2$NHCH(CH$_3$)C(=W)OH;
11) Z is —C(=W)NHCH=CHC(=W)NH$_2$;
12) Z is —C(=W)NR$^2$R$^8$NR$^2$R$^3$, W is 0, R$^8$ is (=O), R$^2$ and R$^3$ are as defined above;
13) Z is —C(=W)NR$^2$NR$^2$—C(=W)R$^3$, W is S, R$^2$ is H or alkyl, and R$^3$ is aryl;
14) Z is —C(=W)N(—NR$^2$R$^3$)—N(—NR$^2$R$^3$)R$^3$, W is 0, R$^2$ is H, R$^3$ is R$^2$ or alkoxy;
15) Z is —C(=W)NHR$^2$C(=W)-Q, Q is a heterocycle and R$^2$ is as defined above;
16) Z is —C(=W)NR$^2$R$^3$, W is S, R$^2$ is as defined above, and R$^3$ is —OH;
17) Z is —COR$^2$—R$^3$, R$^2$ is amino and R$^3$ is a heterocycle;
18) Z is —C(=W)NH—NH—C(=W)R$^2$ where W is or S, and R$^2$ is NH$_2$;
19) Z is —C(=W)—R$^2$—CH-A-C(=W)NH$_2$ where W is O or S, and R$^2$ is NH;
20) Z is —C(=W)R$^2$CH-A-C(=W)H where W is O or S, A is alkylene, and R$^2$ is NH;
21) Z is —C(=W)R$^2$CH-A-C(=W)OH where W is O or S, A is heterocyclyl, and R$^2$ is NH;
22) Z is —C(=W)R$^2$CH-A-R$^3$ where W is O or S, R$^2$ is NH, A is aryl, and R$^3$ is CH$_3$;
23) Z is —C(=W)NHR$^2$C(=W)NH$_2$, where W is O or S, and R$^2$ is optionally substituted, branched chain alkyl;
24) Z is —C(=W)R$^2$R$^3$; W is O or S; R$^2$ is NH or alkyl; R$^3$ is NH$_2$;
25) Z is —C(=W)R$^2$—C(=W)OR$^3$ where R$^2$ and R$^3$ are as defined above;
26) Z is —C(=W)R$^2$—NH—C(=W)C$_{1-4}$ alkoxy where R$^2$ is as defined above;
27) Z is —C(=W)R$^2$C(=W) C$_{1-4}$ alkoxy where R$^2$ is as defined above;
28) Z is —C(=W)R$^2$ where R$^2$ is NH$_2$;

29) Z is —C(=W)R$^2$—NH—C(=W)OR$^3$ where R$^2$ and R$^3$ are as defined above;
30) Z is —C(=W)R$^2$—C(=W)R$^2$ where R$^2$ is as defined above;
31) Z is —C(=W)NHR$^2$ where R$^2$ is optionally substituted aryl, cycloalkyl or heterocyclyl ring;
32) Z is —C(=W)R$^2$—W—R$^3$ where R$^2$ and R$^3$ are as defined above;
33) Z is —C(=W)—NH—CH(R$^2$)—C(=W)—NH$_2$ where R$^2$ is as defined above;
34) Z is —C(=W)—NH—NH$_2$;
35) Z is —C(=W)—NH—NH(R$^2$);
36) Z is —C(=W)—NH—CH(C[=W]NH$_2$)(CH$_2$—C[=W]—O-aryl);
37) Z is —C(=W)—NH—CH(—[CH$_2$]$_4$—NH—C[=W]-t-BuO)(—C[=W]—NH$_2$);
38) Z is —C(=W)—NH—CH(—CH$_2$—CH$_2$—C[=W]-t-BuO)(C[=W]—NH$_2$);
39) Z is —C(=W)—NH—CH—(R$^3$)(C[=W]—NH$_2$) where R$^3$ is as defined above;
40) Z is —C(=W)—NH—CH(—CH$_2$—R$^3$)(—C[=W]—NH$_2$) where R$^3$ is as defined above;
41) Z is —C(=W)—NH—CH(—CH$_2$OH)(—C[=W]—NH$_2$);
42) Z is —C(=W)—NH—CH—(C[=W]—NH$_2$)(C[=W]—NH$_2$);
43) Z is —C(=W)—NHR$^2$—C[=W]—NH$_2$ where R$^2$ is as defined above;
44) Z is —C(=W)—NH—CH(—[CH$_2$]$_4$—NH—C[=W]—O—CH$_2$—R$^3$)(—C[=W]—NH$_2$) where R$^3$ is as defined above;
45) Z is —C(=W)—NH—CH(—CH$_2$—C[=W]—NH$_2$)(—C[=W]—NH$_2$);
46) Z is —C(=W)—NH—CH(—CH$_2$—R$^3$)(—C[=W]—NH$_2$) where R$^3$ is as defined above;
47) Z is —C(=W)—NH—CH(—[CH$_2$]$_4$—NH$_2$)(—C[=W]—NH$_2$);
48) Z is —C(=W)—NH—CH(—CH[R$^2$][OH])(—C[=W]—NH$_2$) where R$^2$ is as defined above;
49) Z is —C(=W)—NH—CH(—R$^2$)(—C[=W]—NH$_2$) where R$^2$ is as defined above;
50) Z is —C(=W)—NH—CH(—R$^2$—C[=W]—NH$_2$)(—C[=W]—NH$_2$) where R$^2$ is as defined above;
51) Z is —C(=W)—NH—CH(—R$^2$—SCH$_3$)(—C[=W]—NH$_2$) where R$^2$ is as defined above;
52) Z is —C(=W)—NH—CH(—C[=N]—NH$_2$)(—C[=W]NH$_2$);
53) Z is —C(=W)—NH—CH(—R$_3$)(—C[=W]—NH$_2$) where R$^3$ is as defined above;
54) Z is —C(=W)—NH—CH(—CH$_2$—R$^3$)(—C[=W]—NH$_2$) where R$^3$ is as defined above;
55) Z is —C(=W)—NH—CH(—R$^2$)(—C[=W]—NH$_2$) where R$^2$ is as defined above;
56) Z is —C(=W)—NH—R$^2$—C(=W)R$^3$ where R$^2$ is alkylene and R$^3$ is aryl or heteroaryl;
57) Z is —C(=W)—NH—R$^2$—R$^3$—C(=W)NH$_2$ where R$^2$ is alkylene and R$^3$ is aryl or heteroaryl; and
58) Z is —C(=W)—NH—NH—R$^2$—R$^3$—C(=W)NH$_2$, where R$^2$ is alkylene and R$^3$ is aryl or heteroaryl;
59) Z is —C(=W)—NH—NH—CH(R$^3$)—C(=W)R$^2$, where R$^3$ is optionally substituted aryl or heteroaryl and R$^2$ is —NH$_2$;
60) Z is —C(=W)NHR$^2$(—R$^3$)—C(=W)NH$_2$, where R$^2$ is alkylene, and R$^3$ is optionally substituted alkyl, aryl, or heteroaryl;
61) Z is —C(=W)NHR$^2$(—R$^3$)—C(=W)NH—R$^2$—C(=W)OH, where R$^2$ is alkylene, and R$^3$ is optionally substituted alkyl, aryl or heteroaryl;
62) Z is —C(=W)NHR$^2$(—R$^3$)—C(=W)NH—R$^2$NH$_2$, where R$^2$ is alkylene and R$^3$ is optionally substituted alkyl, aryl or heteroaryl;
63) Z is —C(=W)NHR$^2$(—R$^3$)—C(=W)NH—R$^3$ where R$^2$ is alkylene and R$^3$ is optionally substituted alkyl, aryl or heteroaryl;
64) Z is —C(=W)—R$^2$—(CH$_2$)$_p$-A-C(=W)—NH$_2$, where R$^2$ is —NH, p is 0-10, A is a divalent, optionally substituted aryl or heteroaryl, and W is O or S; and
65) Z is —C(=W)NH—R$^3$, where R$^3$ is an optionally substituted heterocycle;
66) Z is —C(=W)—NH—R$^2$—R$^8$—R$^3$ where W is O or S, R$^2$ is alkylene, alkenylene or alkynylene, R$^8$ is —SO$_2$, and R$^3$ is —NH$_2$;
67) Z is —C(=W)—NH—NH—R$^2$(R$^3$)—R$^8$—NH$_2$ where W is O or S, R$^2$ is alkylene, alkenylene or alkynylene, R$^3$ is aryl, arylene, or heteroaryl, and R$^8$ is —SO$_2$;
68) Z is —C(=W)—NH—R$^3$(R$^8$—NH$_2$) where W is O or S, R$^3$ is aryl, arylene or heteroaryl, and R$^8$ is —SO$_2$;
69) Z is —C(=W)—NH—R$^2$R$^3$(R$^8$—NH$_2$) where W is O or S, R$^2$ is alkylene, alkenylene or alkynylene, R$^3$ is aryl, arylene or heteroaryl, and R$^8$ is —SO$_2$;
70) Z is —C(=W)—NH—R$^3$(R$^2$R$^8$—NH$_2$) where W is O or S, R$^3$ is aryl, arylene, or heteroaryl, R$^2$ is alkylene, alkenylene or alkynylene, and R$^8$ is —SO$_2$;
71) Z is —C(=W)NHR$^2$(—R$^3$)—C(=W)NH—R$^2$—C(=W)OH, where R$^2$ is an optionally substituted alkylene, alkenylene or alkynylene, and R$^3$ is any of the definitions provided above;
72) Z is —C(=W)NHR$^2$(—R$^3$)—C(=W)NH—R$^2$—C(=W)NH$_2$, where R$^2$ is an optionally substituted alkylene, alkenylene or alkynylene, and R$^3$ is any of the definitions provided above;
73) Z is —C(=W)NHR$^2$—C(=W)NH—R$^2$—C(=W)OH, where R$^2$ is an optionally substituted alkylene, alkenylene or alkynylene; or
74) Z is —C(=W)NHR$^2$—C(=W)NH—R$^2$—C(=W)NH$_2$, where R$^2$ is an optionally substituted alkylene, alkenylene or alkynylene, and when not otherwise specified, each W is independently O or S.

A second series of preferred subembodiments of the first embodiment is defined when R$^{4'}$, R$^{5'}$, R$^{6'}$, and R$^{7'}$ are defined as follows:

1) R$^{6'}$ and R$^{7'}$ are hydrogen, and R$^{4'}$ and R$^{5'}$ independently are (i), halo, (ii) —NO$_2$, (iii) —CN, (iv) —OR$^2$, (v) —NR$^2$R$^2$, (vi) —NH—R$^8$—C$_{1-3}$alkyl, (vii) —NHCO—C$_{1-3}$alkyl, (viii) oxime, (ix) hydrazine, (x) —NH(SO$_2$)C$_{1-3}$ alkyl; (xi) C$_{1-3}$ alkyl or alkenyl optionally substituted with one or more of —OH, —SR, C(=W)H, C(=W)OH, halogen, NR$^2$R$^2$, C$_{1-3}$ alkoxy, or C$_{1-3}$ thioether; (xii) —NH—O—C$_{1-3}$ alkyl; or (xiii) —NHOH;

2) R$^{4'}$ and R$^{7'}$ are hydrogen, and R$^{5'}$ and R$^{6'}$ independently are (i), halo, (ii) —NO$_2$, (iii) —CN, (iv) —OR$^2$, (v) —NR$^2$R$^2$, (vi) —NHSO$_2$—C$_{1-3}$alkyl, (vii) —NHCO—C$_{1-3}$alkyl, (viii) oxime, (ix) hydrazine, (x) —NH—O—C$_{1-3}$ alkyl; (xi) —NH—OH; or (xii) C$_{1-3}$ alkyl or alkenyl optionally substituted with one or more of —OH, —SR, C(=W)H, C(=W)OH, halogen, NR$^2$R$^2$, C$_{1-3}$ alkoxy, or C$_{1-3}$ thioether;

3) R$^{4'}$ and R$^{6'}$ are hydrogen, and R$^{5'}$ and R$^{7'}$ independently are (i), halo, (ii) —NO$_2$, (iii) —CN, (iv) —OR$^2$, (v) —NR$^2$R$^2$, (vi) —NHSO$_2$—C$_{1-3}$alkyl, (vii) —NHCO—C$_{1-3}$alkyl, (viii) oxime, (ix) hydrazine, (x) —NH—O—C$_{1-3}$ alkyl; (xi) —NHOH; or (xii) C$_{1-3}$ alkyl or alkenyl optionally substituted with one or more of —OH, —SR, C(=W)H, C(=W)OH, halogen, NR$^2$R$^2$, C$_{1-3}$ alkoxy, or C$_{1-3}$ thioether;

4) R$^{4'}$ and R$^{7'}$ are hydrogen, and R$^{5'}$ and R$^{6'}$ independently are (i), halo, (ii) —NO$_2$, (iii) —CN, (iv) —OR$^2$, (v) —NR$^2$R$^2$, (vi) —NH—O—C$_{1-3}$ alkyl, (vii) —NH—OH, or (viii) C$_{1-3}$ alkyl or alkenyl optionally substituted with one or more of —OH, —SR, C(=W)H, C(=W)OH, halogen, or NH$_2$;

5) R$^{4'}$ and R$^{6'}$ are hydrogen, and R$^{5'}$ and R$^{7'}$ independently are (i), halo, (ii) —NO$_2$, (iii) —CN, (iv) —OR$^2$, (v) —NR$^2$R$^2$, (vi) —NH—O—C$_{1-3}$ alkyl, (vii) —NHOH, or (viii) C$_{1-3}$ alkyl or alkenyl optionally substituted with one or more of —OH, —SR, C(=W)H, C(=W)OH, halogen, or NH$_2$;

6) R$^{6'}$ and R$^{7'}$ are hydrogen, and R$^{4'}$ and R$^{5'}$ independently are halo or C$_{1-3}$ alkyl or alkenyl substituted with one or more halo;

7) R$^{4'}$ and R$^{7'}$ are hydrogen, and R$^{5'}$ and R$^{6'}$ independently are halo or C$_{1-3}$ alkyl or alkenyl substituted with one or more halo;

8) R$^{4'}$ and R$^{6'}$ are hydrogen, and R$^{5'}$ and R$^{7'}$ independently are halo or C$_{1-3}$ alkyl or alkenyl substituted with one or more halo;

9) R$^{6'}$ and R$^{7'}$ are hydrogen, and R$^{4'}$ and R$^{5'}$ independently are Cl, F, or CF$_3$;

10) R$^{4'}$ and R$^{7'}$ are hydrogen, and R$^{5'}$ and R$^{6'}$ independently are Cl, F, or CF$_3$; or 11) R$^{4'}$ and R$^{6'}$ are hydrogen, and R$^{5'}$ and R$^{7'}$ independently are Cl, F, or CF$_3$;

wherein A, R, R$^2$ and W are all as defined above.

A third series of preferred subembodiments of the first embodiment is defined when R$^{2'''}$, R$^{3'''}$, R$^{4'''}$, R$^{5'''}$, and R$^{6'''}$ are defined as follows:

1) R$^{2'''}$, R$^{4'''}$, and R$^{6'''}$ are hydrogen, and R$^{3'''}$ and R$^{5'''}$ are independently (i) halogen, (ii) NO$_2$, (iii) —CN, (iv) —OR$^2$, (v) —NH—R$^8$—C$_{1-3}$alkyl, (vi) —NHCO—C$_{1-3}$alkyl, (vii) oxime, (vii) hydrazine, (viii) —N(OH)C$_{1-3}$ alkyl, or (ix) —C$_{1-5}$ alkyl or alkenyl optionally substituted with one or more of —OH, —SR, C(=W)H, C(=W)OH, halogen, NR$^2$R$^2$, C$_{1-5}$ thioether, or C$_{1-5}$ alkoxy, (x) —C$_{1-5}$ alkoxy, (xi) —OH, or (xii) —NR$^2$R$^2$;

2) R$^{2'''}$, R$^{4'''}$, and R$^{6'''}$ are hydrogen, and R$^{3'''}$ and R$^{5'''}$ are independently (i) halogen, or (ii) —C$_{1-3}$ alkyl or alkenyl optionally substituted with one or more halogen;

3) R$^{2'''}$, R$^{3'''}$, R$^{4'''}$, R$^{5'''}$, and R$^{6'''}$ are H;

4) R$^{2'''}$, R$^{4'''}$, and R$^{6'''}$ are H, and R$^{3'''}$ and R$^{5'''}$ are methyl;

5) R$^{2'''}$, R$^{4'''}$, and R$^{6'''}$ are H, and R$^{3'''}$ and R$^{5'''}$ are Cl;

6) R$^{2'''}$, R$^{4'''}$, and R$^{6'''}$ are H, and R$^{3'''}$ and R$^{5'''}$ are F; or 7) R$^{2'''}$, R$^{4'''}$, and R$^{6'''}$ are H, and R$^{3'''}$ and R$^{5'''}$ are CF$_3$, wherein R, R$^2$, R$^8$ and W are all as defined above.

A fourth series of preferred subembodiments are defined when Z is as defined in any one of the first series of preferred subembodiments of the first embodiment, R$^{4'}$, R$^{5'}$, R$^{6'}$, and R$^{7'}$ are as defined in any one of the second series of preferred subembodiments of the first embodiment, and R$^{2'''}$, R$^{3'''}$, R$^{4'''}$, R$^{5'''}$, and R$^{6'''}$, are as defined in the first embodiment.

A fifth series of preferred subembodiments are defined when Z is as defined in any one of the first series of preferred subembodiments of the first embodiment, R$^{4'}$, R$^{5'}$, R$^{6'}$, and R$^{7'}$ are as defined in the first embodiment, and R$^{2'''}$, R$^{3'''}$, R$^{4'''}$, R$^{5'''}$, and R$^{6'''}$, are as defined in any one of the third series of preferred subembodiment of the first embodiment.

A sixth series of preferred subembodiments are defined when Z is as defined in the first embodiment, R$^{4'}$, R$^{5'}$, R$^6$, and R$^{7'}$ are as defined in any one of the second series of preferred subembodiments of the first embodiment, and R$^{2'''}$, R$^{3'''}$, R$^{4'''}$, R$^{5'''}$, and R$^{6'''}$, are as defined in any one of the third series of preferred subembodiments of the first embodiment.

A seventh series of preferred subembodiments are defined when Z is as defined in any one of the first series of preferred subembodiments of the first embodiment, R$^{4'}$, R$^{5'}$, R$^{6'}$, and R$^{7'}$ are as defined in any one of the second series of preferred subembodiments of the first embodiment, and R$^{2'''}$, R$^{3'''}$, R$^{4'''}$, R$^{5'''}$, and R$^{6'''}$, are as defined in any one of the third series of preferred subembodiments of the first embodiment.

In each of the subembodiments within the first, second, third, fourth, fifth, sixth, and seventh preferred series of subembodiments of the first embodiment, Y is preferably SO$_2$.

Preferred species of the first embodiment are defined when:

1) Z is —C(=W)NHNHC$_2$H$_5$OH, R$^{6'}$ and R$^{7'}$ are hydrogen, R$^4$ is F or Cl, R$^{5'}$ is F or Cl, R$^{2'''}$, R$^{4'''}$, and R$^{6'''}$, are H, R$^{3'''}$ and R$^{5'''}$ are methyl;

2) Z is —C(=W)NHCH$_2$C(=W)NH$_2$, R$^{4'}$ is F or Cl, R$^{6'}$ and R$^{7'}$ are hydrogen, R$^{5'}$ is F or Cl, R$^{2'''}$, R$^{4'''}$, and R$^{6'''}$, are H, R$^{3'''}$ and R$^{5'''}$ are methyl;

3) Z is —C(=W)NHCH$_2$CONHNH$_2$, R$^{4'}$ is F or Cl, R$^{6'}$, and R$^{7'}$ are hydrogen, R$^{5'}$ is F or Cl, R$^{2'''}$, R$^{4'''}$, and R$^{6'''}$, are H, R$^{3'''}$ and R$^{5'''}$ are methyl;

4) Z is —C(=W)NHCH$_2$CH$_2$-(2NO$_2$, 5Me imidazole), R$^{4'}$ is F or Cl, R$^{6'}$ and R$^{7'}$ are hydrogen, R$^{5'}$ is F or Cl, R$^{2'''}$, R$^{4'''}$, and R$^{6'''}$, are H, R$^{3'''}$ and R$^{5'''}$ are methyl;

5) Z is —C(=W)NHCH$_2$NHCH(CH$_3$)C(=W)OH, R$^{4'}$ is F or Cl, R$^{6'}$ and R$^{7'}$ are hydrogen, R$^{5'}$ is F or Cl, R$^{2'''}$, R$^{4'''}$, and R$^{6'''}$, are H, R$^{3'''}$ and R$^{5'''}$ are methyl;

6) Z is —C(=W)CH=CHC(=W)NH$_2$, R$^{4'}$ is F or Cl, R$^{6'}$ and R$^{7'}$ are hydrogen, R$^{5'}$ is F or Cl, R$^{2'''}$, R$^{4'''}$, and R$^{6'''}$, are H, R$^{3'''}$ and R$^{5'''}$ are methyl;

7) Z is —C(=W)NHNHCH$_2$C(=W)NH$_2$, R$^{4'}$ is F or Cl, R$^{5'}$ is Cl or F, R$^{6'}$ and R$^{7'}$ are both H, R$^{3'''}$ and R$^{5'''}$ are both methyl, R$^{2'''}$, R$^{4'''}$ and R$^{6'''}$ are all hydrogen;

8) Z is —C(=W)NH—CH$_2$—C(=W)R$^2$ where W is O or S, R$_2$ is NH$_2$; R$^{4'}$ is Cl or F; R$^{5'}$ is Cl or F; R$^{6'}$, R$^{7'}$, R$^{2'''}$, R$^{4'''}$, and R$^{6'''}$ are hydrogen; R$^{3'''}$ and R$^{5'''}$ are methyl;

9) Z is —C(=W)—NH—CH$_2$-A-C(=W)NH$_2$ where W is O or S; R$^{4'}$ is Cl or F; R$^{5'}$ is Cl or F; R$^{6'}$, R$^{7'}$, R$^{2'''}$, R$^{4'''}$, and R$^{6'''}$ are hydrogen; R$^{3'''}$ and R$^{5'''}$ are methyl;

10) Z is —C(=W)R$^2$CH-A-C(=W)H where W is O or S, and R$^2$ is NH; R$^{4'}$ is Cl or F; R$^{5'}$ is Cl or F; R$^{6'}$, R$^7$, R$^{2'''}$, R$^{4'''}$, and R$^{6'''}$ are hydrogen; R$^{3'''}$ and R$^{5'''}$ are methyl;

11) Z is —C(=W)R$^2$CH-A-C(=W)OH where W is O or S, and R$^2$ is NH; R is Cl or F; R$^5$ is Cl or F; R$^6$, R$^7$, R$^2$, R$^{4'}$, and R$^{6'''}$ are hydrogen; R$^{3'''}$ and R$^5$ are methyl;

12) Z is —C(=W)R$^2$CH-A-R$^3$ where W is O or S. A is an optionally substituted alkenylene, R$^2$ is NH, and R$^3$ is CH$_3$; R$^{4'}$ is Cl or F; R$^{5'}$ is Cl or F; R$^{6'}$, R$^7$ ', R$^{2'''}$, R$^{4'''}$, and R$^{6'''}$ are hydrogen; R$^{3'''}$ and R$^{5'''}$ are methyl;

13) Z is C(=W)NHR$^2$C(=W)R$^2$ where W is O or S, and R$^2$ is an optionally substituted, branched chain alkylene or NH; R$^{4'}$ is F or Cl, R$^{5'}$ is Cl or F, R$^{6'}$ and R$^{7'}$ are both H, R$^{3'''}$ and R$^{5'''}$ are both methyl, R$^{2'''}$, R$^{4'''}$ and R$^{6'''}$ are all H;

14) Z is —C(=W)R$^2$ where W is O or S; R$^2$ is NH; R$^{4'}$ and R$^{5'}$ independently are Cl or F, R$^{6'}$ and R$^{7'}$ are both H, R$^{3'''}$ and R$^{5'''}$ are both methyl, R$^{2'''}$, R$^{4'''}$ and R$^{6'''}$ are all H;

15) Z is —C(=W)R$^2$R$^3$-heterocycle, where W is O or S; R$^2$ is NH; R$^3$ is CH$_2$; heterocycle is an optionally substituted morpholine, imidazole, or pyrrole; R$^{4'}$ and R$^{5'}$ independently are Cl or F; R$^{6'}$ and R$^{7'}$ are both H; R$^{3'''}$ and R$^{5'''}$ are both methyl, R$^{2'''}$, R$^{4'''}$ and R$^{6'''}$ are all H;

16) Z is —C(=W)R$^2$—C(=W)—OR$^3$, where W is 0; R$^2$ is optionally substituted alkyl; R$^3$ is benzyloxy; R$^{4'}$ and R$^{5'}$ 17) Z is —C(=W)R²—NH—C(=W)—C$_{1-4}$ alkoxy, where W is O or S; R² is optionally substituted alkyl; R⁴' and R⁵' independently are Cl or F; R⁶' and R⁷' are both H; R³'' and R⁵'' are both methyl, R²'', R⁴'' and R⁶'' are all H;
18) Z is —C(=W)R²—C(=W)A, where W is O or S; R² is optionally substituted alkyl; A is C$_{1-4}$ alkoxy; R⁴' and R⁵' independently are Cl or F; R⁶' and R⁷' are both H; R³'' and R⁵'' are both methyl, R²'', R⁴'' and R⁶'' are all H;
19) Z is —C(=W)R²R³ where W is O or S; R² is optionally substituted alkyl; R³ is optionally substituted phenyl; R⁴' and R⁵' independently are Cl or F; R⁶' and R⁷' are both H; R³'' and R⁵'' are both methyl, R², R⁴ and R⁶'' are all hydrogen;
20) Z is —C(=W)R²—NH—C(=W)OR³ where W is O or S; R² is optionally substituted alkyl; R³ is benzyl; R⁴' and R⁵' independently are Cl or F; R⁶' and R⁷' are both H; R³'' and R⁵'' are both methyl, R²'', R⁴'' and R⁶'' are all H;
21) Z is —C(=W)R²—C(=W)NH₂, where W is O or S; R² is optionally substituted alkyl; R⁴' and R⁵' independently are Cl or F; R⁶' and R⁷' are both H; R³'' and R⁵'' are both methyl, R²'', R⁴'' and R⁶'' are all H;
22) Z is —C(=O)R²—W—R³ where R² and R³ independently are optionally substituted alkyl; W is S; R⁴' and R⁵' independently are Cl or F; R⁶' and R⁷' are both H; R³'' and R⁵'' are both methyl, R²'', R⁴'' and R⁶'' are all H;
23) Z is —C(=W)—CR²—C(=NH)R² where W is O or S; R² is NH₂; R⁴' and R⁵' independently are Cl or F; R⁶' and R⁷' are both H; R³'' and R⁵'' are both methyl, R²'', R⁴'' and R⁶'' are all H;
24) Z is —C(=W)—NH—CH(R²)—C(=W)—NH₂ where W is O or S; R² is NH₂; R⁴' and R⁵' independently are Cl or F; R⁶' and R⁷' are both H; R³'' and R⁵'' are both methyl, R²'', R⁴'' and R⁶'' are all H;
25) Z is —C(=W)—NH—CH(R²)—C(=W)—NH₂ where W is O or S; R² is NH₂; R⁴ and R⁵ independently are Cl or F; R⁶' and R⁷' are both H; R³'' and R⁵'' are both methyl, R², R⁴ and R⁶'' are all H;
26) Z is —C(=W)—NH—NH₂ where W is O or S; R⁴' and R⁵' independently are Cl or F; R⁶' and R⁷' are both H; R³'' and R⁵'' are both methyl, R²'', R⁴'' and R⁶'' are all H;
27) Z is —C(=W)—NH—NH(R²) where W is O or S; R² is NH₂; R⁴' and R⁵' independently are Cl or F; R⁶' and R⁷' are both H; R³'' and R⁵'' are both methyl, R²'', R⁴'' and R⁶'' are all H;
28) Z is —C(=W)—NH—CH(C[=W]NH₂)(CH₂—C[=W]—O—CH₂-aryl) where W is O or S; R⁴' and R⁵' independently are Cl or F; R⁶' and R⁷' are both H; R³'' and R⁵'' are both methyl, R²'', R⁴'' and R⁶'' are all H;
29) Z is —C(=W)—NH—CH(—[CH₂]₄—NH—C[=W]-t-BuO)(—C[=W]—NH₂) where W is O or S; R⁴' and R⁵' independently are Cl or F; R⁶' and R⁷' are both H; R³'' and R⁵'' are both methyl, R²'', R⁴'' and R⁶'' are all H;
30) Z is —C(=W)—NH—CH(—CH₂—CH₂—C[=W]-t-BuO)(—C[=W]—NH₂) where W is O or S; R⁴' and R⁵' independently are Cl or F; R⁶' and R⁷' are both H; R³'' and R⁵'' are both methyl, R²'', R⁴'' and R⁶'' are all H;
31) Z is —C(=W)—NH—CH(—CH₂—R³)(—C[=W]—NH₂) where W is O or S; R⁴' and R⁵' independently are Cl or F; R⁶' and R⁷' are both H; R³'' and R⁵'' are both methyl, R²'', R⁴'' and R⁶'' are all H;
32) Z is —C(=W)—NH—CH(—CH₂—R³)(—C[=W]—NH₂) where W is O or S; R³ is as defined in the first general embodiment; R⁴' and R⁵' independently are Cl or F; R⁶ and R⁷ are both H; R⁵'' and R⁵'' are both methyl, R²'', R⁴'' and R⁶'' are all H;
33) Z is —C(=W)—NH—CH(—CH₂OH)(—C[=W]—NH₂) where W is O or S; R⁴' and R⁵' independently are Cl or F; R⁶' and R⁷' are both H; R³'' and R⁵'' are both methyl, R²'', R⁴'' and R⁶'' are all H;
34) Z is —C(=W)—NH—CH(—C[=W]—NH₂)(—C[=W]—NH₂) where W is O or S; R⁴' and R⁵' independently are Cl or F; R⁶' and R⁷' are both H; R³'' and R⁵'' are both methyl, R², R⁴ and R⁶'' are all H;
35) Z is —C(=W)—NH—CH(—R³)(—C[=W]—NH₂) where W is O or S; R³ is as defined in the first general embodiment; R⁴' and R⁵' independently are Cl or F; R⁶' and R⁷' are both H; R³'' and R⁵'' are both methyl, R²'', R⁴'' and R⁶'' are all H;
36) Z is —C(=W)—NH—CH(—[CH₂]₄—NH—C[=W]—O—CH₂—R³)(—C[=W]—NH₂) where W is O or S; R³ is as defined in the first general embodiment; R⁴' and R⁵' independently are Cl or F; R⁶' and R⁷' are both H; R³'' and R⁵'' are both methyl, R²'', R⁴'' and R⁶'' are all H;
37) Z is —C(=W)—NH—CH(—CH₂—C[=W]—NH₂)(—C[=W]—NH₂) where W is O or S; R⁴' and R⁵' independently are Cl or F; R⁶' and R⁷' are both H; R³'' and R⁵'' are both methyl, R², R⁴ and R⁶'' are all H;
38) Z is —C(=W)—NH—CH(—CH₂—R³)(—C[=W]—NH₂) where W is O or S; R³ is as defined in the first general embodiment; R⁴' and R⁵' independently are Cl or F; R⁶' and R⁷' are both H; R³'' and R⁵'' are both methyl, R²'', R⁴'' and R⁶'' are all H;
39) Z is —C(=W)—NH—CH(—[CH₂]₄—NH₂)(—C[=W]—NH₂) where W is O or S; R⁴' and R⁵' independently are Cl or F; R⁶' and R⁷' are both H; R³'' and R⁵'' are both methyl, R²'', R⁴'' and R⁶'' are all H;
40) Z is —C(=W)—NH—CH(—CH[R²][OH])(—C[=W]—NH₂) where W is O or S; R² is NH₂; R⁴' and R⁵' independently are Cl or F; R⁶' and R⁷' are both H; R³'' and R⁵'' are both methyl, R²'', R⁴'' and R⁶'' are all H;
41) Z is —C(=W)—NH—CH(—R²)(—C[=W]—NH₂) where W is O or S; R² is NH₂; R⁴' and R⁵' independently are Cl or F; R⁶' and R⁷' are both H; R³'' and R⁵'' are both methyl, R²'', R⁴'' and R⁶'' are all H;
42) Z is —C(=W)—NH—CH(—R²—C[=W]—NH₂)(—C[=W]—NH₂) where W is O or S; R² is NH₂; R¹ and R⁵' independently are Cl or F; R and R⁷' are both H; R³'' and R⁵'' are both methyl, R², R¹ and R⁶'' are all H;
43) Z is —C(=W)—NH—CH(—R²—SCH₃)(—C[=W]—NH₂) where W is O or S; R² is NH₂; R⁴' and R⁵' independently are Cl or F; R⁶' and R⁷' are both H; R³'' and R⁵'' are both methyl, R²'', R⁴'' and R⁶'' are all H;
44) Z is —C(=W)—NH—CH(—C[=NH]—NH₂)(—C[=W]NH₂) where W is O or S; R⁴' and R⁵' independently are Cl or F; R⁶' and R⁷' are both H; R³'' and R⁵'' are both methyl, R²'', R⁴'' and R⁶ are all H;
45) Z is —C(=W)—NH—CH(—R³)(—C[=W]—NH₂) where W is O or S; R³ is as defined in the first general embodiment; R⁴' and R⁵' independently are Cl or F; R⁶' and R⁷' are both H; R³'' and R⁵'' are both methyl, R²'', R⁴'' and R⁶'' are all H;
46) Z is —C(=W)—NH—CH(—CH₂—R³)(—C[=W]—NH₂) where W is O or S; R³ is as defined in the first general embodiment; R⁴' and R⁵' independently are Cl or F; R⁶' and R⁷' are both H; R³'' and R⁵'' are both methyl, R²'', R⁴'' and R⁶'' are all H; or
47) Z is —C(=W)—NH—CH(—R²)(—C[=W]—NH₂) where W is O or S; R² is NH₂; R⁴' and R⁵' independently are Cl or F; R⁶' and R⁷' are both H; R³'' and R⁵'' are both methyl, R²'', R⁴'' and R⁶'' are all H;
48) Z is —C(=W)—NH—NH—CH(R³)—C(=W)R² where W is O or S; R³ is optionally substituted aryl or heteroaryl; $R^2$ is —$NH_2$; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

49) Z is —C(=W)NHR$^2$(—R$^3$)—C(=W)NH$_2$ where W is O or S; $R^2$ is alkylene; $R^3$ is optionally substituted alkyl, aryl or heteroaryl; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

50) Z is —C(=W)NHR$^2$(—R$^3$)—C(=W)NH—R$^2$—C(=W)OH; where W is O or S; $R^2$ is alkylene; and $R^3$ is optionally substituted alkyl, aryl or heteroaryl; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

51) Z is —C(=W)NHR$^2$(—R$^3$)—C(=W)NH—R$^2$NH$_2$, where $R^2$ is alkylene and $R^3$ is optionally substituted alkyl, aryl or heteroaryl; where W is O or S; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

52) Z is —C(=W)NHR$^2$(—R$^3$)—C(=W)NH—R$^3$, where $R^2$ is alkylene and $R^3$ is optionally substituted alkyl, aryl or heteroaryl; where W is O or S; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

53) Z is —C(=W)—R$^2$—(CH$_2$)$_p$-A-C(=W)—NH$_2$, where $R^2$ is —NH, p is 0-10, A is a divalent, optionally substituted aryl or heteroaryl, and W is O or S; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H; and 54) Z is —C(=W)NH—R$^3$, where $R^3$ is an optionally substituted heterocycle, W is O or S, $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

55) Z is —C(=W)—NH—R$^2$—R$^8$—R$^3$ where W is O or S, $R^2$ is alkylene, alkenylene or alkynylene, $R^8$ is —SO$_2$, and $R^3$ is —NH$_2$; $R^{4'}$ and $R^{5'}$ independently are Cl or F; $R^{6'}$ and $R^7$ are both H; $R^{3''}$ and $R^{5''}$ are both methyl, $R^{2'}$, $R^{4''}$ and $R^{6''}$ are all H;

56) Z is —C(=W)—NH—NH—R$^2$(R$^3$)—R$^8$—NH$_2$ where W is O or S, $R^2$ is alkylene, alkenylene or alkynylene, $R^3$ is aryl, arylene, or heteroaryl, and $R^8$ is —SO$_2$; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

57) Z is —C(=W)—NH—R$^3$(R$^8$—NH$_2$) where W is O or S, $R^3$ is aryl, arylene or heteroaryl, and $R^8$ is —SO$_2$; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

58) Z is —C(=W)—NH—R$^2$R$^3$(R$^8$—NH$_2$) where W is O or S, $R^2$ is alkylene, alkenylene or alkynylene, $R^3$ is aryl, arylene or heteroaryl, and $R^8$ is —SO$_2$; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

59) Z is —C(=W)—NH—R$^3$(R$^2$R$^8$—NH$_2$) where W is O or S, $R^3$ is aryl, arylene, or heteroaryl, $R^2$ is alkylene, alkenylene or alkynylene, and $R^8$ is —SO$_2$; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

60) Z is —C(=W)NHR$^2$(—R$^3$)—C(=W)NH—R$^2$—C(=W)OH, where $R^2$ is an optionally substituted alkylene, alkenylene or alkynylene, and $R^3$ is any of the definitions provided in the general embodiment; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

61) Z is —C(=W)NHR$^2$(—R$^3$)—C(=W)NH—R$^2$—C(=W)NH$_2$, where $R^2$ is an optionally substituted alkylene, alkenylene or alkynylene, and $R^3$ is any of the definitions provided above; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

62) Z is —C(=W)NHR$^2$—C(=W)NH—R$^2$—C(=W)OH, where $R^2$ is an optionally substituted alkylene, alkenylene or alkynylene; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H;

63) Z is —C(=W)NHR$^2$—C(=W)NH—R$^2$—C(=W)NH$_2$, where $R^2$ is an optionally substituted alkylene, alkenylene or alkynylene; $R^{4'}$ and $R^{5'}$ independently are Cl or F; $R^{6'}$ and $R^{7'}$ are both H; $R^{3''}$ and $R^{5''}$ are both methyl, $R^{2''}$, $R^{4''}$ and $R^{6''}$ are all H; and when not otherwise specified, A is a divalent linker as defined as above; each W is O, S or NH; and Y is SO$_2$.

Second Embodiment

In the second embodiment of the invention, the compounds are represented generally by the Formula I defined above wherein a first series of preferred subembodiments is given when Z is defined as follows:

1) Z is —C(=W)N(R$^1$R$^3$)C(=W)NH$_2$; $R^2$ is NH and $R^3$ is alkyl;
2) Z is —C(=W)—NH—CH(—C[=W]NH$_2$)(—CH$_2$—C[=W]—O—CH$_3$-aryl);
3) Z is —C(=W)—NH—CH$_2$(—C[=W]NH$_2$)(—CH$_2$—C[=W]—O—CH$_3$-aralkyl);
4) Z is —C(=W)NHNH$_2$;
5) Z is —C(=W)NH—CH$_2$—C(=W)NHNH$_2$;
6) Z is —C(=W)NH—CH(R$^2$)—C(=W)NH$_2$; $R^2$ is NH$_2$ or alkyl;
7) Z is —C(=W)NR$^2$—C(=W)R$^3$; $R^2$ is optionally substituted alkyl, alkenyl or alkynyl; and $R^3$ is NH$_2$;
8) Z is —C(=W)NH—R$^2$—SR where $R^2$ is optionally substituted alkyl, alkenyl or alkynyl;
9) Z is —C(=W)NH—R$^3$—SR$^2$ where $R^2$ is optionally substituted alkyl, alkenyl or alkynyl and $R^3$ is as defined in the general embodiment;
10) Z is —C(=W)—NH—N(R$^3$)(R$^2$); $R^2$ is hydroxyl or alkoxy; $R^3$ is H or alkyl;
11) Z is —C(=W)NH—CH$_2$NH—CH(CH$_3$)C(=W)OH;
12) Z is —C(=W)—NH—N(R$^2$)—CH(R$^2$)—C(=W)R$^2$; $R^2$ is H or NH$_2$;
13) Z is —C(=W)—N(R$^2$)—C(=W)R$^3$; $R^2$ is NH; $R^3$ is CH$_3$;
14) Z is —C(=W)—NH—CH=CH—C(=W)R$^2$; R is NH$_2$;
15) Z is —C(=W)R$^2$(CH)$_2$—C(=W)R$^2$; $R^2$ is NH or NH$_2$;
16) Z is —C(=W)—R$^2$—CH$_2$-A-C(=W)R$^2$; $R^2$ is alkyl or NH$_2$; A is a divalent linker;
17) Z is —C(=W)R$^2$—C(=W)—OR$^3$; $R^2$ is NH; $R^3$ is H or alkyl;
18) Z is —C(=W)—NH—C(=W)OR$^3$; $R^3$ has any definition provided above;
19) Z is —C(=W)R$^3$—NH—C(=W)—R$^2$; $R^2$ is NH$_2$; $R^3$ is NH;
20) Z is —C(=W)—N(R$^8$)—N(R$^2$)—R$^3$; $R^8$ is —C(=O) or —S(O)$_n$; $R^2$ is H or alkyl; $R^3$ is NH$_2$;
21) Z is —C(=W)—N(R$^2$)—N(R$^2$)—C(=W)R$^3$; $R^2$ is H or alkyl; $R^3$ is NH$_2$;
22) Z is —C(=W)—N(—N[R$^2$][R$^3$])—R$^3$; $R^2$ is H or alkyl; each $R^3$ is NH$_2$;
23) Z is —C(=W)R$^2$—C(=W)NH$_2$; $R^2$ is alkyl;
24) Z is —C(=W)R$^2$—SR$^3$; $R^2$ is NH; $R^3$ is H or alkyl;
25) Z is —C(=W)—CH(R$^2$)—C(=NH)R$^2$; each $R^2$ is H or NH$_2$;

26) Z is —C(=W)—NH—(CH$_2$)$_p$—NH—C(=W)-A-C(=W)—R$^2$; R$^2$ is NH$_2$; A is a divalent linker; p is 0-5;

27) Z is —C(=W)—R$^2$—(CH$_2$)$_p$—C(=W)-A-R$^3$—C(=W)—NH$_2$; R$^2$ is NH or alkyl; R$^3$ is alkylene or alkenylene; A is a divalent linker; p is 0-5;

28) Z is —C(=W)—NH—CH(—[CH$_2$]$_p$—NH—C[=W]—R$^2$)(—C[=W]—NH$_2$); R$^2$ is H, alkyl or NH$_2$; p is 0-5;

29) Z is —C(=W)—NH—CH(—[CH$_2$]$_p$—C[=W]—R$^2$)(—C[=W]—NH$_2$); R$^2$ is H, alkyl or NH$_2$; P is 0-5;

30) Z is —C(=W)—NH—CH(—[CH$_2$]$_p$—R$^3$)(—C[=W]—NH$_2$); R$^3$ is H or alkyl; p is 0-5;

31) Z is —C(=W)—NH—CH(—[CH$_2$]$_p$—OH)(—C[=W]—NH$_2$); p is 0-5;

32) Z is —C(=W)—NH—CH(—C[=W]—NH$_2$)(—C[=W]—NH$_2$);

33) Z is —C(=W)—R$^2$—CH(—R$^2$—C[=W]—NH$_2$)(—C[=W]—NH$_2$); R$^2$ is NH or alkylene;

34) Z is —C(=W)—NH—CH—(—CH—R$^2$—OH)(—C[=W]—NH$_2$); R$^2$ is NH or alkylene;

35) Z is —C(=W)—NH—CH(—R$^2$)(—C[=W]—NH$_2$); R$^2$ is alkylene;

36) Z is —C(=W)—NH—CH(—R$^2$—C[=W]—NH$_2$)(—C[=W]—NH$_2$); R$^2$ is alkylene;

37) Z is —C(=W)—NH—CH(—R$^2$—SCH$_3$)(—C[=W]—NH$_2$); R$^2$ is alkylene;

38) Z is —C(=W)—NH—CH(—C[=NH]—NH$_2$)(—C[=W]—NH$_2$),

39) Z is —C(=W)—NH—NH—CH(R$^3$)—C(=W)R$^2$ where R$^3$ is optionally substituted aryl or heteroaryl; R$^2$ is —NH$_2$;

40) Z is —C(=W)NHR$^2$(—R$^3$)—C(=W)NH$_2$ where R$^2$ is alkylene; R$^3$ is optionally substituted alkyl, aryl or heteroaryl;

41) Z is —C(=W)NHR$^2$(—R$^3$)—C(=W)NH—R$^2$—C(=W)OH; where R$^2$ is alkylene; and R$^3$ is optionally substituted alkyl, aryl or heteroaryl;

42) Z is —C(=W)NHR$^2$(—R$^3$)—C(=W)NH—R$^2$NH$_2$, where R$^2$ is alkylene and R$^3$ is optionally substituted alkyl, aryl or heteroaryl;

43) Z is —C(=W)NHR$^2$(—R$^3$)—C(=W)NH—R$^2$, where R$^2$ is alkylene and R$^3$ is optionally substituted alkyl, aryl or heteroaryl;

44) Z is —C(=W)—R$^2$—(CH$_2$)$_p$-A-C(=W)—NH$_2$, where R$^2$ is —NH, p is 0-5, A is a divalent, optionally substituted aryl or heteroaryl;

45) Z is —C(=W)NH—R$^3$, where R$^3$ is an optionally substituted heterocycle;

46) Z is —C(=W)—NH—R$^2$—R$^8$—R$^3$ where R$^2$ is alkylene, alkenylene or alkynylene, R$^8$ is —SO$_2$, and R$^3$ is —NH$_2$;

47) Z is —C(=W)—NH—NH—R$^2$(R$^3$)—R$^8$—NH$_2$ where R$^2$ is alkylene, alkenylene or alkynylene, R$^3$ is aryl, arylene, or heteroaryl, and R$^8$ is —SO$_2$;

48) Z is —C(=W)—NH—R$^3$(R$^8$—NH$_2$) where R$^3$ is aryl, arylene or heteroaryl, and R$^8$ is —SO$_2$;

49) Z is —C(=W)—NH—R$^2$R$^3$(R$^8$—NH$_2$) where R$^2$ is alkylene, alkenylene or alkynylene, R$^3$ is aryl, arylene or heteroaryl, and R$^8$ is —SO$_2$;

50) Z is —C(=W)—NH—R$^3$(R$^2$R$^8$—NH$_2$) where R$^3$ is aryl, arylene, or heteroaryl, R$^2$ is alkylene, alkenylene or alkynylene, and R$^8$ is —SO$_2$;

51) Z is —C(=W)NHR$^2$(—R$^3$)—C(=W)NH—R$^2$—C(=W)OH, where R$^2$ is an optionally substituted alkylene, alkenylene or alkynylene, and R$^3$ is any of the definitions provided above;

52) Z is —C(=W)NHR$^2$(—R$^3$)—C(=W)NH—R$^2$—C(=W)NH$_2$, where R$^2$ is an optionally substituted alkylene, alkenylene or alkynylene, and R$^3$ is any of the definitions provided above;

53) Z is —C(=W)NHR$^2$—C(=W)NH—R$^2$—C(=W)OH, where R$^2$ is an optionally substituted alkylene, alkenylene or alkynylene; or 54) Z is —C(=W)NHR$^2$—C(=W)NH—R$^2$—C(=W)NH$_2$, where R$^2$ is an optionally substituted alkylene, alkenylene or alkynylene;

wherein W is O or S in all instances.

A second series of preferred subembodiments of the second embodiment are defined when R$^{4'}$, R$^{5'}$, R$^{6'}$, and R$^{7'}$ are defined as follows:

1) R$^{4'}$, R$^{6'}$, and R$^{7'}$ are hydrogen, and R$^{5'}$ is (i), halo, (ii) —NO$_2$, (iii) —CN, (iv) —OR$^2$, (v) —NR$^2$R$^2$, (vi) —NH—R$^8$—C$_{1-3}$alkyl, (vii) —NHCO—C$_{1-3}$alkyl, (viii) oxime, (ix) hydrazine, (x) —NH(SO$_2$)C$_{1-3}$ alkyl, (xi) C$_{1-3}$ alkyl or alkenyl optionally substituted with one or more of —OH, C(=W)H, C(=W)OH, halogen, NR R$^2$, C$_{1-3}$ alkoxy, or C$_{1-3}$ thioether, (xii) H, or (xiii) CF$_3$;

2) R$^{5'}$, R$^{6'}$ and R$^{7'}$ are hydrogen, and R$^{4'}$ is (i), halo, (ii) —NO$_2$, (iii) —CN, (iv) —OR$^2$, (v) —NR$^2$R$^2$, (vi) —NH—R$^8$—C$_{1-3}$alkyl, (vii) —NHCO—C$_{1-3}$alkyl, (viii) oxime, (ix) hydrazine, (x) —NH(SO$_2$)C$_{1-3}$ alkyl; (xi) C$_{1-3}$ alkyl or alkenyl optionally substituted with one or more of —OH, —SR, C(=W)H, C(=W)OH, halogen, NR$^2$R$^2$, C$_{1-3}$ alkoxy, or C$_{1-3}$ thioether; (xii) H, or (xiii) CF$_3$;

3) R$^{4'}$, R$^{5'}$ and R$^{7'}$ are hydrogen, and R$^{6'}$ independently are (i), halo, (ii) —NO$_2$, (iii) —CN, (iv) —OR$^2$, (v) —NR$^2$R$^2$, (vi) —NHSO$_2$—C$_{1-3}$alkyl, (vii) —NHCO—C$_{1-3}$alkyl, (viii) oxime, (ix) hydrazine, (x) —NH(OH)C$_{1-3}$ alkyl; (xi) C$_{1-3}$ alkyl or alkenyl optionally substituted with one or more of —OH, —SR, C(=W)H, C(=W)OH, halogen, NR$^2$R$^2$, C$_{1-3}$ alkoxy, or C$_{1-3}$ thioether, (xii) H or (xiii) CF$_3$; or 4) R$^{4'}$, R$^{5'}$ and R$^{6'}$ are hydrogen, and R$^{7'}$ independently are (i), halo, (ii) —NO$_2$, (iii) —CN, (iv) —OR$^2$, (v) —NR$^2$R$^2$, (vi) —NHSO$_2$—C$_{1-3}$alkyl, (vii) —NHCO—C$_{1-3}$alkyl, (viii) oxime, (ix) hydrazine, (x) —NHOH; (xi) C$_{1-3}$ alkyl or alkenyl optionally substituted with one or more of —OH, —SR, C(=W)H, C(=W)OH, halogen, NR R, C$_{1-3}$ alkoxy, or C$_{1-3}$ thioether; (xii) H, or (xiii) CF$_3$, wherein R, R$^2$, R$^8$ and W are all as defined above.

A third series of preferred subembodiments of the second embodiment is defined when R$^{2''}$, R$^{3''}$, R$^{4''}$, R$^{5''}$, and R$^{6''}$, are defined as follows:

1) R$^{2''}$, R$^{4''}$, and R$^{6''}$, are hydrogen, and R$^{3''}$ and R$^{5''}$ are independently (i) halogen, (ii) NO$_2$, (iii) —CN, (iv) —OR$^2$, (v) —NH—R$^8$—C$_{1-3}$alkyl, (vi) —NHCO—C$_{1-3}$ alkyl, (vii) oxime, (vii) hydrazine, (viii) —NHOH, (ix) —NH—O—C$_{1-3}$ alkyl, (x) —C$_{1-5}$ alkyl or alkenyl optionally substituted with one or more of —OH, —SR, C(=W)H, C(=W)OH, halogen, NR$^2$R$^2$, C$_{1-5}$ thioether, or C$_{1-5}$ alkoxy, (xi) —C$_{1-5}$ alkoxy, (xii) —OH, or (xiii) —NR$^2$R$^2$;

2) R$^{2''}$, R$^{4''}$, and R$^{6''}$, are hydrogen, and R$^{3''}$ and R$^{5''}$ are independently (i) halogen, (ii) NO$_2$, (iii) —CN, (iv) —OR$^2$, (v) —NHOH, or (vi) —C$_{1-3}$ alkyl or alkenyl optionally substituted with one or more of —OH, —SR, —C(=W)OH, halogen, or NH$_2$, (vii) —C$_{1-3}$ alkoxy, (viii) —OH, or (ix) —NR$^2$R$^2$;

3) R$^{2''}$, R$^{4''}$, and R$^{6''}$, are hydrogen, and R$^{3''}$ and R$^{5''}$ are independently (i) halogen, or (ii) —C$_{1-3}$ alkyl or alkenyl optionally substituted with one or more halogen;

4) R$^{2''}$, R$^{3''}$, R$^{4''}$, R$^{5''}$, and R$^{6''}$, are H;

5) $R^{2''}$, $R^{4''}$, and $R^{6''}$, are H, and $R^{3''}$ and $R^{5''}$ are methyl;
6) $R^{2''}$, $R^{4''}$, and $R^{6''}$, are H, and $R^{3''}$ and $R^{5''}$ are Cl;
7) $R^{2''}$, $R^{4''}$, and $R^{6''}$, are H, and $R^{3''}$ and $R^{5''}$ are F; or
8) $R^{2''}$, $R^{4''}$, and $R^{6''}$, are H, and $R^{3''}$ and $R^{5''}$ are $CF_3$;

wherein R, $R^2$, $R^8$ and W are all as defined above.

A fourth series of preferred subembodiments is defined when Z is as defined in any one of the first series of preferred subembodiments of the second embodiment, $R^{4'}$, $R^{5'}$, $R^{6'}$, and $R^{7'}$ are as defined in any one of the second series of preferred subembodiments of the second embodiment, and $R^{2''}$, $R^{3''}$, $R^{4''}$, $R^{5''}$, and $R^{6''}$, are as defined in the second embodiment.

A fifth series of preferred subembodiments is defined when Z is as defined in any one of the first series of preferred subembodiments of the second embodiment, $R^{4'}$, $R^{5'}$, $R^{6'}$, and $R^{7'}$ are as defined in the second embodiment, and $R^{2''}$, $R^{3''}$, $R^{4''}$, $R^{5''}$, and $R^{6''}$, are as defined in any one of the third series of preferred subembodiment of the second embodiment.

A sixth series of preferred subembodiments is defined when Z is as defined in the second embodiment, $R^{4'}$, $R^{5'}$, $R^{6'}$, and $R^{7'}$ are as defined in any one of the second series of preferred subembodiments of the second embodiment, and $R^{2''}$, $R^{3''}$, $R^{4''}$, $R^{5''}$, and $R^{6''}$, are as defined in any one of the third series of preferred subembodiments of the second embodiment.

A seventh series of preferred subembodiments is defined when Z is as defined in any one of the first series of preferred subembodiments of the second embodiment, $R^{4'}$, $R^{5'}$, $R^{6'}$, and $R^{7'}$ are as defined in any one of the second series of preferred subembodiments of the second embodiment, and $R^{2''}$, $R^{3''}$, $R^{4''}$, $R^{5''}$, and $R^{6''}$, are as defined in any one of the third series of preferred subembodiments of the second embodiment.

An eighth series of preferred subembodiments of the second embodiment is defined when:
  1) Z is selected from the group consisting of —C—$R^2R^3$; —$CR^2$—C(=W)$R^3$; —$R^2$—C(=W)$R^3$; —$R^2$—C(=W)$R^2$; —$R^2R^3$; or —$R^3$;
  2) $R^{4'}$, $R^{6'}$ and $R^{7'}$ are H, and $R^{5'}$ is (i) oxime, (ii) hydrazine, (iii) $C_{1-3}$ alkyl or alkenyl optionally substituted with one or more of OH, C(=W)H, C(=W)OH, halogen, $NR^2R^2$, $C_{1-3}$ alkoxy, or $C_{1-3}$ thioether; or
    a) $R^{5'}$, $R^{6'}$ and $R^{7'}$ are hydrogen, and $R^{4'}$ is halogen;
    b) $R^{4'}$, $R^{5'}$ and $R^{7'}$ are hydrogen, and $R^{6'}$ is halogen;
    c) $R^{4'}$, $R^{5'}$ and $R^{6'}$ are hydrogen, and $R^{7'}$ is halogen;
    d) $R^{5'}$, $R^{6'}$ and $R^{7'}$ are hydrogen, and $R^{4'}$ is $CF_3$;
    e) $R^{4'}$, $R^{5'}$ and $R^{7'}$ are hydrogen, and $R^{6'}$ is $CF_3$;
    f) $R^{4'}$, $R^{5'}$ and $R^{6'}$ are hydrogen, and $R^{7'}$ is $CF_3$; and
  3) $R^{2''}$, $R^{3''}$, $R^{4''}$, $R^{5''}$ and $R^{6''}$ are as defined in any one of the third series of preferred subembodiments of the second embodiment;

wherein $R^2$, $R^3$ and W are all as defined above.

In each of the subembodiments within the first, second, third, fourth, fifth, sixth, seventh and eighth preferred series of subembodiments of the second embodiment, Y is preferably $SO_2$.

The phenylindoles of this invention belong to a class of anti-HIV agents that inhibit HIV reverse transcriptase activity. Compounds can be screened for their ability to inhibit HIV reverse transcriptase activity in vitro according to screening methods set forth more particularly herein. One can readily determine the spectrum of activity by evaluating the compound in the assays described herein or with another confirmatory assay.

In one embodiment the efficacy of the anti-HIV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or 10 micromolar.

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"). Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

III. Pharmaceutically Acceptable Salts and Prodrugs

The term "pharmaceutically acceptable salt or prodrug" is used throughout the specification to describe any pharmaceutically acceptable form (such as an ester, amide, salt of an ester, salt of an amide or a related group) of a compound that, upon administration to a patient, provides the active compound. As used herein, the term pharmaceutically acceptable salts refers to salts that retain the desired biological activity of the herein-identified compounds and exhibit minimal undesired toxicological effects. Pharmaceutically acceptable salts include those derived from pharmaceutically acceptable inorganic or organic acids and bases. Non-limiting examples of suitable salts include those derived from inorganic acids such as, hydrochloric acid, hydrobromic acid, sulfuric acid, phosphoric acid, nitric acid, bicarbonic acid, carbonic acid and the like, and salts formed with organic acids such as amino acid residue, acetic acid, oxalic acid, tartaric acid, succinic acid, malic acid, malonic acid, ascorbic acid, citric acid, benzoic acid, tannic acid, palmoic acid, alginic acid, polyglutamic acid, tosic acid, methanesulfonic acid, naphthalenesulfonic acid, naphthalenedisulfonic acid, α-ketoglutaric acid, α-glycerophosphoric acid and polygalacturonic acid. Suitable salts include those derived from alkali metals such as lithium, potassium and sodium, alkaline earth metals such as calcium and magnesium, among numerous other acids well known in the pharmaceutical art. Other suitable salts include those derived from other metal cations such as zinc, bismuth, barium, aluminum, copper, and the like, or with a cation formed from an amine, such as ammonia, N,N-dibenzylethylene-diamine, D-glucosamine, tetraethylammonium, or ethylenediamine. Further, suitable salts include those derived from a combinations of acids and bases, for example, a zinc tannate salt or the like.

Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention either possess antiviral activity against HIV, or are metabolized to a compound that exhibits such activity.

Any of the phenylindoles described herein can be administered as a prodrug to increase the activity, bioavailability, stability or otherwise alter the properties of the phenylindole. A number of prodrug ligands are known. In general, alkylation, acylation or other lipophilic modification of a heteroatom of the phenylindole will increase the stability of the compound. Examples of substituent groups that can replace one or more hydrogens on a heterocycle include, but are not limited to alkyl, aryl, steroids, carbohydrates, including sugars, 1,2-diacylglycerol, phospholipids, phosphotidylcholine, phosphocholine and alcohols. Any of these can be used in combination with the disclosed phenylindoles to achieve a desired effect.

IV. Definitions

The following definitions and term construction are intended, unless otherwise indicated.

Specific and preferred values listed below for radicals, substituents and ranges, are for illustration only; they do not exclude other defined values or other values within defined ranges for the radicals and substituents.

Halo is fluoro, chloro, bromo, or iodo.

Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term alkyl, as used herein, unless otherwise specified, refers to a saturated straight, branched, or cyclic, primary, secondary, or tertiary hydrocarbon of $C_1$ to $C_{12}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. When the context of this document allows alkyl to be substituted, the moieties with which the alkyl group can be substituted are selected from the group consisting of hydroxyl, amino, alkylamino, arylamino, alkoxy, aryloxy, aryl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The terms lower alkyl and alkylene, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms alkenyl and alkynyl refer to alkyl moieties, including both substituted and substituted forms, wherein at least one saturated C—C bond is replaced by a double or triple bond. Thus, $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $(C_2-C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkylene" refers to a saturated, straight chain, divalent alkyl radical of the formula $—(CH_2)_n—$, wherein n can be 1, 2, 3, 4, 5, 6, 7, 8, 9, or 10. The terms "alkenylene" and "alkynylene" refer to unsaturated, straight or branched chain, optionally substituted divalent alkenyl and alkynyl.

As used herein, with exceptions as noted, "aryl" is intended to mean any stable monocyclic, bicyclic or tricyclic carbon ring of up to 8 members in each ring, wherein at least one ring is aromatic as defined by the Huckel 4n+2 rule. The term "arylene" is used to denote the divalent state of an aryl, such as where an aryl group is found within a substituent chain. Examples of aryl ring systems include phenyl, naphthyl, biphenyl, and tetrahydronaphthyl. The aryl group can be substituted with one or more moieties selected from the group consisting of hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

Reagents utilized in synthetic processes include NaHMDS, sodium hexamethyldisilizane; THF, tetrahydrofuran; TFA, tetrafluoroacetic acid; and DABCO, 1,4-diazabicyclo [2.2.2]octane.

The term heterocycle or heterocyclic, as used herein except where noted represents a stable 4- to 8-membered monocyclic or stable 8- to 11-membered bicyclic heterocyclic ring which is either saturated or unsaturated, including heteroaryl, and which consists of carbon atoms and from one to three heteroatoms selected from the group consisting of N, O, S, and P; and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

Nonlimiting examples of heteroaryl and heterocyclic groups include furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2, 4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkyl-pyrimidines, N5-benzylpyrimidines, N5-halopyrimidines, N5-vinyl-pyrimidine, N5-acetylenic pyrimidine, N5-acyl pyrimidine, N5-hydroxyalkyl purine, and N6-thioalkyl purine, and isoxazolyl. The heteroaromatic and heterocyclic moieties can be optionally substituted as described above for aryl, including substituted with one or more substituents selected from hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The heteroaromatic can be partially or totally hydrogenated as desired. As a nonlimiting example, dihydropyridine can be used in place of pyridine. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term acyl refers to a compound of formula RC(O)—, wherein R is substituted or unsubstituted alkyl or aryl, as defined herein. The term carboxyl refers to a compound of the formula —C(=W)OR, wherein R is substituted or unsubstituted alkyl or aryl, as defined herein, and W is as defined herein.

The term aralkyl, as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above. In both instances, aralkylene and alkarylene denote the divalent states of the corresponding structures.

The term alkoxy, as used herein, and unless otherwise specified, refers to a moiety of the structure —O-alkyl, wherein alkyl is as defined above.

The term amino, as used herein, refers to a moiety represented by the structure —NR$_2$, and includes primary amines, and secondary, and tertiary amines substituted by alkyl, aryl, heterocycle, acyl, and sulfinylalkyl. Thus, R$_2$ may represent two hydrogens, two alkyl moieties, or one hydrogen and one alkyl moiety.

The term amido, as used herein, refers to a moiety represented by the structure —C(=W)NR$_2$, wherein R$_2$ is as defined for amino.

As used herein, an "amino acid residue" is that portion of a natural amino acid that includes all but the —OH group of the —COOH moiety, as for example, in Ala, Arg, Asn, Asp, Cys, Glu, Gln, Gly, His, Hyl, Hyp, Ile, Leu Lys, Met, Phe, Pro, Ser, Thr, Trp, Tyr, and Val, in D or L form, or a residue of an unnatural amino acid, as for example, a phosphoserine; phosphothreonine; phosphotyrosine; gamma-carboxyglutamate; hippuric acid; octahydroindole-2-carboxylic acid; statine; 1,2,3,4,-tetrahydroisoquinoline-3-carboxylic acid; penicillamine; omithine; citrulline; α-methyl-alanine; para-benzoylphenylalanine; phenylglycine; propargyl-glycine; sarcosine; or tert-butylglycine residue having one or more open valences.

The term also comprises natural and unnatural amino acid residues bearing amino protecting groups such as acetyl, acyl, trifluoroacetyl, and benzyloxycarbonyl, as well as natural and unnatural amino acid residues protected at the carboxy moiety with protecting groups such as a C$_1$-C$_6$ alkyl, phenyl or benzyl ester and amide. Other suitable amino and carboxy protecting groups are known to those skilled in the art. See for example, T. W. Greene, *Protecting Groups in Organic Synthesis*; Wiley: New York, 1981; D. Voet, Biochemistry, Wiley: New York, 1990; L. Stryer, *Biochemistry*, (3$^{rd}$ Ed), W. H. Freeman and Co.: New York, 1975; J. March, *Advanced Organic Chemistry, Reactions Mechanisms and Structure*, (2$^{nd}$ Ed.), McGraw Hill: New York, 1977; F. Carey and R. Sundberg, *Advanced Organic Chemistry Part B: Reactions and Synthesis*, (2$^{nd}$ Ed.), Plenum: New York, 1977; and references cited therein.

It is intended that in all instances where natural and unnatural amino acids contain one or more chiral centers, all possible stereochemical configurations, including both "L" and "D" forms and mixtures thereof including racemic mixtures, are contained herein.

As used here, a "retrovirus" includes any virus that expresses reverse transcriptase. Examples of a retrovirus include, but are not limited to, HIV-1, HIV-2, HTLV-I, HTLV-II, FeLV, FIV, SIV, AMV, MMTV, and MoMuLV.

As used herein, "reverse transcriptase (RT)" refers to an enzyme having a non-nucleoside inhibitory ("NNI") binding site similar to that of HIV-1 RT and to which ligands bind.

One means by which RT activity can be determined is by measuring viral replication. One measure of HIV-1 viral replication is the p24 core antigen enzyme immunoassay, such as, for example, the assay commercially available from Coulter Corporation/Immunotech, Inc. (Westbrooke, Mich.). Another means by which RT activity is analyzed is by assay of recombinant HIV-1 reverse transcriptase (rRT) activity, for example, using the Quan-T-RT assay system commercially available from Amersham (Arlington Heights, Ill.) and described in Bosworth, et al., Nature 1989, 341: 167-168.

As used herein, a compound that "inhibits replication of human immunodeficiency virus (HIV)" means a compound that, when contacted with HIV-1, for example, via HIV-infected cells, effects a reduction in the amount of HIV-1 as compared with untreated control. Inhibition of replication of HIV-1 can be measured by various means known in the art, for example, the p24 assay disclosed herein.

As used herein, a compound that is useful in "salvage therapy," means a compound that can be taken with any regimen after a patient's initial treatment regimen has failed.

The term host, as used herein, refers to an unicellular or multicellular organism in which the virus can replicate, including cell lines and animals, and preferably a human. Alternatively, the host can be carrying a part of the HIV genome, whose replication or function can be altered by the compounds of the present invention. The term host specifically refers to infected cells, cells transfected with all or part of the HIV genome and animals, in particular, primates (including chimpanzees) and humans. In most animal applications of the present invention, the host is a human patient. Veterinary applications, in certain indications, however, are clearly anticipated by the present invention (such as chimpanzees).

V. Combination or Alternation Therapy

In a preferred but not necessary embodiment, the phenylindole of the present invention is administered in combination or alternation with another anti-HIV agent or an agent that treats opportunistic infections associated with HIV. In one embodiment the effect of administration of the two or more agents in combination or alternation is synergistic.

Drug resistance most typically occurs by mutation of a gene that encodes for an enzyme used in the viral replication cycle, and most typically in the case of HIV, in either the reverse transcriptase or protease genes. It has been demonstrated that the efficacy of a drug against HIV infection can be prolonged, augmented, or restored by administering the compound in combination or alternation with a second, and perhaps third, antiviral compound that induces a different mutation(s) from that selected for by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a protease inhibitor, a reverse transcriptase inhibitor (a "RTI"), which can be either a synthetic nucleoside reverse transcriptase inhibitor (a "NRTI") or a non-nucleoside reverse transcriptase inhibitor (a "NNRTI"), and HIV-integrase inhibitor, or a chemokine inhibitor. In other embodiments, the second (or third) compound can be a pyrophosphate analog, or a fusion binding inhibitor. A list compiling resistance data collected in vitro and in vivo for a number of antiviral compounds is found in Schinazi et al., Mutations in retroviral genes associated with drug resistance, *International Antiviral News*, Volume 5 (8), International Medical Press 1997.

Non-limiting examples of antiviral agents that can be used in combination or alternation with the compounds disclosed herein for HIV therapy include foscarnet; carbovir, acyclovir, interferon, stavudine, and β-D-dioxolane nucleosides such as β-D-dioxolanylguanine (DXG), and β-D-dioxolanyl-6-chloropurine (ACP).

The following drugs have been approved by the FDA or are currently in clinical trials for use in the treatment of HIV infection, and therefore in one embodiment, can be used in combination and/or alternation with the compounds of the present invention.

| Drug Name | Manufacturer |
| --- | --- |
| 3TC, Epivir ® brand lamivudine | GlaxoSmithKline |
| abacavir generic Ziagen ®, ABC, or 1592U89 | GlaxoSmithKline |
| ABC, Ziagen ® brand abacavir, or 1592U89 | GlaxoSmithKline |
| ABT-378/r, or Kaletra ® brand lopinavir/ritonavir | Abbott Laboratories |
| AG-1549, S-1153, or capravirine (CPV) | Pfizer |
| AG1661, Remune ® brand HIV-1 Immunogen, or Salk vaccine | Immune Response Corp. |
| Agenerase ® brand amprenavir (APV), 141W94, or VX-478 | GlaxoSmithKline |
| aldesleukin generic Proleukin ®, or Interleukin-2 (IL-2) | Chiron Corporation |
| amdoxovir, or DAPD | Gilead Sciences |
| amprenavir generic Agenerase ®, APV, 141W94, or VX-478 | GlaxoSmithKline |
| APV, Agenerase ® brand amprenavir, 141W94, or VX-478 | GlaxoSmithKline |
| atazanavir generic Reyataz ™, or BMS-232632 | Bristol-Myers Squibb |
| AZT, Retrovir ® brand zidovudine (ZDV) | GlaxoSmithKline |
| Bis(POC) PMPA, Viread ® brand tenofovir DF | Gilead Sciences |
| BMS-232632, or Reyataz ™ brand atazanavir | Bristol-Myers Squibb |
| BMS-56190, or DPC-083 | Bristol-Myers Squibb |
| calanolide A | Sarawak Medichem |
| capravirine (CPV), AG-1549, or S-1153 | Pfizer |
| Combivir ® brand zidovudine + lamivudine, or AZT + 3TC | GlaxoSmithKline |
| CPV (capravirine), AG-1549, or S-1153 | Pfizer |
| Crixivan ® brand indinavir (IDV), or MK-639 | Merck & Co. |
| d4T, Zerit ® brand stavudine, or BMY-27857 | Bristol-Myers Squibb |
| DAPD, or amdoxovir | Gilead Sciences |
| ddC, or Hivid ® brand zalcitabine | Hoffmann-La Roche |
| ddI, Videx ® brand didanosine, or BMY-40900 | Bristol-Myers Squibb |
| delavirdine generic Rescriptor ®, DLV, or U-90152S/T | Pfizer |
| didanosine generic Videx ®, ddI, or BMY-40900 | Bristol-Myers Squibb |
| DLV, Rescriptor ® brand delavirdine, or U-90152S/T | Pfizer |
| DPC-083, or BMS-56190 | Bristol-Myers Squibb |
| Droxia ® brand hydroxyurea (HU) | Bristol-Myers Squibb |
| efavirenz generic Sustiva ®, or EFV | Bristol-Myers Squibb |
| EFV, Sustiva ® brand efavirenz | Bristol-Myers Squibb |
| emtricitabine generic Emtriva ™, or FTC | Gilead Sciences |
| Emtriva ® brand emtricitabine, or FTC | Gilead Sciences |
| enfuvirtide generic Fuzeon ™, or T-20 | Trimeris and Hoffmann-La Roche |
| Epivir ® brand lamivudine, or 3TC | GlaxoSmithKline |
| epoetin alfa (erythropoietin) generic Procrit ® | Ortho Biotech |
| erythropoietin (epoetin alfa) generic Procrit ® | Ortho Biotech |
| Fortovase ® brand saquinavir (Soft Gel Cap), or SQV (SGC) | Hoffmann-La Roche |
| fosamprenavir, or GW-433908, or VX-175 | GlaxoSmithKline |
| FTC, or Emtriva ® brand emtricitabine | Gilead Sciences |
| Fuzeon ™ brand enfuvirtide, or T-20 | Trimeris and Hoffmann-La Roche |
| GW-433908, or fosamprenavir, or VX-175 | GlaxoSmithKline |
| HE2000, or alpha-epibromide | HollisEden Pharmaceuticals |
| HIV-1 Immunogen generic Remune ®, Salk vaccine, or AG1661 | Immune Response Corp. |
| Hivid ® brand zalcitabine, or ddC | Hoffmann-La Roche |
| HU, or Droxia ® brand hydroxyurea | Bristol-Myers Squibb |
| hydroxyurea generic Droxia ®, or HU | Bristol-Myers Squibb |
| IDV, Crixivan ® brand indinavir, or MK-639 | Merck & Co. |
| IL-2 (Interleukin-2), or Proleukin ® brand aldesleukin | Chiron Corporation |
| indinavir generic Crixivan ®, IDV, or MK-639 | Merck & Co. |
| Interleukin-2 (IL-2), or Proleukin ® brand aldesleukin | Chiron Corporation |
| Invirase ® brand saquinavir (Hard Gel Cap), SQV (HGC), or | Hoffmann-La Roche |

-continued

| Drug Name | Manufacturer |
|---|---|
| Ro-31-8959 | |
| Kaletra ® brand lopinavir/ritonavir, or ABT-378/r | Abbott Laboratories |
| lamivudine generic Epivir ®, or 3TC | GlaxoSmithKline |
| lopinavir/ritonavir generic Kaletra ®, or ABT-378/r | Abbott Laboratories |
| MK-639, Crixivan ® brand indinavir (IDV) | Merck & Co. |
| nelfinavir generic Viracept ®, NFV, or AG-1343 | Pfizer |
| nevirapine generic Viramune ®, NVP, or BI-RG-587 | Boehringer Ingelheim |
| NFV, Viracept ® brand nelfinavir, or AG-1343 | Pfizer |
| Norvir ® brand ritonavir (RTV), or ABT-538 | Abbott Laboratories |
| NVP, Viramune ® brand nevirapine, or BI-RG-587 | Boehringer Ingelheim |
| PNU-140690, or tipranavir | Boehringer Ingelheim |
| PRO-542 | Progenics Pharmaceuticals |
| Procrit ® brand epoetin alfa (erythropoietin) | Ortho Biotech |
| Proleukin ® brand aldesleukin, or Interleukin-2 (IL-2) | Chiron Corporation |
| Remune ® brand HIV-1 Immunogen, or Salk vaccine | Immune Response Corp. |
| Rescriptor ® brand delavirdine (DLV), or U-90152S/T | Pfizer |
| Retrovir ® brand zidovudine (ZDV), or AZT | GlaxoSmithKline |
| Reyataz ™ brand atazanavir, or BMS-232632 | Bristol-Myers Squibb |
| ritonavir generic Norvir ®, RTV, or ABT-538 | Abbott Laboratories |
| RTV, Norvir ® brand ritonavir, or ABT-538 | Abbott Laboratories |
| Salk vaccine, Remune ® brand HIV-1 Immunogen, or AG1661 | Immune Response Corp. |
| saquinavir (Hard Gel Cap) generic Invirase ®, SQV (HGC), or Ro-31-8959 | Hoffmann-La Roche |
| saquinavir (Soft Gel Cap) generic Fortovase ®, or SQV (SGC) | Hoffmann-La Roche |
| SCH-C | Schering-Plough |
| Serostim ® brand somatropin | Serono Laboratories |
| somatropin generic Serostim ® | Serono Laboratories |
| SQV (HGC), Invirase ® brand saquinavir (Hard Gel Cap), or Ro-31-8959 | Hoffmann-La Roche |
| SQV (SGC), or Fortovase ® brand saquinavir (Soft Gel Cap) | Hoffmann-La Roche |
| stavudine generic Zerit ®, d4T, or BMY-27857 | Bristol-Myers Squibb |
| Sustiva ® brand efavirenz (EFV) | Bristol-Myers Squibb |
| T-1249 | Trimeris and Hoffmann-La Roche |
| T-20, or Fuzeon ™ brand enfuvirtide | Trimeris and Hoffmann-La Roche |
| TDF, tenofovir DF generic Viread ™, or Bis(POC) PMPA | Gilead Sciences |
| tenofovir DF (TDF) generic Viread ®, Bis(POC) PMPA | Gilead Sciences |
| tipranavir, or PNU-140690 | Boehringer Ingelheim |
| TMC-114 | Tibotec-Virco Group |
| TMC-125 | Tibotec-Virco Group |
| Trizivir ® brand abacavir + zidovudine + lamivudine (ABC + AZT + 3TC) | GlaxoSmithKline |
| Videx ® brand didanosine, ddI, or BMY-40900 | Bristol-Myers Squibb |
| Videx ® EC brand didanosine (ddI): delayed-release capsules | Bristol-Myers Squibb |
| Viracept ® brand nelfinavir (NFV), or AG-1343 | Pfizer |
| Viramune ® brand nevirapine (NVP), or BI-RG-587 | Boehringer Ingelheim |
| Viread ® brand tenofovir DF, or Bis(POC) PMPA | Gilead Sciences |
| VX-175, or fosamprenavir, or GW-433908 | GlaxoSmithKline |
| zalcitabine generic Hivid ®, or ddC | Hoffmann-La Roche |
| ZDV, Retrovir ® brand zidovudine, or AZT | GlaxoSmithKline |
| Zerit ® brand stavudine, d4T, or BMY-27857 | Bristol-Myers Squibb |
| Ziagen ® brand abacavir (ABC), or 1592U89 | GlaxoSmithKline |
| zidovudine generic Retrovir ®, AZT, or ZDV | GlaxoSmithKline |

The following drugs have been approved by the FDA for use in the treatment of complications of HIV infection and AIDS, which can be used in combination and/or alternation with the compounds of the present invention.

Drugs Used to Treat Complications of HIV/Aids

| Brand Name | Generic Name | Use | Manufacturer Name |
|---|---|---|---|
| Abelcet, Ambisome | Amphotericin B, ABLC | antifungal for aspergillosis | various |
| Bactrim, Septra | sulfamethoxazole and trimethoprim | antiprotozoal antibiotic for Pneumocystis carinii pneumonia treatment and prevention | various |
| Biaxin, Klacid | clarithromycin | antibiotic for Mycobacterium avium prevention and treatment | Abbott Laboratories |
| Cytovene | ganciclovir, DHPG | antiviral for CMV retinitis | Roche |
| DaunoXome | daunorubicin-liposomal | chemotherapy for Kaposi's sarcoma | Gilead |
| Diflucan | fluconazole | antifungal for candidiasis, cryptococcal meningitis | Pfizer |
| Doxil | doxorubicin hydrochloride-liposomal | chemotherapy for Kaposi's sarcoma | Ortho Biotech |
| Famvir | famciclovir | antiviral for herpes | Novartis |
| Foscarnet | foscavir | antiviral for herpes, CMV retinitis | Astra Pharmaceuticals |
| Gamimune N | immune globulin, gamma globulin, IGIV | immune booster to prevent bacterial infections in children | Bayer Biologicals |
| Intron A | interferon alfa-2b | Karposi's sarcoma, hepatitis C | Schering |
| Marinol | dronabinol | treat appetite loss | Roxane Laboratories |
| Megace | megestrol acetate | treat appetite, weight loss | Bristol Myers-Squibb |
| Mepron | atovaquone | antiprotozoal antibiotic for Pneumocystis carinii pneumonia treatment and prevention | GlaxoSmithKline |
| Mycobutin, Ansamycin | rifabutin | antimycobacterial antibiotic for Mycobacterium avium prevention | Adria Pharmaceuticals |
| NebuPent | pentamidine | antiprotozoal antibiotic for Pneumocystis carinii pneumonia prevention | Fujisawa |
| Neutrexin | trimetrexate glucuronate and leucovorin | antiprotozoal antibiotic for Pneumocystis carinii pneumonia treatment | MedImmune |
| Panretin gel | alitretinoin gel 0.1% | AIDS-related Karposi's sarcoma | Ligand Pharmaceuticals |
| Procrit, Epogen | erythropoetin, EPO | treat anemia related to AZT therapy | Amgen |
| Roferon A | interferon alfa-2a | Karposi's sarcoma and hepatitis C | Roche |
| Serostim | somatropin rDNA | treat weight loss | Serono |
| Sporanox | itraconazole | antifungal for blastomycosis, histoplasmosis, aspergillosis, and candidiasis | Janssen Pharmaceuticals |
| Taxol | paclitaxel | Karposi's sarcoma | Bristol Myers-Squibb |
| Valcyte | valganciclovir | antiviral for CMV retinitis | Roche |
| Vistide | cidofovir, HPMPC | antiviral for CMV retinitis | Gilead |
| Vitrasert implant | ganciclovir insert | antiviral for CMV retinitis | Bausch & Lomb |
| Vitravene intravitreal injectable | fomivirsen sodium injection | antiviral for CMV retinitis | Isis Pharmaceuticals |
| Zithromax | azithromycin | antibiotic for Mycobacterium avium | Pfizer |

Several products have been allowed to proceed as Investigational New Drugs (IND) by the FDA for the treatment of complications of HIV infection and AIDS. Therefore, the following drugs can be used in combination and/or alternation with the compounds of the present invention.

Trimetrexate glucuronate for the treatment of *Pneumocystis carinii* pneumonia in AIDS patients who cannot tolerate standard forms of treatment.

Ganciclovir for the treatment of cytomegalovirus retinitis in AIDS patients.

Aerosolized pentamidine for the prevention of *Pneumocystis carinii* pneumonia in AIDS patients.

Erythropoietin for the treatment of zidovudine-related anemia.

Atovaquone for the treatment of AIDS patients with *Pneumocystis carinii* pneumonia who are intolerant or unresponsive to trimethoprim-sulfamethoxazole.

Rifabutin for prophylaxis against *Mycobacterium avium* complex bacteremia in AIDS patients.

Vistide intravenous cidofovir for HIV-infected persons with relapsing cytomegalovirus (CMV) retinitis that has progressed despite treatment (Hoffmann-La Roche).

Serostim, a mammalian derived recombinat human growth hormone, for the treatment of AIDS-related wasting (Serono Laboratories).

In general, during alternation therapy, an effective dosage of each agent is administered serially, whereas in combination therapy, effective dosages of two or more agents are administered together. The dosages will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Examples of suitable dosage ranges for anti-HIV compounds, including nucleoside derivatives (e.g. D4T, DDI, and 3TC) or protease inhibitors, for example, nelfinavir and indinavir, can be found in the scientific literature and in the Physicians Desk Reference. Many examples of suitable dosage ranges for other compounds described herein are also found in public literature or can be identified using known procedures. These dosage ranges can be modified as desired to achieve a desired result.

The disclosed combination and alternation regiments are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

VI. Pharmaceutical Compositions

Humans suffering from effects caused by any of the diseases described herein, and in particular, HIV infection, can be treated by administering to the patient an effective amount of the phenylindole, optionally in combination or alternation with another anti-HIV agent, or with a pharmaceutically acceptable salt or prodrug thereof in the presence of a pharmaceutically acceptable carrier or diluent. In one embodiment, humans infected with HIV can be effectively treated by administering to the patient an effective amount of the phenylindole or a pharmaceutically acceptable salt or prodrug thereof in the presence of a pharmaceutically acceptable carrier or diluent. For multiple drug resistant patients, the phenylindole is either administered alone or in combination. The active materials can be administered by any appropriate route, for example, orally, parenterally, enterally, intravenously, intradermally, subcutaneously, transdermally, intranasally or topically, in liquid or solid form.

The active compound(s) are included in the pharmaceutically acceptable carrier or diluent in an amount sufficient to deliver to a patient a therapeutically effective amount of compound to inhibit viral replication in vivo, especially HIV replication, without causing serious toxic effects in the treated patient. By "inhibitory amount" is meant an amount of active ingredient sufficient to exert an inhibitory effect as measured by, for example, an assay such as the ones described herein.

A preferred dose of the compound for an HIV infection will be in the range from about 1 to 75 mg/kg, preferably about 1 to 50 mg/kg, and even more preferably 1 to 20 mg/kg, of body weight per day, more generally 0.1 to about 100 mg per kilogram body weight of the recipient per day or more, depending upon the compound used, the condition or infection treated and the route of administration. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art. For purposes of the present invention, a prophylactically or preventively effective amount of the compositions, according to the present invention, falls within the same concentration range as set forth above for therapeutically effective amount and is usually the same as a therapeutically effective amount.

The compound is conveniently administered in unit any suitable dosage form, including but not limited to one containing 7 to 3000 mg, preferably 70 to 1400 mg of active ingredient per unit dosage form. An oral dosage of 50 to 1000 mg is usually convenient, including in one or multiple dosage forms of 50, 100, 200, 250, 300, 400, 500, 600, 700, 800, 900 or 1000 mg. Lower doses may be used, for example from 10-100 mg, 1-50 mg, 0.1-50 mg, 0.1-20 mg, or 0.1-10.0 mg.

Ideally the active ingredient should be administered to achieve peak plasma concentrations of the active compound of from about 0.02 to 70 µM, preferably about 1.0 to 10 µM, and even more preferably about 0.5 to 10 µM. This may be achieved, for example, by the intravenous injection of a 0.1 to 25% solution of the active ingredient, preferably 0.1 to 5% solution of the active ingredient, optionally in saline, or administration as a bolus of the active ingredient.

The concentration of active compound in the drug composition will depend on absorption, distribution, metabolism and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors.

The compounds or their pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or non-nucleoside antiviral agents, as discussed in more detail above. Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers. these may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VII. Process of Preparation of the Active Compounds

The phenylindoles can be synthesized using any means known in the art. In particular, the methods disclosed in U.S. Pat. No. 5,527,819, hereby incorporated by reference in its entirety for its disclosure of relevant synthetic methods, can be used to synthesize the compounds of the present invention. In particular, the following species can by synthesized by the following methods.

SCHEME 1-
Preparation of Mono-Substituted Phenylindoles

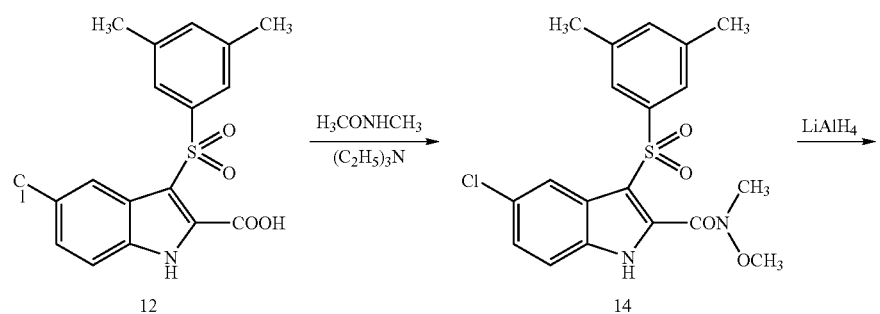

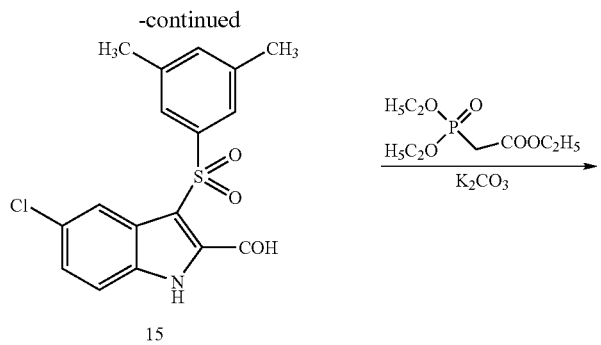
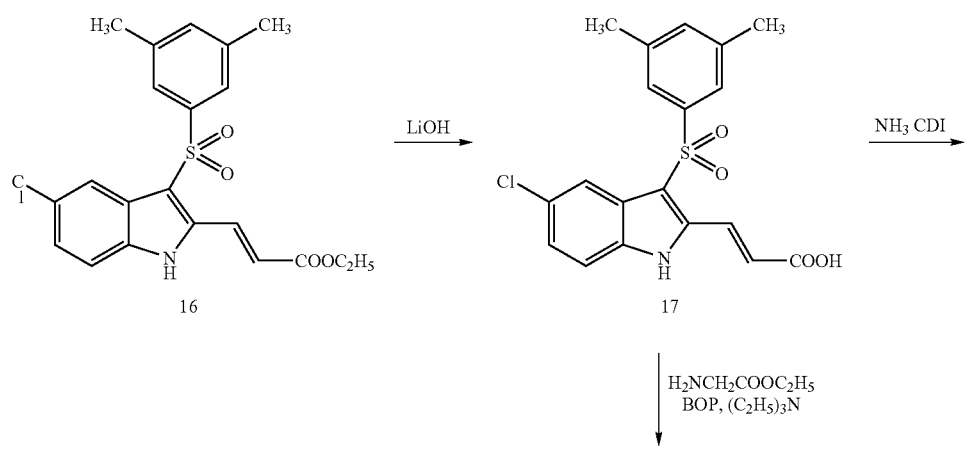
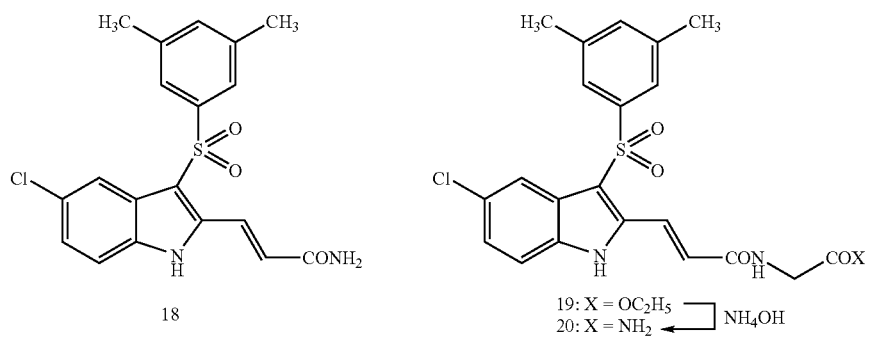

SCHEME 2-
Preparation of Carboxylic and Heterocyclic-Containing Phenylindoles (e.g.Example 1)

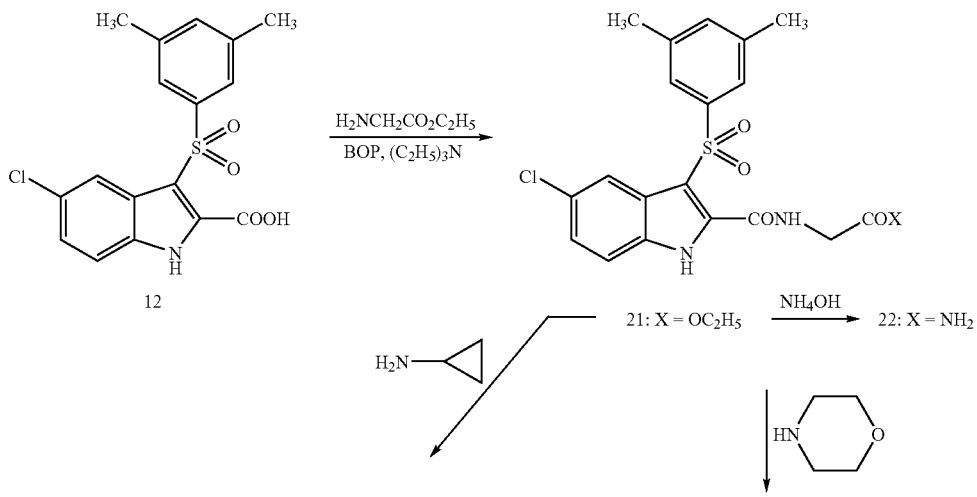

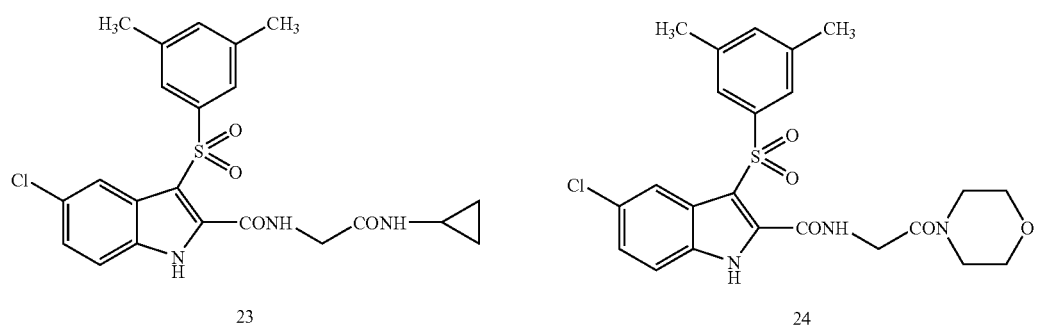

a) 2-[N-[5-Chloro-3-(3,5-dimethylphenylsulfonyl)indol-2-carboxyamido]]-acetamide—21 (Scheme 2)

Reaction of the acid 12 with the glycine ethyl ester hydrochloride in the presence of BOP and triethylamine afforded 2-[N-[5-Chloro-3-(3,5-dimethylphenylsulfonyl)indol-2-carboxy-amido]]-acetic acid ethyl ester (21) which was transformed into amide 22 by heating with ammonium hydroxide. By the same way were prepared amides 23 and 24 by heating with cyclopropylamine or morpholine, respectively.

b) 5-(1H-Pyrrol-1-yl)-3-(3,5-dimethylphenylsulfonyl)indole-2-carboxyamide (e.g. Examples 2 and 3)

5-Nitro-3-(3,5-dimethylphenylsulfonyl)indole-2-carboxyamide was reduced 5-amino-3-(3,5-dimethylphenylsulfonyl)indole-2-carboxyamide with hydrogen in the presence of $PtO_2$ (Adams' catalyst) as a catalyst. Transformation into 5-(1H-pyrrol-1-yl)-3-(3,5-dimethyl-phenylsulfonyl)indole-2-carboxylate was performed by heating with 2,5-dimethoxy-tetrahydrofuran in glacial acetic acid (*Acta Chem. Scand.*, 1952, 6, 667-670; *Acta Chem. Scand.*, 1952, 6, 867-874).

SCHEME 3-
Preparation of Disubstituted-Phenylindoles (e.g. Example 4-7)
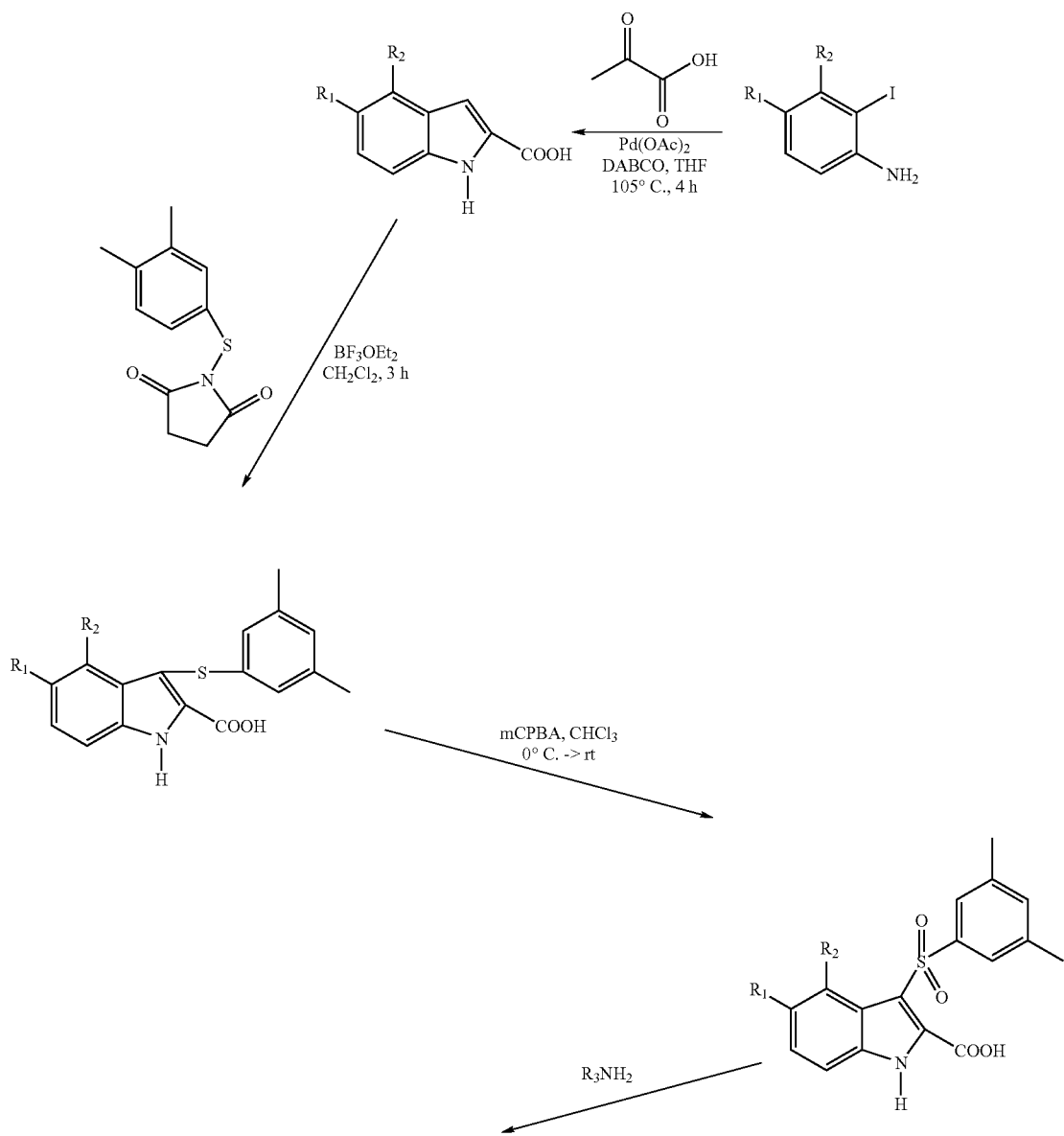

-continued
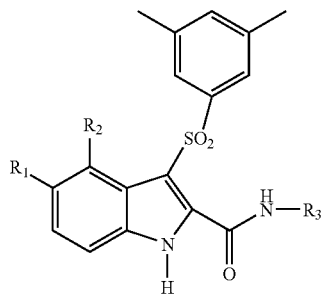
R₃ =
a) 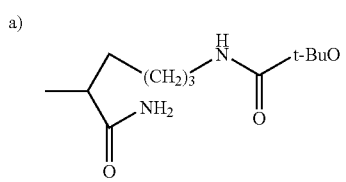  b)
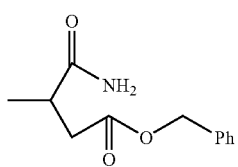
c) 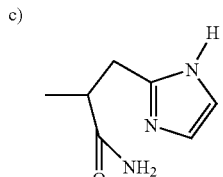  d) 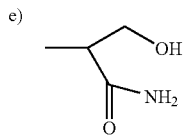
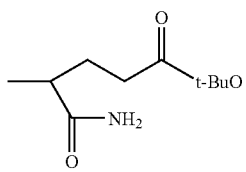
e) 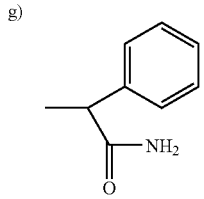  f)
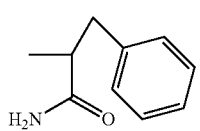
g) 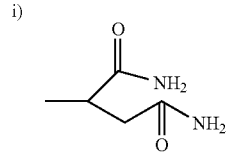  h)
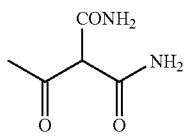
i) 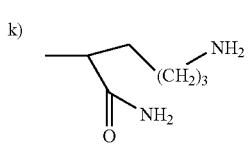  j)
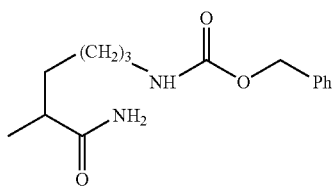
k) 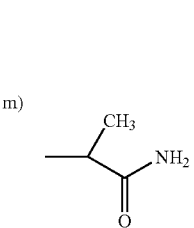  l)
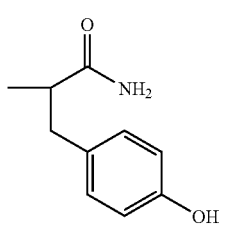
m)  n)
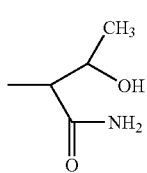

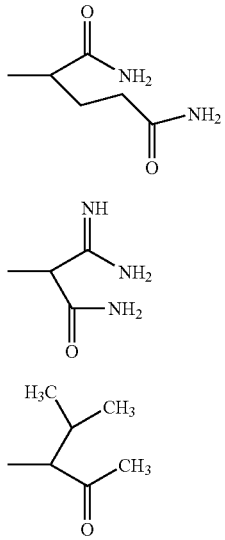

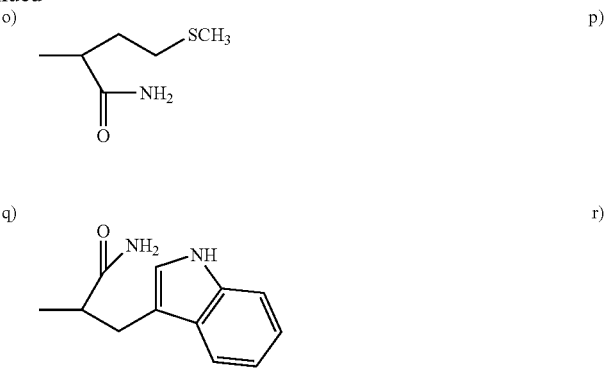

c) 4,5-difluoro- and 5-chloro-4-fluoro-3-(3,5-dimethyl phenyl sulphonyl) indole-2-carboxyhydrazineacetamides (Scheme 3)

5-chloro-4-fluoro-aniline was iodinized by treating 5-chloro-4-fluoroaniline or 4,5-difluoroaniline with ICl—CaCO$_3$ in methanol to form ortho-iodoaniline, which was then coupled with prop-2-yl-acetate in the presence of Pd(OAc)$_2$ catalyst, DMF solvent, and either DABCO or quinuclidine for resistance to amine oxidation, thereby forming a 5-chloro-4-fluoro- or 4,5-difluoro-indole ester. The ester was then condensed with succinimide-phenyl thioether to form a 4,5-difluoro- or 5-chloro-4-fluoro-indole thioether carboxylic acid ester, which was then reduced to form 4,5-difluoro- or 5-chloro-4-fluoro-indole sulfone ester. The latter underwent hydrolysis to form its associated carboxylic acid, which then was coupled with a serine amino acid residue (*J. Org. Chem.*, 1997, 62(9): 2676-2677).

The following working examples provide a further understanding of the method of the present invention. These examples are of illustrative purpose, and are not meant to limit the scope of the invention. Equivalent, similar, or suitable solvents, reagents or reaction conditions may be substituted for those particular solvents, reagents or reaction conditions described herein without departing from the general scope of the method of synthesis.

EXAMPLES

All melting points (mp) were taken on a Büchi 510 apparatus (uncorrected). Infrared spectra (IR): Perkin-Elmer 1310 spectrophotometer. Proton nuclear magnetic resonance ($^1$H NMR) spectra: Bruker AM-200 (200 MHz) FT spectrometer. Column chromatographies: alumina Merck (70-230 mesh) and silica gel Merck (70-230 mesh). TLC: Aluminum oxide TLC cards Fluka (aluminum oxide precoated aluminum cards with fluorescent indicator at 254 nm) and silica gel TLC cards Fluka (silica gel precoated aluminum cards with fluorescent indicator at 254 µm). Developed plates were visualized by spectroline ENF 260C/F UV apparatus. Organic solutions were dried over anhydrous sodium sulfate. Concentration and evaporation of the solvent after reaction or extraction: rotary evaporator Büchi Rotavapor operating at reduced pressure. Elemental analyses (±0.4% of the theoretical values): laboratories of Dr. M. Zancato, Dipartimento di Scienze Farmaceutiche, University of Padova (Italy).

Example 1

Synthesis of N-Cyclopropyl 2-[N-[5-Chloro-3-(3,5-dimethylphenylsulfonyl)-indol-2-carboxyamido]] acetamide (23)

A mixture of 2-[N-[5-chloro-3-(3,5-dimethylphenylsulfonyl)indol-2-carboxyamido]]-acetic acid ethyl ester (21), ethanol (5 mL) and cyclopropylamine (5 mL) was heated at 60° C. for 6 hours. After concentration to a small volume, the residue was extracted with ethyl acetate, washed with brine and dried. Removal of the solvent furnished a crude product which was purified by passing through a silica gel column chromatography (ethyl acetate) to give 0.14 g (69%) of title compound, mp 267-270° C. (ethanol).

N-(1-Morpholin-4-yl)-2-[N-[5-Chloro-3-(3,5-dimethylphenylsulfonyl)indol-2-carboxyamido]]-acetamide (24) was prepared using morpholine—after 48 hours. at 60° C., yield 74%, mp>300° C. (ethanol).

Example 2

Synthesis of 5-(1H-Pyrrol-1-yl)-3-(3,5-dimethylphenylsulfonyl)indole-2-carboxyamide A solution of 5-nitro-3-(3,5-dimethylphenylsulfonyl)indole-2-carboxyamide (0.25 g, 0.0007 mol) in tetrahydrofuran (40 mL) and methanol (16 mL) was reduced under an atmospheric pressure of hydrogen in the presence of PtO$_2$ (50 mg) as a catalyst for 6 hours. Catalyst was separated by filtration and the solvent evaporated to give 0.227 g (100%) of pure 5-amino-3-(3,5-dimethylphenylsulfonyl)indole-2-carboxyamide as a brown oil. A solution of the last compound (0.227 g, 0.0007 mol), 2,5-dimethoxy-tetrahydrofuran (0.09 g, 0.0006 mol) in glacial acetic acid (5 mL) was refluxed for 30 minutes. After evaporation of the solvent the residue was triturated with ice water and extracted with ethyl acetate. Organic layer was washed with brine and dried. Removal of the solvent left the crude product which was purified by passing through a silica gel column chromatography (ethyl acetate as eluent) to give 0.15 g (57%) of title compound, mp 270-272° C. (from ethanol).

5-(1H-Pyrrol-1-yl)-3-(phenylsulfonyl)indole-2-carboxyamide was prepared from 5-nitro-3-(phenylsulfonyl)indole-2-carboxyamide, yield 71%, mp 250° C. (ethanol).

Example 3

Synthesis of 5-(1-Hydroxyethyl)-3-(3,5-dimethylphenylsulfonyl)indole-2-carboxyamide Sodium borohydride (0.03 g, 0.0008 mol) was added to a mixture of 5-acetyl-3-(3,5-dimethylphenylsulfonyl)indole-2-carboxyamide (0.30 g, 0.0008 mol) in tetrahydrofuran (8.5 mL) containing 0.1 mL of water, then reaction was refluxed for 1 hour. After cooling, water was added while stirring for a few minutes, then the mixture was extracted with ethyl acetate, washed with brine and dried. Removal of the solvent furnished 0.25 g (83%) of satisfactory pure title compound, mp 260-260° C. (ethanol).

Example 4

Preparation of 4,5-difluoro-3-(3,5-dimethylphenylsulphonyl)-indole-2-carboxyserinamide 4,5-Difluoro-3-(3,5-dimethylphenylsulphonyl)indole 2-carboxylic acid (3.52 g) and L-serinamide hydrochloride (2.77 g) were dissolved in anhydrous dimethylformamide (90 ml). Triethylamine (2.8 ml) was added and the mixture stirred for 5 minutes. Benzotriazol-1-yloxy-tris(dimethylamino)phosphonium hexafluorophosphate (BOP) (4.69 g) was added and the orange mixture was stirred overnight at room temperature. The reaction mixture was diluted with water (350 ml) and the white solid precipitate collected by filtration, washed with water and dried to afford the title product (3.86 g) as a white powder (97.9% pure by hplc).

In a similar manner 5-chloro-4-fluoro-3-(3,5-dimethylphenylsulphonyl) indole-2-carboxyserinamide was prepared from the 5-chloro-4-fluoro-3-(3,5-dimethylphenylsulphonyl)indole-2-carboxylic acid. The product was obtained as a white solid.

Example 5

Preparation of 4,5-difluoro-3-(3,5-dimethylphenylsulphonyl)-indole-2-(2-(1-pyrrolo)-ethyl)carboxamide 4,5-difluoro-3-(3,5-dimethylphenylsulphonyl)indole 2-carboxylic acid (4.22 g) and 2-(1-pyrrolo)ethylamine (2.63 g) were dissolved in anhydrous dimethylformamide under an atmosphere of nitrogen (100 ml) and triethylamine (3.2 ml) was added. Benzotriazol-1-yloxy-tris(dimethylamino)phosphonium hexafluorophosphate (BOP) (5.63 g) was added and the yellow solution was stirred at room temperature for 18 hours. The reaction mixture was diluted with water (350 ml) and stirred for 30 min. The white precipitate was collected by filtration, washed with water and dried to afford the title product (5.18 g) as a white powder (97.1% pure by hplc).

In a similar manner 5-chloro-4-fluoro-3-(3,5-dimethylphenylsulphonyl) indole-2-(2-(1-pyrrolo)ethyl)carboxamide was prepared from the 5-chloro-4-fluoro-3-(3,5-dimethylphenylsulphonyl) indole-2-carboxylic acid. The product was obtained as a white solid.

Example 6

Preparation of 4,5-Difluoro-3-(3,5-dimethylphenylsulphonyl)-indole-2-(1-morpholinomethyl)carboxamide 4,5-Difluoro-3-(3,5-dimethylphenylsulphonyl)indole 2-carboxamide (670 mg) was mixed with 1,4-dioxan (18 ml) and the resultant white slurry was heated to reflux temperature. Morpholine (0.8 ml) and 37% aqueous formaldehyde (0.7 ml) were added and the mixture rapidly became homogeneous and was refluxed for 24 hours then allowed to cool and poured into water (75 ml). The white slurry was stirred at room temperature for 4 hrs and the white solid was collected by filtration, washed with water and dried to afford the title product (730 mg) as a white powder.

In similar fashion 5-chloro-4-fluoro-3-(3,5-dimethylphenylsulphonyl) indole-2-(1-morpholinomethyl)carboxamide was prepared from 5-chloro-4-fluoro-3-(3,5-dimethylphenylsulphonyl)indole 2-carboxamide. The product was obtained as a white solid.

Example 7

Preparation of 5-Chloro-4-fluoro- and 4,5-Difluoro-3-(3,5-dimethylphenylsulphonyl) indole-2-carboxyhydrazineacetamides 4,5-Difluoro-3-(3,5-dimethylphenylsulphonyl)indole 2-carboxylic acid (4.42 g) and hydrazinoacetate hydrochloride (3.09 g) were dissolved in anhydrous dimethylformamide (100 ml). Triethylamine (3.40 ml) was added and the mixture was stirred for 5 minutes. Benzotriazol-1-yloxy-tris (dimethylamino)phosphonium hexafluorophosphate (BOP) (5.89 g) was added and the orange solution was stirred overnight at room temperature. The mixture was poured into water (275 ml) and the resultant slurry was stirred at room temperature for 30 min. The solid was collected by filtration, washed with water (2×50 ml) and dried at 50° C. under reduced pressure. The product was treated with a mixture of prop-2-yl-acetate (50 ml) and ethanol (5 ml). The resultant slurry was heated under reflux for 30 minutes and allowed to cool to room temperature. The product was collected by filtration, washed with prop-2-yl-acetate (2×10 ml), and dried under reduced pressure at 50° C. to afford the title product (3.34 g) as a white solid.

In similar fashion, 5-chloro-4-fluoro-3-(3,5-dimethylphenylsulphonyl) indole-2-carboxyhydrazine acetamide was prepared from 5-chloro-4-fluoro-3-(3,5-dimethylphenylsulphonyl)indole 2-carboxylic acid. The product was obtained as a white solid.

VIII. Biological Activity Against Drug Resistant Strains of HIV

In one embodiment the phenylindoles of the present invention do not exhibit significant cross resistance with other non-nucleosides reverse transcriptase inhibitors (NNRTI), in that it displays an $EC_{50}$ (in molar concentrations) in a mutant HIV strain of less than approximately 50, 25, 10 or 1 micromolar concentration. In a preferred embodiment, the non-nucleosides reverse transcriptase inhibitors (NNRTI) displays an $EC_{50}$ (in molar concentrations) in a mutant HIV strain of less than approximately 5, 2.5, 1 or 0.1 micromolar concentration. The degree of cross-resistance against a drug resistant strain of HIV can easily be measured by assessing the $EC_{50}$ of the desired indole in the target mutated i.e., drug resistant, virus.

Therefore, in another important embodiment of this invention, a method for treating a patient with a cross-resistant HIV is provided that includes administering an effective HIV-treatment amount of a phenylindole or its prodrug or salt.

This invention has been described with reference to its preferred embodiments. Variations and modifications of the invention, will be obvious to those skilled in the art from the foregoing detailed description of the invention. It is intended that all of these variations and modifications be included within the scope of this invention.

We claim:
1. A compound of Formula I:

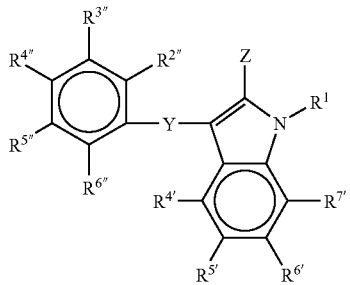

or a pharmaceutically acceptable salt or prodrug thereof, wherein
(a) $R^1$ is hydrogen; acyl; —$C_{1-3}$ alkyl; —C(=W)H; —C(=W)$R^2$; —C(=W)OH; —C(=W)O$R^2$; —C(=W)S$R^2$; —C(=W)NH$_2$; —C(=W)NH$R^2$; —C(=W)N$R^2R^3$; —C(=W)NHN($R^2$)($R^3$); —C(=W)N($R^2$)NH($R^3$); —C(=W)NH—(CH$_2$)$_p$-(amino acid residue) or —(CH$_2$)$_p$-(amino acid residue);
(b) $R^{4'}$, $R^{5'}$, $R^{6'}$, $R^{7'}$, $R^{2''}$, $R^{3''}$, $R^{4''}$, $R^{5''}$ and $R^{6''}$ are each independently H, F, Cl, Br, I; —NO$_2$; —CN; —OH; —O$R^2$; —S$R^2$; —NH$_2$; —NH$R^2$; —N$R^2R^3$; —NH—SO$_2$—$C_{1-3}$alkyl; —N($R^2$)—SO$_2$—$C_{1-3}$alkyl; —NH—CO—$C_{1-3}$alkyl; —N($R^2$)—CO—$C_{1-3}$alkyl; optionally substituted or unsubstituted, branched or unbranched alkyl, alkenyl or alkynyl, CF$_3$, —C$R^2R^2$—S(O)$_n$—$R^3$, —C$R^2R^2$NH$_2$, —C$R^2R^2$NH$R^2$, —C$R^2R^2$N$R^2R^2$ and —C$R^2R^2$—C(=W)$R^2$; optionally substituted or unsubstituted acyl; —C(=W)H; —C(=W)$R^2$; —C(=W)O$R^2$; —C(=W)S$R^2$; —C(=W)NH$_2$; —C(=W)NH$R^2$; —C(=W)—N$R^2R^3$; —C(=W)NH(CH$_2$)$_p$-(amino acid residue), an amino acid residue or —(CH$_2$)$_p$(amino acid residue); wherein if $R^{5'}$ is hydrogen, F, Cl, I, Br, —NO$_2$, —CN, —O$R^2$, —N$R^2R^2$, —NHSO$_2$—$C_{1-3}$alkyl or —NHCO—$C_{1-3}$alkyl, then at least one of $R^{4'}$, $R^{6'}$ and $R^{7'}$ is not hydrogen or alternatively, wherein at least two of $R^{4'}$, $R^{5'}$, $R^{6'}$, $R^{7'}$ are not hydrogen;
(c) Z is optionally substituted or unsubstituted —C(=O) NH$R^2$(—$R^3$)—C(=O)NH—$R^2$—C(=O)OH; —C(=O)NH$R^2$(—$R^3$)—C(=O)NH—$R^2$—C(=O) NH$_2$; —C(=O)NH$R^2$—C(=O)NH—$R^2$—C(=O) OH; —C(=O)NH$R^2$—C(=O)NH—$R^2$—C(=O) NH$_2$; —C(=O)NH$R^2$(—$R^3$)—C(=O)NH—$R^3$; —C(=O)N$R^2$(CH$_2$)$_p$-(amino acid residue)-(C[=O]—NH$_2$); —C(=O)N$R^2$(CH$_2$)$_p$-(amino acid residue)-A-(C[=O]—NH$_2$); —C(=O)—N$R^2$—CH—(C[=O] NH$_2$)(CH$_2$—C[=O]—O—CH$_2$-aryl); —C(=O)—NH—CH(C[=O]NH$_2$)(CH$_2$—C[=O]—O—CH$_2$-aralkyl); —C(=O)—NH—N($R^2$)—CH($R^2$)—C(=O) $R^2$; —C(=O)—N($R^2$)—C(=O)$R^3$; —C(=O)—N ($R^2$)—N($R^2$)—C(=O)$R^3$; —C(=O)—NH—NH—$R^2$ ($R^3$)—$R^8$—NH$_2$; or —C(=O)—NH—NH—CH$_2$—C (=O)$R^2$;
(d) Y is S(O) or S(O)$_n$;
(e) each W is independently O, S, NH, or N$R^2$;
(f) each $R_2$ is independently hydrogen or an optionally substituted or unsubstituted, branched or unbranched lower alkyl, alkenyl, alkynyl, alkylene, alkenylene or alkynylene; acyl; hydroxy; alkoxy; substituted or unsubstituted aryl; substituted or unsubstituted arylene; substituted or unsubstituted aralkyl; —CF$_3$; —NH$_2$; —NH—; —CH$_2$—S(O)$_n$$R^3$; —C(alkyl)$_2$-S(O)$_n$$R^3$; —CH(alkyl)-S(O)$_n$$R^3$; —CH(alkyl)NH$_2$; —C(alkyl)$_2$-NH$_2$; —CH$_2$—NH(alkyl); —C(alkyl)$_2$-NH(alkyl); —CH(alkyl)-NH(alkyl); CH$_2$—NH$R^3$; —CH$_2$N(alkyl) $R^3$; —CH$_2$N(alkyl)$R^3$; —CH(alkyl)-NH$R^3$; —CH (alkyl)-N(alkyl)$R^3$; —C(alkyl)$_2$-NH$R^3$; —C(alkyl)$_2$-N (alkyl)$R^3$; —CH$_2$—C(=W)H; —CH$_2$—C(=W)alkyl; —CH(alkyl)-C(=W)H; —CH(alkyl)-C(=W)alkyl; (CH$_2$)$_p$OH; C(alkyl)$_2$C(=W)H; C(alkyl)$_2$-C(=W) alkyl; —CH(alkenyl)-S(O)$_n$$R^3$; —CH$_2$NH$_2$; —CH (alkenyl)NH$_2$; —C(alkenyl)$_2$-NH$_2$; —CH$_2$—NH(alkenyl); —C(alkenyl)$_2$-NH(alkenyl); —CH(alkenyl)-NH (alkenyl); —CH$_2$—NH$R^3$; —CH$_2$—N(alkenyl)$R^3$; —CH(alkenyl)-NH$R^3$; —CH(alkenyl)-N(alkenyl)$R^3$; —C(alkenyl)$_2$-NH$R^3$; —C(alkenyl)$_2$-N(alkenyl)$R^3$; —CH$_2$—C(=W)H; —CH$_2$—C(=W)alkenyl; —CH (alkenyl)-C(=W)H; —CH(alkenyl)-C(=W)alkenyl; —C(alkenyl)$_2$-C(=W)H; —C(alkenyl)$_2$-C(=W)alkenyl; —CH(alkynyl)-S(O)$_n$$R^3$; —CH(alkynyl)-NH$_2$; —C(alkynyl)$_2$-NH$_2$; —CH$_2$—NH(alkynyl); —C(alkynyl)$_2$-NH(alkynyl); —CH(alkynyl)-NH(alkynyl); —CH$_2$—NH$R^3$; —CH$_2$—N(alkynyl)$R^3$; —CH(alkynyl)-NH$R_3$; —CH(alkynyl)-N(alkynyl)$R^3$; —C(alkynyl)$_2$-NH$R^3$; —C(alkynyl)$_2$-N(alkynyl)$R^3$; —CH$_2$—C (=W)H; —CH$_2$—C(=W)alkynyl; —CH(alkynyl)-C (=W)H; —CH(alkynyl)-C(=W)alkynyl; —C(alkynyl)$_2$-C(=W)H; —C(alkynyl)$_2$-C(=W)alkynyl; —CH(alkoxy)-S(O)$_n$$R^3$; —CH(alkoxy)-NH$_2$; —C(alkoxy)$_2$-NH$_2$; —CH$_2$—NH(alkoxy); —C(alkoxy)$_2$-NH(alkoxy); —CH(alkoxy)-NH (alkoxy); —CH$_2$—NH$R^3$; —CH$_2$—N(alkoxy)$R^3$; —CH(alkoxy)-NH$R_3$; —CH(alkoxy)-N(alkoxy)$R^3$; —C(alkoxy)$_2$-NH$R^3$; —C(alkoxy)$_2$-N(alkoxy)$R^3$; —CH$_2$—C(=W)H; —CH$_2$C(=W)alkoxy; —CH (alkoxy)-C(=W)H; —CH(alkoxy)-C(=W)alkoxy; —C(alkoxy)$_2$-C(=W)H; —C(alkoxy)$_2$-C(=W) alkoxy; —CH(CF$_3$)—S(O)$_n$$R^3$; —CH(CF$_3$)—NH$_2$; —C(CF$_3$)$_2$—NH$_2$; —CH$_2$—NH(CF$_3$); —C(CF$_3$)$_2$—NH(CF$_3$); —CH(CF$_3$)—NH(CF$_3$); —CH$_2$—NH$R^3$; —CH$_2$—N(CF$_3$)$R^3$; —CH(CF$_3$)—NH$R^3$; —CH (CF$_3$)—N(CF$_3$)$R^3$; —C(CF$_3$)$_2$—NH$R^3$; —C(CF$_3$)$_2$—N(CF$_3$)$R^3$; —CH$_2$C(=W)H; —CH$_2$—C(=W)CF$_3$; —CH(CF$_3$)—C(=W)H; —CH(CF$_3$)—C(=W)CF$_3$; —C(CF$_3$)$_2$—C(=W)H; —C(CF$_3$)$_2$—C(=W)CF$_3$; —CH(NH)—S(O)$_n$$R^3$; —CH$_2$—NH—NH$_2$; —CH (NH$_2$)—NH(NH$_2$); —CH$_2$—NHR$_3$; —CH$_2$—N(NH) $R^3$; —CH(NH$_2$)—NH$R^3$; —CH(NH$_2$)—N(NH$_2$)$R^3$; —CH$_2$—C(=W)NH$_2$; —CHR$^2$—C(=W)H; —CH$_2$—C(=W)H; —CH(NH$_2$)—C(=W)NH$_2$;

—CH(NH$_2$)—NH$_2$; —CH$_2$—NH(NH$_2$); —CH$_2$—NHR$^3$; —CH$_2$—N(NH$_2$)R$^3$; —CH(NH$_2$)—NHR$^3$; —CH(NH$_2$)—N(NH$_2$)R$^3$; —CH$_2$—C(=W)H; —CH$_2$—C(=W)NH$_2$; —CH(NH$_2$)—C(=W)H; or —CH(NH$_2$)—C(=W)NH$_2$;

(g) each R$_3$ is independently hydrogen; optionally substituted or unsubstituted, branched or unbranched alkyl, alkenyl, alkynyl, alkylene, alkenylene or alkynylene; CF$_3$; CN; amino; —C(R$^{22}$)(R$^{22}$)—S(O)$_n$NH$_2$; —C(R$^{22}$)(R$^{22}$)—S(O)$_n$—CF$_3$; —C(R$^{22}$)(R$^{22}$)—NH$_2$; —C(R$^{22}$)(R$^{22}$)—NHR$^{22}$—C(R$^{22}$)(R$_{22}$)—NR$_{22}$(alkyl); —C(R$^{22}$)(R$^{22}$)—NR$^{22}$ (alkenyl); —C(R$^{22}$)(R$^{22}$)—NR$^{22}$(alkynyl); —C(R$^{22}$)(R$^{22}$)—NR$^{22}$(CF$_3$); and —C(R$^{22}$)(R$^{22}$)—C(=W)R$^{22}$; optionally substituted or unsubstituted aryl and arylene; optionally substituted or unsubstituted cycloalkyl; optionally substituted or unsubstituted alkylaryl, optionally substituted or unsubstituted aralkyl and aralkylene;

(h) each R$^{22}$ is independently hydrogen or an optionally substituted or unsubstituted, branched or unbranched lower alkyl, alkenyl, alkynyl; acyl; hydroxy; alkoxy; substituted or unsubstituted aryl; substituted or unsubstituted arylene; substituted or unsubstituted aralkyl; amine, alkylamine, alkylsulfonyl, —CF$_3$; —NH$_2$; alkylacyl; amide; alkylamide;

(i) each R$^8$ is independently —C(=O) or —S(O)$_n$;

(j) each n is independently 0, 1 or 2;

(k) each p is independently 0, 1, 2, 3, 4, or 5;

(l) A is a disubstituted spacer selected from the group consisting of alkylene which optionally may have one or more heteroatoms, aryl, cycloalkyl functions in the chain; alkenylene which optionally may have one or more heteroatoms, aryl, cycloalkyl functions in the chain; and optionally substituted aryl, cycloalkyl; and (m) R is selected from the group consisting of H, aryl, alkoxy, substituted or unsubstituted, branched or unbranched alkyl, alkenyl, alkynyl, cycloalkyl, and aralkyl.

2. The compound of claim 1, wherein Y is SO$_2$.

3. The compound of claim 1, wherein Y is SO.

4. The compound of claim 1, wherein:

(a) R$^1$ is hydrogen;

(b) R$^{4'}$, R$^{5'}$, R$^{6'}$, R$^{7'}$, are independently selected from the group consisting of hydrogen, halogen, —NO$_2$, —CN, —OR$^2$, —NR$^2$R$^2$, —NHSO$_2$—C$_{1-3}$alkyl, —NHCO—C$_{1-3}$alkyl, oxime (—CH=N—OH), hydrazine (—NH—NH$_2$), C$_{1-3}$ alkyl and alkenyl optionally substituted with one or more of —OH, —SR, C(=W)H, C(=W)OH, halogen, NR$^2$R$^2$, C$_{1-3}$ alkoxy, and C$_{1-3}$ thioether; wherein any three of R$^{4'}$, R$^{5'}$, R$^{6'}$, or R$^{7'}$ simultaneously must be hydrogen;

(c) R$^{2''}$, R$^{3''}$, R$^{4''}$, R$^{5''}$, and R$^{6''}$, are independently selected from the group consisting of hydrogen, halogen, —NO$_2$, —CN, —OR$^2$, —NHSO$_2$—C$_{1-3}$alkyl, —NHCO—C$_{1-3}$alkyl, oxime, hydrazine, —C$_{1-5}$ alkyl and alkenyl optionally substituted with one or more of —OH, C(=W)H, C(=W)OH, halogen, NR R$^2$, C$_{1-5}$ thioether, or C$_{1-5}$ alkoxy, —C$_{1-5}$ alkoxy, —OH, and —NR$^2$R$^2$;

(d) Z is selected from the group consisting of —C(=O) N(R$^3$)C(=O)NH$_2$; —C(=O)—NH—CH(—C[=O] NH$_2$)(—CH$_2$—C[=O]—O—CH$_2$-aryl); —C(=O)—NH—CH(—C[=O]NH$_2$)(—CH$_2$—C[=O]—O—CH$_2$-aralkyl); —C(=O)NHR$^2$(—R$^3$)—C(=O)NH—R$^2$—C(=O)OH; —C(=O)NHR$^2$(—R$^3$)—C(=O)—NH—R$^2$—C(=O)NH$_2$; —C(=O)NHR$^2$(—R$^3$)—C(=O)—NH—R$^2$—C(=O)OH; —C (=O)NHR$^2$—C(=O) NH—R$^2$—C(=O)NH$_2$; —C(=O)NH—CH$_2$—C(=O)NHNH$_2$; —C(=O)NR$^2$—C(=O)R$^3$; —C(=O)—NH—N(R$^2$)(R$^3$); —C(=O)—NH—N (R$^2$)—CH(R$^2$)—C(=O)R$^2$; —C(=O)—N(R$^8$)—N (R$^2$)—N(R$^2$)(R$^3$); —C(=O)—N(R$^2$)—N(R$^2$)—C (=O)R$^3$; —C(=O)—N(N[R$^2$][R$^3$])—N(N[R$^2$][R$^3$]) R$^3$; —C(=O)—NH—CH(—[CH$_2$]$_p$—C[=O]—R$^2$)—(—C[=O]—NH$_2$); —C(=O)—NH—CH(—[CH$_2$]$_p$—R$^3$)(—C[=O]—NH$_2$); —C(=O)—NH—CH(—[CH$_2$]$_p$—OH)(—C[=O]—NH$_2$); —C(=O)—NH—CH(—C[=O]—NH$_2$)(—C[=O]—NH$_2$); —C(=O)—NH—CH(—[CH$_2$]$_p$—NH—C[=O]O—CH$_2$—R$^3$)(—C[=O]—NH$_2$); —C(=O)—NH—CH(—CH—R$^2$—OH)(—C[=O]—NH$_2$); —C(=O)—NH—CH(—R$^2$)(—C[=O]—NH$_2$); —C(=O)—NH—CH(—R$^2$—C[=O]—NH$_2$)(—C[=O]—NH$_2$); —C(=O)—NH—CH(—R$^2$—SCH$_3$)—(—C[=O]—NH$_2$); —C(=O)—NH—NH—CH(R$^3$)—C(=O)R$^2$; —C(=O)NHR$^2$(—R$^3$)—C(=O)NH—R$^2$—C(=O)OH; —C(=O)—NHR$^2$(—R$^3$)—C(=O)NH—R$^2$NH$_2$; —C(=O)—NH—R$^2$—R$^8$—R$^3$; and —C(=O)—NH—CH—(—C[=N]—NH$_2$)(—C[=O]—NH$_2$);

(e) Y is S(O) or S(O)$_2$;

(f) W is O, S, —NH or —NR$^2$;

(g) each R$^2$ is independently hydrogen or an optionally substituted or unsubstituted, branched or unbranched lower alkyl, alkenyl, alkynyl, alkylene, alkenylene or alkynylene; acyl; hydroxy; alkoxy; substituted or unsubstituted aryl; substituted or unsubstituted aralkyl; —CF$_3$; —NH$_2$; —NH—; —CH$_2$—S(O)$_n$R$^3$; —C(alkyl)$_2$-S(O)$_n$R$^3$; —CH(alkyl)-S(O)$_n$R$^3$; —CH(alkyl)NH$_2$; —C(alkyl)$_2$-NH$_2$; —CH$_2$—NH(alkyl); —C(alkyl)$_2$-NH(alkyl); —CH(alkyl)-NH(alkyl); —CH$_2$NHR$^3$; —CH$_2$N(alkyl)R$^3$; —CH$_2$N(alkyl)R$^3$; —CH(alkyl)-NHR$^3$; —CH(alkyl)-N(alkyl)R$^3$; —C(alkyl)$_2$-NHR$^3$; —C(alkyl)$_2$-N(alkyl)R$^3$; —CH$_2$—C(=W)H; —CH$_2$—C(=W)alkyl; —CH(alkyl)-C(=W)H; —CH(alkyl)-C(=W)alkyl; —(CH$_2$)$_p$OH; —C(alkyl)$_2$-C(=W)H; —C(alkyl)$_2$-C(=W)alkyl; —CH(alkenyl)-S(O)$_n$R$^3$; —CH$_2$NH$_2$; —CH(alkenyl)NH$_2$; —C(alkenyl)$_2$-NH$_2$; —CH$_2$—NH(alkenyl); —C(alkenyl)$_2$-NH(alkenyl); —CH(alkenyl)-NH(alkenyl); —CH$_2$—NHR$^3$; —CH$_2$—N(alkenyl)R$^3$; —CH(alkenyl)-NHR$^3$; —CH(alkenyl)-N(alkenyl)R$^3$; —C(alkenyl)$_2$-NHR$^3$; —C(alkenyl)$_2$-N(alkenyl)R$_3$; —CH$_2$—C(=W)H; —CH$_2$—C(=W)alkenyl; —CH(alkenyl)-C(=W)H; —CH(alkenyl)-C(=W)alkenyl; —C(alkenyl)$_2$-C(=W)H; C(alkenyl)$_2$-C(=W)H; —C(alkenyl)$_2$-C(=W)alkenyl; —CH(alkynyl)-S(O)$_n$R$^3$; —CH(alkynyl)-NH$_2$; —C(alkynyl)$_2$-NH$_2$; —CH$_2$—NH(alkynyl); —C(alkynyl)$_2$-NH(alkynyl); —CH(alkynyl)-NH(alkynyl); —CH$_2$—NHR$^3$; —CH$_2$—N(alkynyl)R$^3$; —CH(alkynyl)-NHR$^3$; —CH(alkynyl)-N(alkynyl)R$^3$; —C(alkynyl)$_2$-NHR$^3$; —C(alkynyl)$_2$-N(alkynyl)R$^3$; —CH$_2$—C(=W)H; —CH$_2$—C(=W)alkynyl; —CH(alkynyl)-C(=W)H; —CH(alkynyl)-C(=W)alkynyl; —C(alkynyl)$_2$-C(=W)H; —C(alkynyl)$_2$-C(=W)alkynyl; —CH(alkoxy)-S(O)$_n$R$^3$; —CH(alkoxy)-NH$_2$; —C(alkoxy)$_2$-NH$_2$; —CH$_2$—NH(alkoxy); —C(alkoxy)$_2$-NH(alkoxy); —CH(alkoxy)-NH(alkoxy); —CH$_2$NHR$^3$; —CH$_2$—N(alkoxy)R$^3$; —CH(alkoxy)-NHR$^3$; —CH(alkoxy)-N(alkoxy)R$^3$; —C(alkoxy)$_2$-NHR$^3$; —C(alkoxy)$_2$-N(alkoxy)R$^3$; —CH$_2$—C(=W)H; —CH$_2$C(alkoxy)-alkoxy; —CH(alkoxy)-C(=W)H; —CH(alkoxy)-C(=W)alkoxy; —C(alkoxy)$_2$-C(=W) H; —C(alkoxy)$_2$-C(=W)alkoxy; —CH(CF$_3$)—

S(O)$_n$R$^3$; —CH(CF$_3$)—NH$_2$; —C(CF$_3$)$_2$—NH$_2$; —CH$_2$—NH(CF$_3$); —C(CF$_3$)$_2$—NH(CF$_3$); —CH(CF$_3$)—NH(CF$_3$); —CH$_2$—NHR$^3$; —CH$_2$—N(CF$_3$)R$^3$; —CH(CF$_3$)—NHR$^3$; —CH(CF$_3$)—N(CF$_3$)R$^3$; —C(CF$_3$)$_2$—NHR$^3$; —C(CF$_3$)$_2$—N(CF$_3$)R$_3$; —CH$_2$C(=W)H; —CH$_2$—C(=W)CF$_3$; —CH(CF$_3$)—C(=W)H; —CH(CF$_3$)—C(=W)CF$_3$; —C(CF$_3$)$_2$—C(=W)H; —C(CF$_3$)$_2$—C(=W)CF$_3$; —CH(NH)—S(O)$_n$R$^3$; —CH$_2$—NH—NH$_2$; —CH(NH$_2$)—NH(NH$_2$); —CH$_2$—NHR$^3$; —CH$_2$—N(NH)R$^3$; —CH(NH$_2$)—NHR$^3$; —CH(NH$_2$)—N(NH$_2$)R$^3$; —CH$_2$—C(=W)NH$_2$; —CHR$^2$—C(=W)H; —CH$_2$—C(=W)H; —CH(NH$_2$)—C(=W)NH$_2$; —CH(NH$_2$)—NH$_2$; —CH$_2$—NH(NH$_2$); —CH$_2$—NHR$^3$; —CH$_2$—N(NH$_2$)R$^3$; —CH(NH$_2$)—NHR$^3$; —CH(NH$_2$)—N(NH$_2$)R$^3$; —CH$_2$—C(=W)H; —CH$_2$—C(=W)NH$_2$; —CH(NH$_2$)—C(=W)H; or —CH(NH$_2$)—C(=W)NH$_2$;

(h) each R$^3$ is independently hydrogen; optionally substituted or unsubstituted, branched or unbranched alkyl, alkenyl, alkynyl, alkylene, alkenylene or alkynylene; CF$_3$; CN; amino; —C(R$^{22}$)(R$^{22}$)—S(O)$_n$—NH$_2$; —C(R$^{22}$)(R$^{22}$)S(O)$_n$—CF$_3$; —C(R$^{22}$)(R$^{22}$)—NH$_2$, —C(R$^{22}$)(R$^{22}$)—NHR$^{22}$, —C(R$^{22}$)(R$^{22}$)—NR$^{22}$ (alkyl); —C(R$^{22}$)(R$^{22}$)—NR$^{22}$(alkenyl); —C(R$^{22}$)(R$^{22}$)—NR$^2$(alkynyl); —C(R$^{22}$)(R$^{22}$)—NR$^{22}$(CF$_3$); and —C(R$^{22}$)(R$^{22}$)—C(=W)R$_{22}$; optionally substituted or unsubstituted aryl and arylene; optionally substituted or unsubstituted cycloalkyl; optionally substituted or unsubstituted alkylaryl, optionally substituted or unsubstituted aralkyl and aralkylene;

(i) each R$^{22}$ is independently hydrogen or an optionally substituted or unsubstituted, branched or unbranched lower alkyl, alkenyl, alkynyl; acyl; hydroxy; alkoxy; substituted or unsubstituted aryl; substituted or unsubstituted arylene; substituted or unsubstituted aralkyl; amine, alkylamine, alkylsulfonyl, —CF$_3$; —NH$_2$; alkylacyl; amide; alkylamide;

(j) A is a disubstituted spacer selected from the group consisting of alkylene which optionally may have one or more heteroatoms, aryl, or cycloalkyl functions in the chain; alkenylene which optionally may have one or more heteroatoms, aryl, or cycloalkyl functions in the chain; and optionally substituted aryl, and cycloalkyl;

(k) R is selected from the group consisting of H; aryl; alkoxy; optionally substituted, branched or unbranched alkyl, alkenyl, alkynyl, cycloalkyl, and aralkyl;

(l) each n is independently 0, 1 or 2;

(m) each p is independently 0, 1, 2, 3, 4 or 5.

5. The compound of claim 4, wherein Y is SO$_2$.
6. The compound of claim 4, wherein Y is SO.
7. A compound of the structure:

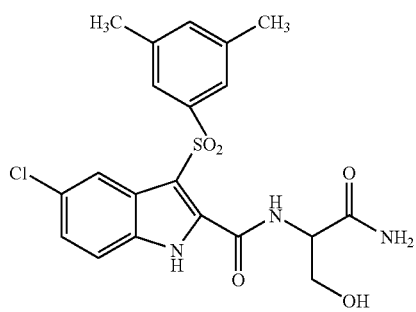

or a pharmaceutically acceptable salt or prodrug thereof.

8. A compound of the structure:

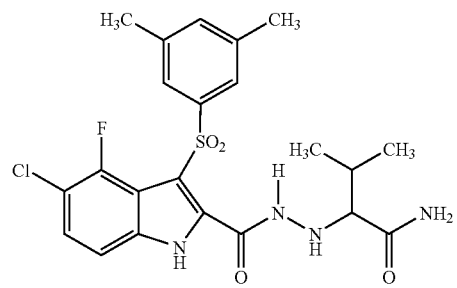

or a pharmaceutically acceptable salt or prodrug thereof.

9. A compound of the structure:

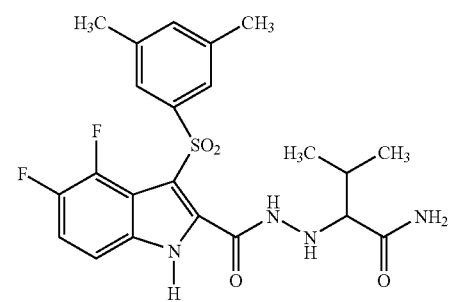

or a pharmaceutically acceptable salt or prodrug thereof.

10. A compound of the structure:

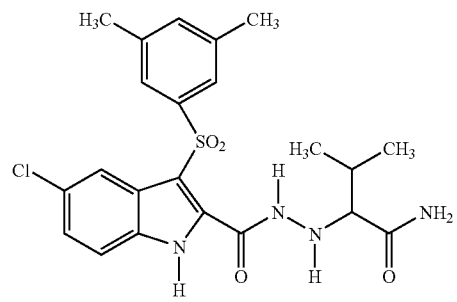

or a pharmaceutically acceptable salt or prodrug thereof.

11. A compound of the structure:

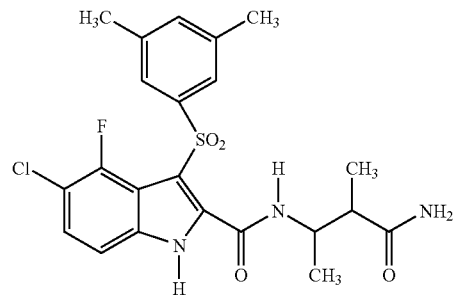

or a pharmaceutically acceptable salt or prodrug thereof.

12. A compound of the structure:

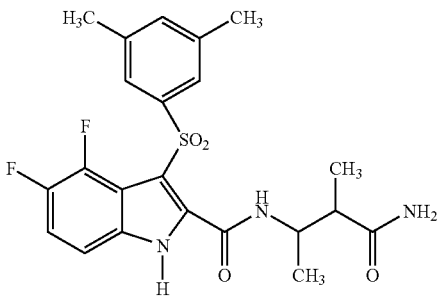

or a pharmaceutically acceptable salt or prodrug thereof.

13. A compound of the structure:

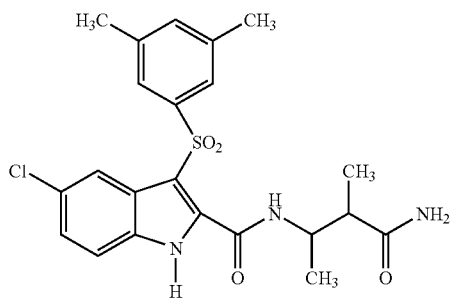

or a pharmaceutically acceptable salt or prodrug thereof.

14. A pharmaceutical composition for the treatment of an HIV infection in a host comprising an effective anti-HIV treatment amount of a compound of Formula I:

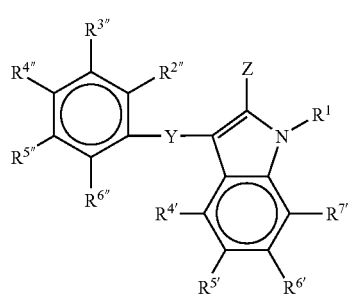

or a pharmaceutically acceptable salt or prodrug thereof, wherein (a) $R^1$ is hydrogen; acyl; —$C_{1-3}$ alkyl; —C(=W)H; —C(=W)$R^2$; —C(=W)OH; —C(=W)O$R^2$; —C(=W)S$R^2$; —C(=W)NH$_2$; —C(=W)NH$R^2$; —C(=W)N$R^2R^3$; —C(=W)NHN($R^2$)($R^3$); —C(=W)N($R^2$)NH($R^3$); —C(=W)NH—(CH$_2$)$_p$-(amino acid residue) or —(CH$_2$)$_p$-(amino acid residue);

(b) $R^{4'}$, $R^{5'}$, $R^{6'}$, $R^{7'}$, $R^{2''}$, $R^{3''}$, $R^{4''}$, $R^{5''}$ and $R^{6'''}$ are each independently H, F, Cl, Br, I; —NO$_2$; —CN; —OH; —O$R^2$; —S$R^2$; —NH$_2$; —NH$R^2$; —N$R^2R^3$; —NH—SO$_2$—C$_{1-3}$alkyl; —N($R^2$)—SO$_2$—C$_{1-3}$alkyl; —NH—CO—C$_{1-3}$alkyl; —N($R^2$)—CO—C$_{1-3}$alkyl; optionally substituted or unsubstituted, branched or unbranched alkyl, alkenyl or alkynyl, CF$_3$, —C$R^2R^2$—S(O)$_n$$R^3$, —C$R^2R^2$NH$_2$, —C$R^2R^2$NH$R^2$, —C$R^2R^2$N$R^2R^3$ and —C$R^2R^2$—C(=W)$R^2$; optionally substituted or unsubstituted acyl; —C(=W)H; —C(=W)$R^2$; —C(=W)O$R^2$; —C(=W)S$R^2$; —C(=W)NH$_2$; —C(=W)NHR ; —C(=W)N$R^2R^3$; —C(W)NH(CH$_2$)$_p$-(amino acid residue), an amino acid residue or —(CH$_2$)$_p$(amino acid residue); wherein if $R^{5'}$ is hydrogen, F, Cl, I, Br, —NO$_2$, —CN, —O$R^2$, —N$R^2R^2$, —NHSO$_2$—C$_{1-3}$alkyl or —NHCO—C$_{1-3}$alkyl, then at least one of $R^{4'}$, $R^{6'}$ and $R^7$ is not hydrogen or alternatively, wherein at least two of $R^{4'}$, $R^{5'}$, $R^{6'}$, $R^{7'}$ are not hydrogen;

(c) Z is optionally substituted or unsubstituted —C(=O)NH$R^2$(—$R^3$)—C(=O)NH—$R^2$—C(=O)OH; —C(=O)NH$R^2$(—$R^3$)—C(=O)NH—$R^2$—C(=O)NH$_2$; —C(=O)NH$R^2$—C(=O)NH—$R^2$—C(=O)OH; —C(=O)NH$R^2$—C(=O)NH—$R^2$—C(=O)NH$_2$; —C(=O)NH$R^2$(—$R^3$)—C(=O)NH—$R^3$; —C(=O)N$R^2$(CH$_2$)$_p$-(amino acid residue)-(C[=O]—NH$_2$); —C(=O)N$R^2$(CH$_2$)$_p$-(amino acid residue)-A-(C[=O]—NH$_2$); —C(=O)—N$R^2$—CH—(C[=O]NH$_2$)(CH$_2$—C[=O]—O—CH$_2$-aryl); —C(=O)—NH—CH(C[=O]NH$_2$)(CH$_2$—C[=O]—O—CH$_2$-aralkyl); —C(=O)—NH—N($R^2$)—CH($R^2$)—C(=O)$R^2$; —C(=O)—N($R^2$)—C(=O)$R^3$; —C(=O)—N($R^2$)—N($R^2$)—C(=O)$R^3$; —C(=O)—NH—NH—$R^2$($R^3$)—$R^8$—NH$_2$; or —C(=O)—NH—NH—CH$_2$—C(=O)$R^2$;

(d) Y is S(O) or S(O)$_n$;

(e) each W is independently O, S, NH, or N$R^2$;

(f) each $R^2$ is independently hydrogen or an optionally substituted or unsubstituted, branched or unbranched lower alkyl, alkenyl, alkynyl, alkylene, alkenylene or alkynylene; acyl; hydroxy; alkoxy; substituted or unsubstituted aryl; substituted or unsubstituted arylene; substituted or unsubstituted aralkyl; —CF$_3$; —NH$_2$; —NH—; —CH$_2$—S(O)$_n$$R^3$; —C(alkyl)$_2$-S(O)$_n$$R^3$; —CH(alkyl)-S(O)$_n$$R^3$; —CH(alkyl)NH$_2$; —C(alkyl)$_2$NH$_2$; —CH$_2$—NH(alkyl); —C(alkyl)$_2$-NH(alkyl); —CH(alkyl)-NH(alkyl); —CH$_2$—NH$R^3$; —CH$_2$N(alkyl)$R^3$; —CH$_2$N(alkyl)$R^3$; CH(alkyl)-NH$R^3$; —CH(alkyl)-N(alkyl)$R^3$; —C(alkyl)$_2$-NH$R^3$; —C(alkyl)$_2$-N(alkyl)$R^3$; —CH$_2$—C(=W)H; —CH$_2$—C(=W)alkyl; —CH(alkyl)-C(=W)H; —CH(alkyl)-C(=W)alkyl; —(CH$_2$)$_p$OH; —C(alkyl)$_2$-C(=W)H; —C(alkyl)$_2$-C(=W)alkyl; —CH(alkenyl)-S(O)$_n$$R^3$; —CH$_2$NH$_2$; —CH(alkenyl)NH$_2$; —C(alkenyl)$_2$-NH$_2$; —CH$_2$—NH(alkenyl); —C(alkenyl)$_2$-NH(alkenyl); —CH(alkenyl)-NH(alkenyl); —CH$_2$—NH$R^3$; —CH$_2$—N(alkenyl)$R^3$; —CH(alkenyl)-NH$R^3$; —CH(alkenyl)-N(alkenyl)$R^3$; —C(alkenyl)$_2$-NH$R^3$; —C(alkenyl)$_2$-N(alkenyl)$R^3$; —CH$_2$—C(=W)H; —CH$_2$—C(=W)alkenyl; —CH(alkenyl)-C(=W)H; —CH(alkenyl)-C(=W)alkenyl; —C(alkenyl)$_2$-C(=W)H; —C(alkenyl)$_2$-C(=W)alkenyl; —CH(alkynyl)-S(O)$_n$$R^3$; —CH(alkynyl)-NH$_2$; —C(alkynyl)$_2$-NH$_2$; —CH$_2$—NH(alkynyl); —C(alkynyl)$_2$-NH(alkynyl); —CH(alkynyl)-NH(alkynyl); —CH$_2$—NH$R^3$; —CH$_2$—N(alkynyl)$R^3$; —CH(alkynyl)-NH$R^3$; —CH(alkynyl)-N(alkynyl)$R^3$; —C(alkynyl)$_2$-NH$R^3$; —C(alkynyl)$_2$-N(alkynyl)$R^3$; —CH$_2$—C(=W)H; —CH$_2$—C(=W)alkynyl; —CH(alkynyl)-C(=W)H; —CH(alkynyl)-C(=W)alkynyl; —C(alkynyl)$_2$-C(=W)H; —C(alkynyl)$_2$-C(=W)alkynyl; —CH(alkoxy)-S(O)$_n$$R^3$; —CH(alkoxy)-NH$_2$; —C(alkoxy)$_2$-NH$_2$; —CH$_2$—NH(alkoxy); —C(alkoxy)$_2$-NH(alkoxy); —CH(alkoxy)-NH(alkoxy); —CH$_2$—NH$R^3$; —CH$_2$—N(alkoxy)$R^3$; —CH(alkoxy)-NH$R^3$; —CH(alkoxy)-N(alkoxy)$R^3$; —C(alkoxy)$_2$-NH$R^3$; —C(alkoxy)$_2$-N(alkoxy)$R^3$;

—CH$_2$—C(=W)H; —CH$_2$C(=W)alkoxy; —CH(alkoxy)-C(=W)H; —CH(alkoxy)-C(=W)alkoxy; —C(alkoxy)$_2$-C(=W)H; —C(alkoxy)$_2$-C(=W)alkoxy; —CH(CF$_3$)—S(O)NR$^3$; —CH(CF$_3$)—NH$_2$; —C(CF$_3$)$_2$—NH$_2$; —CH$_2$—NH(CF$_3$); —C(CF$_3$)$_2$—NH(CF$_3$); —CH(CF$_3$)—NH(CF$_3$); —CH$_2$—NHR$_3$; —CH$_2$—N(CF$_3$)R$^3$; —CH(CF$_3$)—NHR$^3$; —CH(CF$_3$)—N(CF$_3$)R$^3$; —C(CF$_3$)$_2$—NHR$^3$; —C(CF$_3$)$_2$—N(CF$_3$)R$^3$; —CH$_2$C(=W)H; —CH$_2$—C(=W)CF$_3$; —CH(CF$_3$)—C(=W)H; —CH(CF$_3$)—C(=W)CF$_3$; —C(CF$_3$)$_2$—C(=W)H; —C(CF$_3$)$_2$—C(=W)CF$_3$; —CH(NH)—S(O)$_n$R$^3$; —CH$_2$—NH—NH$_2$; —CH(NH$_2$)—NH(NH$_2$); —CH$_2$—NHR$^3$; —CH$_2$—N(NH)R$^3$; —CH(NH$_2$)—NHR$^3$; —CH(NH$_2$)—N(NH$_2$)R$^3$; —CH$_2$—C(=W)NH$_2$; —CHR$^2$—C(=W)H; —CH$_2$—C(=W)H; —CH(NH$_2$)—C(=W)NH$_2$; —CH(NH$_2$)—NH$_2$; —CH$_2$—NH(NH$_2$); —CH$_2$—NHR$^3$; —CH$_2$—N(NH$_2$)R$^3$; —CH(NH$_2$)—NHR$^3$; —CH(NH$_2$)—N(NH$_2$)R$^3$; —CH$_2$—C(=W)H; —CH$_2$—C(=W)NH$_2$; —CH(NH$_2$)—C(=W)H; or —CH(NH$_2$)—C(=W)NH$_2$;

(g) each R$^3$ is independently hydrogen; optionally substituted or unsubstituted, branched or unbranched alkyl, alkenyl, alkynyl, alkylene, alkenylene or alkynylene; CF$_3$; CN; amino; —C(R$^{22}$)(R$^{22}$)—S(O)$_n$—NH$_2$; —C(R$^{22}$)(R$^{22}$)S(O)$_n$—CF$_3$; —C(R$^{22}$)(R$^{22}$)—NH$_2$; —C(R$^{22}$)(R$^{22}$)—NHR$^{22}$, C(R$^{22}$)(R$^{22}$)—NR$^{22}$(alkyl); —C(R$^{22}$)(R$^{22}$)—NR$^{22}$(alkenyl); —C(R$^{22}$)(R$^{22}$)—NR$^{22}$(alkynyl); —C(R$^{22}$)(R$^{22}$)—NR$^{22}$(CF$_3$); and —C(R$^{22}$)(R$^{22}$)—C(=W)R$^{22}$; optionally substituted or unsubstituted aryl and arylene; optionally substituted or unsubstituted cycloalkyl; optionally substituted or unsubstituted alkylaryl, optionally substituted or unsubstituted aralkyl and aralkylene;

(h) each R$^{22}$ is independently hydrogen or an optionally substituted or unsubstituted, branched or unbranched lower alkyl, alkenyl, alkynyl; acyl; hydroxy; alkoxy; substituted or unsubstituted aryl; substituted or unsubstituted arylene; substituted or unsubstituted aralkyl; amine, alkylamine, alkylsulfonyl, —CF$_3$; —NH$_2$; alkylacyl; amide; alkylamide;

(i) each R$^8$ is independently —C(=O) or —S(O)$_n$;

(j) each n is independently 0, 1 or 2;

(k) each p is independently 0, 1, 2, 3, 4, or 5; and (l) A is a disubstituted spacer selected from the group consisting of alkylene which optionally may have one or more heteroatoms, aryl, cycloalkyl functions in the chain; alkenylene which optionally may have one or more heteroatoms, aryl, cycloalkyl functions in the chain; and optionally substituted aryl, cycloalkyl; and (m) R is selected from the group consisting of H, aryl, alkoxy, substituted or unsubstituted, branched or unbranched alkyl, alkenyl, alkynyl, cycloalkyl, and aralkyl optionally in combination with one or more other anti-HIV agent, optionally with a pharmaceutically acceptable carrier or diluent.

15. The pharmaceutical composition of claim 14, wherein Y is SO$_2$.

16. The pharmaceutical composition of claim 14, wherein Y is SO.

17. The pharmaceutical composition of claim 14, wherein:

(a) R$^1$ is hydrogen;

(b) R$^{4'}$, R$^{5'}$, R$^{6'}$, R$^{7'}$, are independently selected from the group consisting of hydrogen, halogen, —NO$_2$, —CN, —OR$^2$, —NR$^2$R$^2$, —NHSO$_2$—C$_{1-3}$alkyl, —NHCO—C$_{1-3}$alkyl, oxime (—CH=N—OH), hydrazine (—NH—NH$_2$), C$_{1-3}$ alkyl and alkenyl optionally substituted with one or more of —OH, —SR, C(=W)H, C(=W)OH, halogen, NR$^2$R$^2$, C$_{1-3}$ alkoxy, and C$_{1-3}$ thioether; wherein any three of R$^{4'}$, R$^{5'}$, R$^{6'}$, or R$^{7'}$ simultaneously must be hydrogen;

(c) R$^{2''}$, R$^{3''}$, R$^{4'''}$, R$^{5'''}$, and R$^{6'}$, are independently selected from the group consisting of hydrogen, halogen, —NO$_2$, —CN, —OR$^2$, —NHSO$_2$—C$_{1-3}$alkyl, —NHCO—C$_{1-3}$alkyl, oxime, hydrazine, —C$_{1-5}$ alkyl and alkenyl optionally substituted with one or more of —OH, C(=W)H, C(=W)OH, halogen, NR$^2$R$^2$, C$_{1-5}$ thioether, or C$_{1-5}$ alkoxy, —C$_{1-5}$ alkoxy, —OH, and —NR$^2$R$^2$;

(d) Z is selected from the group consisting of —C(=O)N(R$^3$)C(=O)NH$_2$; —C(=O)—NH—CH(—C[=O]NH$_2$)(—CH$_2$—C[=O]—O—CH$_2$-aryl); —C(=O)—NH—CH(—C[=O]NH$_2$)(—CH$_2$—C[=O]—O—CH$_2$-aralkyl); —C(=O)NHR$^2$(—R$^3$)—C(=O)NH—R$^2$—C(=O)OH; —C(=O)NHR$^2$(—R$^3$)—C(=O)NH—R$^2$—C(=O)NH$_2$; —C(=O)NHR$^2$—C(=O)NH—R$^2$—C(=O)OH; —C(=O)NHR$^2$—C(=O)NH—R$^2$—C(=O)NH$_2$; —C(=O)NH—CH$_2$—C(=O)NHNH$_2$; —C(=O)NR$^2$—C(=O)R$^3$; —C(O)—NH—N(R$^2$)(R$^3$); —C(=O)—NH—N(R$^2$)—CH(R$^2$)—C(=O)R$^2$; —C(=O)—N(R$^8$)—N(R$^2$)—N(R$^2$)(R$^3$); —C(=O)—N(R$^2$)—N(R$^2$)—C(=O)R$^3$; —C(=O)—N(N[R$^2$][R$^3$])—N(N[R$^2$][R$^3$])R$^3$; —C(=O)—NH—CH(—[CH$_2$]$_p$—C[=O]—R$^2$)—(—C[=O]—NH$_2$); —C(=O)—NH—CH(—[CH$_2$]$_p$—R$^3$)(—C[=O]—NH$_2$); —C(=O)—NH—CH(—[CH$_2$]$_p$—OH)(—C[=O]—NH$_2$); —C(=O)—NH—CH(—C[=O]—NH$_2$)(—C[=O]—NH$_2$);—CH(—[CH$_2$]$_p$—NH—C[=O]O—CH$_2$—R$^3$)(—C[=]—NH$_2$); —C(=O)—NH—CH(—CH—R$^2$—OH)—(—C[=O]—NH$_2$); —C(=O)—NH—CH(—R$^2$)(—C[=O]—NH$_2$); —C(=O)—NH—CH(—R$^2$—C[=O]—NH$_2$)(—C[=O]—NH$_2$): —C(=O)—NH—CH(—R$^2$—SCH$_3$)—(—C(=O)NHR$^2$(—R$^3$)—C(=O)NH—R$^3$—C(=O)OH; —C(=O)—NHR$^2$(—R$^3$)—C(=O)NH—R$^2$NH$_2$; —C(=O)—NH—R$^2$—R$^8$—R$^3$; and —C(=O)—NH—CH—(—C[=N]—NH$_2$)(—C[=O]—NH$_2$);

(e) Y is S(O) or S(O)$_2$;

(f) W is O, S, —NH or —NR$^2$;

(g) each R$^2$ is independently hydrogen or an optionally substituted or unsubstituted, branched or unbranched lower alkyl, alkenyl, alkynyl, alkylene, alkenylene or alkynylene; acyl; hydroxy; alkoxy; substituted or unsubstituted aryl; substituted or unsubstituted aralkyl; —CF$_3$; —NH$_2$; —NH—; —CH$_2$—S(O)$_n$R$^3$; —C(alkyl)$_2$-S(O)$_n$R$^3$; —CH(alkyl)-S(O)$_n$R$^3$; —CH(alkyl)NH$_2$; —C(alkyl)$_2$-NH$_2$; —CH$_2$—NH(alkyl); —C(alkyl)$_2$-NH(alkyl); —CH(alkyl)-NH(alkyl); CH$_2$NHR$^3$; —CH$_2$N(alkyl)R$^3$; —CH$_2$N(alkyl)R$^3$; —CH(alkyl)-NHR$^3$; —CH(alkyl)-N(alkyl)R$^3$; —C(alkyl)$_2$-NHR$^3$; —C(alkyl)$_2$-N(alkyl)R$^3$; —CH$_2$—C(=W)H; —CH$_2$C(=W)alkyl; —CH(alkyl)-C(=W)H; —CH(alkyl)-C(=W)alkyl; —(CH$_2$)$_p$OH; —C(alkyl)$_2$-C(=W)H; —C(alkyl)$_2$-C(=W)alkyl; —CH(alkenyl)-S(O)$_n$R$^3$; —CH$_2$NH$_2$; —CH(alkenyl)NH$_2$; —C(alkenyl)$_2$-NH$_2$; —CH$_2$—NH(alkenyl); —C(alkenyl)$_2$-NH(alkenyl); —CH(alkenyl)-NH(alkenyl); —CH$_2$—NHR$^3$; —CH$_2$—N(alkenyl)R$^3$; —CH(alkenyl)-NHR$^3$; —CH(alkenyl)-N(alkenyl)R$^3$; —C(alkenyl)$_2$-NHR$^3$; —C(alkenyl)$_2$-N(alkenyl)R$^3$; —CH$_2$—C(=W)H; —CH$_2$—C(=W)alkenyl; —CH(alkenyl)-C(=W)H; —CH(alkenyl)-C(=W)alkenyl;

—C(alkenyl)₂-C(=W)H; —C(alkenyl)₂-C(=W)alkenyl; —CH(alkynyl)-S(O)ₙR³; —CH(alkynyl)-NH₂; —C(alkynyl)₂-NH₂; —CH₂—NH(alkynyl); —C(alkynyl)₂-NH(alkynyl); —CH(alkynyl)-NH(alkynyl); —CH₂—NHR³; —CH₂—N(alkynyl)R³; —CH(alkynyl)-NHR³; —CH(alkynyl)-N(alkynyl)R³; —C(alkynyl)₂-NHR³; —C(alkynyl)₂-N(alkynyl)R³; —CH₂—C(=W)H; —CH₂—C(=W)alkynyl; —CH(alkynyl)-C(=W)H; —CH(alkynyl)-C(=W)alkynyl; —C(alkynyl)₂-C(=W)H; —C(alkynyl)₂-C(=W)alkynyl; —CH(alkoxy)-S(O)ₙR³; —CH(alkoxy)-NH₂; —C(alkoxy)₂-NH₂; —CH₂—NH(alkoxy); —C(alkoxy)₂-NH(alkoxy); —CH(alkoxy)-NH(alkoxy); —CH₂—NHR³; —CH₂—N(alkoxy)R³; —CH(alkoxy)-NHR³; —CH(alkoxy)-N(alkoxy)R³; —C(alkoxy)₂-NHR³; —C(alkoxy)₂-N(alkoxy)R³; —CH₂—C(=W)H; —CH₂C(=W)-alkoxy; —CH(alkoxy)-C(=W)H; —CH(alkoxy)-C(=W)alkoxy; —C(alkoxy)₂-C(=W)H; —C(alkoxy)₂-C(=W)alkoxy; —CH(CF₃)—S(O)ₙR³; —CH(CF₃)—NH₂; —(CF₃)₂—NH₂; —CH₂—NH(CF₃); —C(CF₃)₂—NH(CF₃); —CH(CF₃)—NH(CF₃); —CH₂—NHR³; —CH₂—N(CF₃)R³; —CH(CF₃)—NHR³; —CH(CF₃)—N(CF₃)R³; —C(CF₃)₂—NHR³; —C(CF₃)₂—N(CF₃)R³; —CH₂C(=W)H; —CH₂—C(=W)CF₃; —CH(CF₃)—C(=W)H; —CH(CF₃)—C(=W)CF₃; —C(CF₃)₂—C(=W)H; —C(CF₃)₂—C(=W)CF₃; —CH(NH)—S(O)ₙR³; —CH₂—NH—NH₂; —CH(NH₂)—NH(NH₂); —CH₂—NHR³; —CH₂—N(NH)R³; —CH(NH₂)—NHR³; —CH(NH₂)—N(NH₂)R³; —CH₂—C(=W)NH₂; —CHR²—C(=W)H; —CH₂—C(=W)H; —CH(NH₂)—C(=W)NH₂; —CH(NH₂)—NH₂; —CH₂—NH(NH₂); —CH₂—NHR³; —CH₂—N(NH₂)R³; —CH(NH₂)—NHR³; —CH(NH₂)—N(NH₂)R³; —CH₂—C(=W)H; —CH₂—C(=W)NH₂; —CH(NH₂)—C(=W)H; or —CH(NH₂)—C(=W)NH₂;

(h) each R³ is independently hydrogen; optionally substituted or unsubstituted, branched or unbranched alkyl, alkenyl, alkynyl, alkylene, alkenylene or alkynylene; CF₃; CN; amino; —C(R²²)(R²²)—S(O)ₙ—NH₂; —C(R²²)(R²²)—S(O)ₙ—CF₃; —C(R²²)(R²²)—NH₂, —C(R²²)(R²²)—NHR²², C(R²²)(R²²)—NR²²(alkyl); —C(R²²)(R²²)—NR²²(alkenyl); —C(R¹²)(R²²)—NR²² (alkynyl); C(R²²)(R²²)—NR²²(CF₃); and —C(R²²) (R²²)—C(=W)R²²; optionally substituted or unsubstituted aryl and arylene; optionally substituted or unsubstituted cycloalkyl; optionally substituted or unsubstituted alkylaryl, optionally substituted or unsubstituted aralkyl and aralkylene;

(i) each R²² is independently hydrogen or an optionally substituted or unsubstituted, branched or unbranched lower alkyl, alkenyl, alkynyl; acyl; hydroxy; alkoxy; substituted or unsubstituted aryl; substituted or unsubstituted arylene; substituted or unsubstituted aralkyl; amine, alkylamine, alkylsulfonyl, —CF₃; —NH₂; alkylacyl; amide; alkylamide;

(j) A is a disubstituted spacer selected from the group consisting of alkylene which optionally may have one or more heteroatoms, aryl, or cycloalkyl functions in the chain; alkenylene which optionally may have one or more heteroatoms, aryl, or cycloalkyl or functions in the chain; and optionally substituted aryl, and cycloalkyl,;

(k) R is selected from the group consisting of H; aryl; alkoxy; optionally substituted, branched or unbranched alkyl, alkenyl, alkynyl, cycloalkyl, and aralkyl;

(l) each n is independently 0, 1 or 2;
(m) each p is independently 0, 1, 2, 3, 4 or 5.

18. The pharmaceutical composition of claim 17, wherein Y is SO₂.

19. The pharmaceutical composition of claim 17, wherein Y is SO.

20. A pharmaceutical composition for the treatment of an HIV infection in a host comprising an effective anti-HIV treatment amount of a compound of the structure:

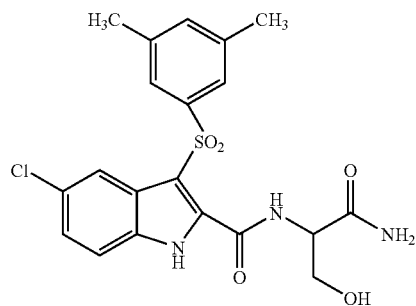

or a pharmaceutically acceptable salt or prodrug thereof; optionally in combination with one or more other anti-HIV agent, optionally with a pharmaceutically acceptable carrier or diluent.

21. A pharmaceutical composition for the treatment of an HIV infection in a host comprising an effective anti-HIV treatment amount of a compound of the structure:

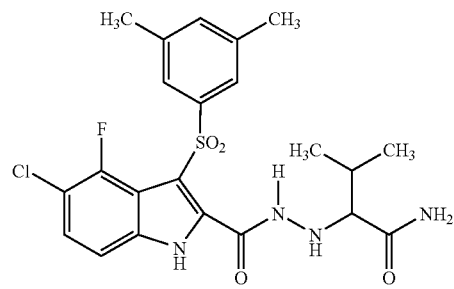

or a pharmaceutically acceptable salt or prodrug thereof optionally in combination with one or more other anti-HIV agent, optionally with a pharmaceutically acceptable carrier or diluent.

22. A pharmaceutical composition for the treatment of an HIV infection in a host comprising an effective anti-HIV treatment amount of a compound of the structure:

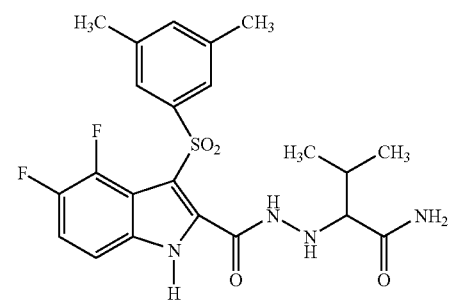

or a pharmaceutically acceptable salt or prodrug thereof: optionally in combination with one or more other anti-HIV agent, optionally with a pharmaceutically acceptable carrier or diluent.

23. A pharmaceutical composition for the treatment of an HIV infection in a host comprising an effective anti-HIV treatment amount of a compound of the structure:

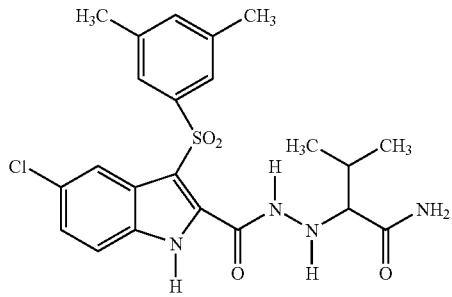

or a pharmaceutically acceptable salt or prodrug thereof optionally in combination with one or more other anti-HIV agent, optionally with a pharmaceutically acceptable carrier or diluent.

24. A pharmaceutical composition for the treatment or prophylaxis of an HIV infection in a host comprising an effective anti-HIV treatment amount of a compound of the structure:

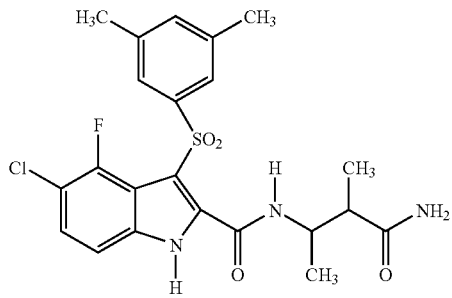

or a pharmaceutically acceptable salt or prodrug thereof; optionally in combination with one or more other anti-HIV agent, optionally with a pharmaceutically acceptable carrier or diluent.

25. A pharmaceutical composition for the treatment of an HIV infection in a host comprising an effective anti-HIV treatment amount of a compound of the structure:

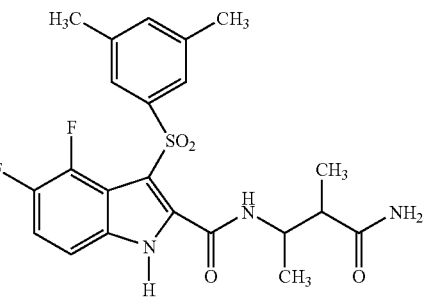

or a pharmaceutically acceptable salt or prodrug thereof; optionally in combination with one or more other anti-HIV agent, optionally with a pharmaceutically acceptable carrier or diluent.

26. A pharmaceutical composition for the treatment of an HIV infection in a host comprising an effective anti-HIV treatment amount of a compound of the structure:

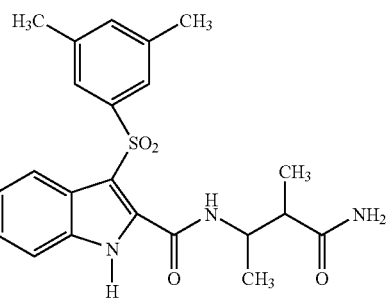

or a pharmaceutically acceptable salt or prodrug thereof optionally in combination with one or more other anti-HIV agent, optionally with a pharmaceutically acceptable carrier or diluent.

* * * * *